US012690909B2

(12) United States Patent
Caplan et al.

(10) Patent No.: US 12,690,909 B2
(45) Date of Patent: Jul. 28, 2026

(54) TISSUE TREATMENT SYSTEM WITH FLUID DELIVERY CONSOLE

(71) Applicant: Fractyl Health, Inc., Lexington, MA (US)

(72) Inventors: Jay Caplan, Boston, MA (US); Charles Abele, Brookline, MA (US); Gregory Andrew Dierksen, Brookline, MA (US); Andrew Hollett, Somerville, MA (US); Thomas C. Kochem, Watertown, MA (US); Adam Jaynes, Somerville, MA (US); Jeffrey Johnson, North Andover, MA (US); Jeffrey Lesica, Holliston, MA (US); Sara A. Morneau, Lincoln, MA (US); Bruno Piazzarolo, Arlington, MA (US); Jonathan Seidmann, Newton, MA (US)

(73) Assignee: Fractyl Health, Inc., Burlington, MA (US)

( * ) Notice: Subject to any disclaimer, the term of this patent is extended or adjusted under 35 U.S.C. 154(b) by 825 days.

(21) Appl. No.: 18/062,331

(22) Filed: Dec. 6, 2022

(65) Prior Publication Data

US 2023/0346451 A1 Nov. 2, 2023

Related U.S. Application Data

(63) Continuation of application No. PCT/US2021/038371, filed on Jun. 22, 2021.
(Continued)

(51) Int. Cl.
*A61B 18/04* (2006.01)
*A61B 18/00* (2006.01)
*A61B 18/02* (2006.01)

(52) U.S. Cl.
CPC .............. *A61B 18/04* (2013.01); *A61B 18/02* (2013.01); *A61B 2018/00577* (2013.01);
(Continued)

(58) Field of Classification Search
CPC .. A61B 2018/00642; A61B 2018/0262; A61B 2018/044; A61F 7/123
See application file for complete search history.

(56) References Cited

U.S. PATENT DOCUMENTS 5,084,044 A 1/1992 Quint
5,190,540 A 3/1993 Lee, I
(Continued)

FOREIGN PATENT DOCUMENTS

CA 2666661 C 1/2015
CN 1771888 A 5/2006
(Continued)

OTHER PUBLICATIONS

EP21828461.0 European Search Report and Opinion dated Jun. 28, 2024.
(Continued)

*Primary Examiner* — Ronald Hupczey, Jr.
(74) *Attorney, Agent, or Firm* — Wolf, Greenfield & Sacks, P.C.

(57) ABSTRACT

A system for performing a medical procedure in the intestine of a patient comprises a catheter for insertion into the intestine, a console, and a connector configured to operably attach the catheter to the console. The catheter comprises a shaft including a distal portion, and a functional assembly positioned on the distal portion of the shaft. The functional assembly is configured to receive fluid. The console comprises: a fluid reservoir configured to supply the fluid, a first syringe pump assembly configured to deliver the fluid to the functional assembly, a second syringe pump assembly con-
(Continued)

figured to deliver the fluid to the functional assembly, a fluid heater configured to heat the fluid, and a waste fluid reservoir configured to receive the fluid. The system is configured to treat target tissue of the intestine of the patient. Methods of treating target tissue are also provided.

24 Claims, 20 Drawing Sheets

Related U.S. Application Data

(60) Provisional application No. 63/042,356, filed on Jun. 22, 2020.

(52) U.S. Cl.
CPC .............. *A61B 2018/00642* (2013.01); *A61B 2018/00714* (2013.01); *A61B 2018/0212* (2013.01); *A61B 2018/0262* (2013.01); *A61B 2018/046* (2013.01)

(56) References Cited

U.S. PATENT DOCUMENTS

| | | | |
|---|---|---|---|
| 5,423,754 A | 6/1995 | Cornelius et al. | |
| 5,471,982 A | 12/1995 | Edwards et al. | |
| 5,496,311 A | 3/1996 | Abele et al. | |
| 5,515,100 A | 5/1996 | Nogo | |
| 5,542,928 A | 8/1996 | Evans et al. | |
| 5,549,559 A | 8/1996 | Eshel | |
| 5,575,772 A | 11/1996 | Lennox | |
| 5,704,934 A | 1/1998 | Neuwirth et al. | |
| 5,730,719 A | 3/1998 | Edwards | |
| 5,800,484 A | 9/1998 | Gough et al. | |
| 5,827,269 A | 10/1998 | Saadat | |
| 5,859,037 A | 1/1999 | Whitcomb et al. | |
| 5,869,037 A | 2/1999 | Crystal et al. | |
| 5,871,525 A | 2/1999 | Edwards et al. | |
| 5,879,347 A | 3/1999 | Saadat et al. | |
| 5,957,962 A | 9/1999 | Wallsten et al. | |
| 5,964,753 A | 10/1999 | Edwards | |
| 6,009,877 A | 1/2000 | Edwards | |
| 6,053,937 A | 4/2000 | Edwards et al. | |
| 6,056,744 A | 5/2000 | Edwards et al. | |
| 6,066,132 A | 5/2000 | Chen et al. | |
| 6,077,257 A | 6/2000 | Edwards et al. | |
| 6,112,123 A | 8/2000 | Kelleher et al. | |
| 6,293,909 B1 | 9/2001 | Chu et al. | |
| 6,325,777 B1 | 12/2001 | Zadno-Azizi et al. | |
| 6,325,798 B1 | 12/2001 | Edwards et al. | |
| 6,338,726 B1 | 1/2002 | Edwards et al. | |
| 6,358,245 B1 | 3/2002 | Edwards et al. | |
| 6,402,744 B2 | 6/2002 | Edwards et al. | |
| 6,405,732 B1 | 6/2002 | Edwards et al. | |
| 6,409,723 B1 | 6/2002 | Edwards | |
| 6,425,887 B1 | 7/2002 | McGuckin et al. | |
| 6,443,947 B1 | 9/2002 | Marko et al. | |
| 6,544,226 B1 | 4/2003 | Gaiser et al. | |
| 6,673,070 B2 | 1/2004 | Edwards et al. | |
| 6,712,814 B2 | 3/2004 | Edwards et al. | |
| 6,802,841 B2 | 10/2004 | Utley et al. | |
| 6,905,496 B1 | 6/2005 | Ellman et al. | |
| 6,962,587 B2 | 11/2005 | Johnson et al. | |
| 6,974,456 B2 | 12/2005 | Edwards et al. | |
| 7,077,841 B2 | 7/2006 | Gaiser et al. | |
| 7,111,627 B2 | 9/2006 | Stack et al. | |
| 7,122,031 B2 | 10/2006 | Edwards et al. | |
| 7,125,407 B2 | 10/2006 | Edwards et al. | |
| 7,156,860 B2 | 1/2007 | Wallsten | |
| 7,165,551 B2 | 1/2007 | Edwards et al. | |
| 7,241,295 B2 | 7/2007 | Maguire | |
| 7,326,207 B2 | 2/2008 | Edwards | |
| 7,371,215 B2 | 5/2008 | Colliou et al. | |
| 7,387,626 B2 | 6/2008 | Edwards et al. | |
| 7,422,587 B2 | 9/2008 | Bek et al. | |
| 7,507,234 B2 | 3/2009 | Utley et al. | |
| 7,507,238 B2 | 3/2009 | Edwards et al. | |
| 7,530,979 B2 | 5/2009 | Ganz et al. | |
| 7,556,628 B2 | 7/2009 | Utley et al. | |
| 7,585,296 B2 | 9/2009 | Edward et al. | |
| 7,632,268 B2 | 12/2009 | Utley et al. | |
| 7,632,291 B2 | 12/2009 | Stephens et al. | |
| 7,648,500 B2 | 1/2010 | Edwards et al. | |
| 7,758,623 B2 | 7/2010 | Dzeng et al. | |
| 7,762,977 B2 | 7/2010 | Porter et al. | |
| 7,947,038 B2 | 5/2011 | Edwards | |
| 7,959,627 B2 | 6/2011 | Utley et al. | |
| 7,993,336 B2 | 8/2011 | Jackson et al. | |
| 7,997,278 B2 | 8/2011 | Utley et al. | |
| 8,012,149 B2 | 9/2011 | Jackson et al. | |
| 8,066,689 B2 | 11/2011 | Mitelberg et al. | |
| 8,152,803 B2 | 4/2012 | Edwards et al. | |
| 8,177,853 B2 | 5/2012 | Stack et al. | |
| 8,192,426 B2 | 6/2012 | Stern et al. | |
| 8,251,992 B2 | 8/2012 | Utley et al. | |
| 8,262,610 B2 | 9/2012 | Duchon et al. | |
| 8,273,012 B2 | 9/2012 | Wallace et al. | |
| 8,323,229 B2 | 12/2012 | Shin et al. | |
| 8,364,237 B2 | 1/2013 | Stone et al. | |
| 8,377,055 B2 | 2/2013 | Jackson et al. | |
| 8,486,005 B2 | 7/2013 | Yodfat et al. | |
| 8,641,711 B2 | 2/2014 | Kelly et al. | |
| 8,740,894 B2 | 6/2014 | Edwards | |
| 8,790,705 B2 | 7/2014 | Geigle et al. | |
| 9,364,283 B2 | 6/2016 | Utley et al. | |
| 9,555,020 B2 | 1/2017 | Pasricha et al. | |
| 9,615,880 B2 | 4/2017 | Gittard et al. | |
| 9,757,535 B2 | 9/2017 | Rajagopalan et al. | |
| 9,844,641 B2 | 12/2017 | Rajagopalan et al. | |
| 10,232,143 B2 | 3/2019 | Rajagopalan et al. | |
| 10,299,857 B2 | 5/2019 | Rajagopalan et al. | |
| 10,349,998 B2 | 7/2019 | Levin et al. | |
| 10,610,663 B2 | 4/2020 | Rajagopalan et al. | |
| 10,765,474 B2 | 9/2020 | Kadamus et al. | |
| 10,864,352 B2 | 12/2020 | Rajagopalan et al. | |
| 10,869,718 B2 | 12/2020 | Rajagopalan et al. | |
| 10,973,561 B2 | 4/2021 | Caplan et al. | |
| 10,980,590 B2 | 4/2021 | Rajagopalan et al. | |
| 10,987,149 B2 | 4/2021 | Rajagopalan et al. | |
| 11,166,761 B2 | 11/2021 | Kadamus et al. | |
| 11,185,367 B2 | 11/2021 | Rajagopalan et al. | |
| 11,419,659 B2 | 8/2022 | Levin et al. | |
| 2002/0077594 A1 | 6/2002 | Chien et al. | |
| 2002/0192162 A1 | 12/2002 | Green | |
| 2003/0040804 A1 | 2/2003 | Stack et al. | |
| 2003/0093072 A1 | 5/2003 | Friedman | |
| 2003/0153905 A1 | 8/2003 | Edwards et al. | |
| 2003/0233065 A1 | 12/2003 | Steward et al. | |
| 2004/0082859 A1 | 4/2004 | Schaer | |
| 2004/0087936 A1 | 5/2004 | Stern et al. | |
| 2004/0133256 A1 | 7/2004 | Callister | |
| 2004/0148034 A1 | 7/2004 | Kagan et al. | |
| 2004/0204768 A1 | 10/2004 | Geitz | |
| 2004/0215180 A1 | 10/2004 | Starkebaum et al. | |
| 2004/0215296 A1 | 10/2004 | Ganz et al. | |
| 2004/0220559 A1 | 11/2004 | Kramer et al. | |
| 2005/0096638 A1 | 5/2005 | Starkebaum et al. | |
| 2005/0154386 A1 | 7/2005 | West et al. | |
| 2005/0165437 A1 | 7/2005 | Takimoto | |
| 2005/0171524 A1 | 8/2005 | Stern et al. | |
| 2005/0192652 A1 | 9/2005 | Cioanta et al. | |
| 2005/0203489 A1 | 9/2005 | Saadat et al. | |
| 2005/0222558 A1 | 10/2005 | Baxter et al. | |
| 2005/0245943 A1 | 11/2005 | Zvuloni et al. | |
| 2005/0251116 A1 | 11/2005 | Steinke et al. | |
| 2005/0273090 A1 | 12/2005 | Nieman et al. | |
| 2006/0070631 A1 | 4/2006 | Scopton et al. | |
| 2006/0118127 A1 | 6/2006 | Chinn | |
| 2006/0135963 A1 | 6/2006 | Kick et al. | |
| 2006/0155261 A1 | 7/2006 | Bek et al. | |
| 2006/0161107 A1* | 7/2006 | Mantle ...................... A61F 7/12 604/113 |
| 2006/0205992 A1 | 9/2006 | Lubock et al. | |

(56) References Cited

U.S. PATENT DOCUMENTS

| | | |
|---|---|---|
| 2006/0229954 A1* | 10/2006 | Nuno ............... G06Q 10/0875 |
| | | 700/83 |
| 2006/0247683 A1 | 11/2006 | Danek et al. |
| 2006/0293742 A1 | 12/2006 | Dann et al. |
| 2007/0016262 A1 | 1/2007 | Gross et al. |
| 2007/0032788 A1 | 2/2007 | Edwards et al. |
| 2007/0100355 A1 | 5/2007 | Bonde et al. |
| 2008/0045785 A1 | 2/2008 | Oyatsu |
| 2008/0091181 A1 | 4/2008 | Gabbay |
| 2008/0107744 A1 | 5/2008 | Chu |
| 2008/0119788 A1 | 5/2008 | Winter |
| 2008/0125760 A1 | 5/2008 | Gilboa |
| 2008/0125803 A1 | 5/2008 | Sadamasa et al. |
| 2008/0147056 A1 | 6/2008 | Van et al. |
| 2008/0207994 A1 | 8/2008 | Gonon |
| 2008/0243112 A1 | 10/2008 | De |
| 2008/0319504 A1 | 12/2008 | Loushin et al. |
| 2009/0012469 A1 | 1/2009 | Nita |
| 2009/0012518 A1 | 1/2009 | Utley et al. |
| 2009/0018533 A1 | 1/2009 | Perkins et al. |
| 2009/0048593 A1 | 2/2009 | Ganz et al. |
| 2009/0069805 A1 | 3/2009 | Fischer et al. |
| 2009/0270851 A1 | 10/2009 | Babkin et al. |
| 2010/0022891 A1 | 1/2010 | Zuluaga et al. |
| 2010/0030190 A1 | 2/2010 | Singh |
| 2010/0114087 A1 | 5/2010 | Edwards et al. |
| 2010/0114325 A1 | 5/2010 | Yang et al. |
| 2010/0168561 A1 | 7/2010 | Anderson |
| 2010/0168624 A1 | 7/2010 | Sliwa |
| 2010/0204673 A1 | 8/2010 | Miller |
| 2010/0204688 A1 | 8/2010 | Hoey et al. |
| 2010/0217151 A1 | 8/2010 | Gostout et al. |
| 2010/0256775 A1 | 10/2010 | Belhe et al. |
| 2010/0260703 A1 | 10/2010 | Yankelson et al. |
| 2011/0046537 A1 | 2/2011 | Errico et al. |
| 2011/0091564 A1 | 4/2011 | Chu |
| 2011/0106273 A1 | 5/2011 | Belhe et al. |
| 2011/0160648 A1 | 6/2011 | Hoey |
| 2011/0172659 A1 | 7/2011 | Brannan |
| 2011/0184401 A1 | 7/2011 | Iwata et al. |
| 2011/0319809 A1 | 12/2011 | Smith |
| 2012/0059364 A1 | 3/2012 | Baust et al. |
| 2012/0197245 A1 | 8/2012 | Burnett et al. |
| 2012/0203070 A1* | 8/2012 | Crenshaw ............... A61B 7/00 |
| | | 600/202 |
| 2012/0271277 A1 | 10/2012 | Fischell et al. |
| 2012/0271301 A1 | 10/2012 | Fischell et al. |
| 2013/0071466 A1 | 3/2013 | Chancellor et al. |
| 2013/0178910 A1 | 7/2013 | Azamian et al. |
| 2014/0031773 A1 | 1/2014 | Mikkaichi |
| 2014/0074077 A1 | 3/2014 | Lane |
| 2014/0088529 A1 | 3/2014 | Bengtson |
| 2014/0121646 A1 | 5/2014 | Lodin et al. |
| 2014/0135661 A1 | 5/2014 | Garrison et al. |
| 2014/0163664 A1 | 6/2014 | Goldsmith |
| 2014/0255458 A1 | 9/2014 | Li et al. |
| 2014/0324037 A1 | 10/2014 | Hoey et al. |
| 2015/0045825 A1 | 2/2015 | Caplan et al. |
| 2015/0141987 A1 | 5/2015 | Caplan et al. |
| 2015/0148615 A1* | 5/2015 | Brennan ................. A61B 3/16 |
| | | 128/853 |
| 2015/0148738 A1 | 5/2015 | Caplan et al. |
| 2015/0359594 A1 | 12/2015 | Ben-Oren et al. |
| 2016/0008050 A1 | 1/2016 | Rajagopalan et al. |
| 2016/0310200 A1 | 10/2016 | Wang |
| 2016/0354144 A1 | 12/2016 | Caplan et al. |
| 2017/0007310 A1* | 1/2017 | Rajagopalan ........ A61B 5/0084 |
| 2017/0165002 A1 | 6/2017 | Sharma et al. |
| 2017/0191035 A1 | 7/2017 | Sia et al. |
| 2017/0333122 A1* | 11/2017 | Rajagopalan ......... A61M 29/02 |
| 2018/0221622 A1 | 8/2018 | Rajagopalan et al. |
| 2020/0060758 A1 | 2/2020 | Rajagopalan et al. |
| 2020/0060942 A1 | 2/2020 | Rajagopalan et al. |
| 2020/0138505 A1 | 5/2020 | Levin et al. |
| 2020/0155217 A1 | 5/2020 | Morneau et al. |
| 2020/0261144 A1 | 8/2020 | Caplan et al. |
| 2020/0305972 A1 | 10/2020 | Kadamus et al. |
| 2020/0405388 A1 | 12/2020 | Rajagopalan et al. |
| 2021/0008336 A1 | 1/2021 | Rajagopalan et al. |
| 2021/0085390 A1 | 3/2021 | Kadamus et al. |
| 2021/0137995 A1 | 5/2021 | Rajagopalan et al. |
| 2021/0196341 A1 | 7/2021 | Rajagopalan et al. |
| 2021/0299404 A1 | 9/2021 | Rajagopalan et al. |
| 2021/0307816 A1 | 10/2021 | Rajagopalan et al. |
| 2022/0054180 A1 | 2/2022 | Rajagopalan et al. |
| 2022/0071653 A1 | 3/2022 | Mani et al. |

FOREIGN PATENT DOCUMENTS

| | | | |
|---|---|---|---|
| CN | 101212932 A | 7/2008 | |
| EP | 1698296 A1 | 9/2006 | |
| EP | 1886634 A1 | 2/2008 | |
| EP | 3071286 A1 | 9/2016 | |
| JP | 2002503512 A | 2/2002 | |
| JP | 2003520068 A | 7/2003 | |
| JP | 2004500184 A | 1/2004 | |
| JP | 2006509536 A | 3/2006 | |
| JP | 2006136726 A | 6/2006 | |
| JP | 2007502690 A | 2/2007 | |
| JP | 2008515464 A | 5/2008 | |
| JP | 2010142661 A | 7/2010 | |
| JP | 2010533036 A | 10/2010 | |
| JP | 2011517599 A | 6/2011 | |
| JP | 2013543423 A | 12/2013 | |
| JP | 2014503256 A | 2/2014 | |
| KR | 20080013945 A | 2/2008 | |
| WO | WO-9418896 A1 | 9/1994 | |
| WO | WO-9912489 A2 | 3/1999 | |
| WO | WO-0207628 A2 | 1/2002 | |
| WO | WO-02058577 A1 | 8/2002 | |
| WO | WO-02096327 A2 | 12/2002 | |
| WO | WO-02102453 A2 | 12/2002 | |
| WO | WO-03033045 A2 | 4/2003 | |
| WO | WO-03092609 A2 | 11/2003 | |
| WO | WO-2004064600 A2 | 8/2004 | |
| WO | WO-2006020370 A2 | 2/2006 | |
| WO | WO-2007044244 A2 | 4/2007 | |
| WO | WO-2007067919 A2 | 6/2007 | |
| WO | WO-2008002654 A2 | 1/2008 | |
| WO | WO-2010042461 A1 | 4/2010 | |
| WO | WO-2010125570 A1 | 11/2010 | |
| WO | WO-2010160301 A1 | 5/2011 | |
| WO | WO-2012009486 A2 | 1/2012 | |
| WO | WO-2012099974 A2 | 7/2012 | |
| WO | WO-2013130655 A1 | 9/2013 | |
| WO | WO-2013134541 A2 | 9/2013 | |
| WO | WO-2013159066 A1 | 10/2013 | |
| WO | WO-2014022436 A1 | 2/2014 | |
| WO | WO-2014026055 A1 | 2/2014 | |
| WO | WO-2014055997 A1 | 4/2014 | |
| WO | WO-2014070136 A1 | 5/2014 | |
| WO | WO-2015038973 A1 | 3/2015 | |
| WO | WO-2015077571 A1 | 5/2015 | |
| WO | WO-2015148541 A1 | 10/2015 | |
| WO | WO-2016011269 A1 | 1/2016 | |
| WO | WO-2017004432 A1 | 1/2017 | |
| WO | WO-2018089773 A1 | 5/2018 | |
| WO | WO-2019018362 A1 * | 1/2019 | ............ A61B 18/06 |
| WO | WO-2019136240 A1 | 7/2019 | |
| WO | WO-2020205844 A1 | 10/2020 | |
| WO | WO-2021081072 A1 | 4/2021 | |
| WO | WO-2021146190 A1 | 7/2021 | |
| WO | WO-2021146535 A1 | 7/2021 | |
| WO | WO-2021188781 A1 | 9/2021 | |
| WO | WO-2021262646 A1 | 12/2021 | |

OTHER PUBLICATIONS

Adams, et al. Theoretical design and evaluation of endoluminal ultrasound applicators for thermal therapy of pancreatic cancer under image guidance. AIP Conference Proceedings 1821, 110002 (2017); doi: http://dx.doi.org/10.1063/1.4977640.

(56) References Cited

OTHER PUBLICATIONS

Chathadi, et al. The role of endoscopy in ampullary and duodenal adenomas. Gastrointest Endosc. Nov. 2015;82(5):773-81. doi: 10.1016/j.gie.2015.06.027. Epub Aug. 7, 2015.

Cherrington, et al. Hydrothermal Duodenal Mucosal Resurfacing: Role in the Treatment of Metabolic Disease. Gastrointest Endosc Clin N Am. Apr. 2017;27(2):299-311. doi: 10.1016/j.giec.2016.12.002.

EP12736438.8 The Extended European Search Report dated Nov. 22, 2016.

EP14844285.8 The Extended European Search Report dated Apr. 25, 2017.

EP20150391.9 The Extended European Search Report dated Aug. 20, 2020.

EP20159816.6 The Extended European Search Report dated Aug. 17, 2020.

European search report and search opinion dated Mar. 8, 2016 for EP Application No. 13825257.2.

European search report and search opinion dated Mar. 17, 2016 for EP Application No. 13827149.9.

European search report and search opinion dated Aug. 4, 2015 for EP Application No. 13755156.0.

European Search Report and Search Opinion dated Aug. 7, 2017 for European Patent Application No. EP14864511.2.

European Search Report and Search Opinion dated Aug. 7, 2017 for European Patent Application No. EP15768945.6.

European search report and search opinion dated Nov. 25, 2015 for EP Application No. 13777572.2.

European search report with written opinion dated Feb. 1, 2018 for EP Application No. 15822378.

European search report with written opinion dated Dec. 2, 2016 for EP Application No. 14807116.

Final Office action dated Mar. 22, 2019 for U.S. Appl. No. 14/917,243.

Final Office action dated Apr. 5, 2019 for U.S. Appl. No. 14/609,334.

Final Office action dated Jun. 17, 19 for U.S. Appl. No. 14/609,332.

Final Office action dated Jul. 10, 2019 for U.S. Appl. No. 15/274,948.

Galvao Neto, et al. Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.

Grikscheit, et al. Tissue-engineered small intestine improves recovery after massive small bowel resection. Ann Surg., 2004, 240:748-754.

International search report and written opinion dated Feb. 20, 2015 for PCT Application No. US2014/711601.

International search report and written opinion dated Jun. 21, 2013 for PCT Application No. US2013/028082.

International search report and written opinion dated Jun. 26, 2015 for PCT Application No. US2015/022293.

International search report and written opinion dated Jul. 13, 2012 for PCT Application No. US2012/021739.

International search report and written opinion dated Aug. 8, 2013 for PCT Application No. US2013/037485.

International Search Report and Written Opinion dated Sep. 22, 2016 for International PCT Patent Application No. PCT/US2016/040512.

International search report and written opinion dated Oct. 23, 2015 for PCT/US2015/040775.

International search report and written opinion dated Nov. 8, 2013 for PCT Application No. US2013/052786.

International search report and written opinion dated Nov. 11, 2013 for PCT Application No. US2013/054219.

International search report and written opinion dated Dec. 24, 2014 for PCT Application No. US2014/055514.

International search report and written opinion dated Dec. 30, 2013 for PCT Application No. US2013/063753.

International search report dated Dec. 3, 2014 for PCT Application No. US2014/040957.

International search report with written opinion dated Jan. 9, 2018 for PCT/US2017/061074.

Miyawaki, et al. Inhibition of gastric inhibitory polypeptide signaling prevents obesity. Nat Med. Jul. 2002;8(7):738-42. Epub Jun. 17, 2002.

Notice of Allowance dated Jul. 7, 2017 for U.S. Appl. No. 15/274,764.

Notice of Allowance dated Sep. 14, 2017 for U.S. Appl. No. 15/274,809.

Office Action date Jul. 11, 2018 for U.S. Appl. No. 14/917,243.

Office Action date Aug. 9, 2018 for U.S. Appl. No. 14/673,565.

Office action dated Jan. 8, 2018 for U.S. Appl. No. 14/609,334.

Office Action dated Jan. 13, 2017 for U.S. Appl. No. 14/609,332.

Office action dated Feb. 29, 2016 for U.S. Appl. No. 14/609,334.

Office action dated Mar. 7, 2019 for U.S. Appl. No. 13/945,138.

Office Action dated Mar. 7, 2017 for U.S. Appl. No. 15/274,764.

Office Action dated Mar. 7, 2017 for U.S. Appl. No. 15/274,809.

Office action dated Mar. 7, 2019 for U.S. Appl. No. 14/673,565.

Office action dated Mar. 12, 2015 for U.S. Appl. No. 13/945,138.

Office action dated Mar. 19, 2018 for U.S. Appl. No. 14/470,503.

Office Action dated Mar. 23, 2017 for U.S. Appl. No. 13/945,138.

Office action dated Mar. 28, 2016 for U.S. Appl. No. 14/673,565.

Office action dated Apr. 4, 2018 for U.S. Appl. No. 15/156,585.

Office action dated May 16, 19 for U.S. Appl. No. 14/515,324.

Office action dated May 18, 2018 for U.S. Appl. No. 14/956,710.

Office Action dated May 31, 2017 for U.S. Appl. No. 15/274,764.

Office action dated Jun. 6, 2019 for U.S. Appl. No. 15/683,713.

Office Action dated Jun. 21, 2017 for U.S. Appl. No. 14/515,324.

Office Action dated Jun. 21, 2017 for U.S. Appl. No. 14/609,334.

Office Action dated Jun. 30, 2017 for U.S. Appl. No. 14/470,503.

Office action dated Aug. 5, 2015 for U.S. Appl. No. 13/945,138.

Office action dated Sep. 7, 2018 for U.S. Appl. No. 14/609,332.

Office Action dated Sep. 23, 2016 for U.S. Appl. No. 14/515,324.

Office action dated Oct. 4, 2018 for U.S. Appl. No. 14/515,324.

Office Action dated Oct. 7, 2016 for U.S. Appl. No. 13/945,138.

Office Action dated Nov. 2, 2017 for U.S. Appl. No. 15/156,585.

Office action dated Nov. 2, 2018 for U.S. Appl. No. 14/609,334.

Office Action dated Nov. 15, 2016 for U.S. Appl. No. 14/609,334.

Office action dated Nov. 16, 2017 for U.S. Appl. No. 14/609,332.

Office action dated Nov. 30, 2015 for U.S. Appl. No. 13/945,138.

Office action dated Nov. 30, 2017 for U.S. Appl. No. 14/673,565.

Office action dated Dec. 17, 2015 for U.S. Appl. No. 14/515,324.

Office action dated Dec. 18, 2017 for U.S. Appl. No. 14/515,324.

Office action dated Dec. 18, 2018 for U.S. Appl. No. 14/470,503.

Office action dated Dec. 19, 2017 for U.S. Appl. No. 13/945,138.

PCT/US14/66829 International Search Report dated Feb. 20, 2015.

PCT/US2019/012338 International Search Report dated Apr. 15, 2019.

PCT/US2021/038371 International Search Report and Written Opinion dated Oct. 1, 2021.

Rajagopalan, et al. Endoscopic Duodenal Mucosal Resurfacing for the Treatment of Type 2 Diabetes: 6-Month Interim Analysis From the First-in-Human Proof-of-Concept Study. Diabetes Care Dec. 2016; 39(12): 2254-2261. https://doi.org/10.2337/dc16-0383.

Rubino, et al. Potential of surgery for curing type 2 diabetes mellitus. Ann Surg. Nov. 2002;236(5):554-9.

Sarriá, et al. Morphometric study of the layers of the canine small intestine at five sampling sites. Vet J. Jun. 2012;192(3):498-502. doi: 10.1016/j.tvjl.2011.06.041. Epub Nov. 3, 2011.

Semkova, et al. Autologous transplantation of genetically modified iris pigment epithelial cells: A promising concept for the treatment of age-related macular degeneration and other disorders of the eye. Proc Natl Acad Sci U S A. Oct. 1, 2002; 99(20): 13090-13095.

Sen, et al. Autologous transplantation of endothelial progenitor cells genetically modified by adeno-associated viral vector delivering insulin-like growth factor-1 gene after myocardial infarction. Hum Gene Ther. Oct. 2010;21(10):1327-34.

Tolman, et al. Spectrum of liver disease in type 2 diabetes and management of patients with diabetes and liver disease. Diabetes care 30.3 (2007): 734-743.

Tomizawa, et al. Clinical Outcome of Endoscopic Mucosal Resection (EMR) of Sporadic, Non-Ampullary Duodenal Adenoma (SNADA): Predictor Analysis of Safety and Efficacy From a High Volume

(56)                    References Cited

OTHER PUBLICATIONS

U.S. Tertiary Referral Center. Gastrointestinal Endoscopy. 377. May 2017, vol. 85, Issue 5, Supplement, p. AB72. DOI: http://dx.doi.org/10.1016/j.gie.2017.03.089.
U.S. Appl. No. 14/917,243 Office Action dated Jun. 5, 2020.
U.S. Appl. No. 13/945,138 Notice of Allowance dated Dec. 22, 2020.
U.S. Appl. No. 14/515,324 Office Action dated Dec. 4, 2020.
U.S. Appl. No. 14/609,334 Notice of Allowance dated Dec. 10, 2020.
U.S. Appl. No. 14/609,334 Office Action dated Oct. 29, 2020.
U.S. Appl. No. 14/673,565 Office Action dated Dec. 24, 2020.
U.S. Appl. No. 14/673,565 Office Action dated Jun. 12, 2020.
U.S. Appl. No. 15/274,948 Notice of Allowance dated May 14, 2020.
U.S. Appl. No. 15/274,948 Office Action dated Nov. 20, 2018.
U.S. Appl. No. 15/406,572 Notice of Allowance dated Oct. 28, 2020.
U.S. Appl. No. 15/406,572 Office Action dated Apr. 14, 2020.
U.S. Appl. No. 15/406,572 Office Action dated Feb. 7, 2019.
U.S. Appl. No. 15/406,572 Office Action dated Nov. 15, 2019.
U.S. Appl. No. 15/917,480 Notice of Allowance dated Dec. 17, 2020.
U.S. Appl. No. 15/917,480 Office Action dated Nov. 20, 2020.
U.S. Appl. No. 16/267,771 Notice of Allowance dated Aug. 10, 2020.
U.S. Appl. No. 16/711,236 Office Action dated Dec. 10, 2020.
U.S. Appl. No. 16/900,563 Notice of Allowance dated Dec. 17, 2020.
U.S. Appl. No. 16/900,563 Office Action dated Nov. 9, 2020.
U.S. Appl. No. 13/945,138 Office Action dated Dec. 10, 2019.
U.S. Appl. No. 14/515,324 Office Action dated Mar. 31, 2020.
U.S. Appl. No. 14/609,334 Office Action dated Jan. 8, 2020.
U.S. Appl. No. 15/683,713 Notice of Allowance dated Mar. 10, 2020.
U.S. Appl. No. 15/683,713 Notice of Allowance dated Nov. 27, 2019.
U.S. Appl. No. 15/683,713 Office Action dated Oct. 10, 2019.
U.S. Appl. No. 15/917,480 Office Action dated Jan. 10, 2020.
U.S. Appl. No. 16/267,771 Office Action dated Feb. 6, 2020.
Van Baar, et al. Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. Apr. 2017 vol. 152, Issue 5, Supplement 1, p. S825. DOI: http://dx.doi.org/10.1016/S0016-5085(17)32851-2.

* cited by examiner

2210

Select Patient & Introduce Catheter into Small Intestine

2220

Attempt to Perform Submucosal Tissue Expansion at 1st Location

2225

Attempt to Perform Submucosal Tissue Expansion at 2nd Location

2230

Assess Submucosal Tissue Expansion

2235

Is Submucosal Tissue Expansion Adequate?

2240

Select New Area OR Stop Procedure

2250

Ablate Tissue

2260

Return to STEP 2220 if Desired

2200

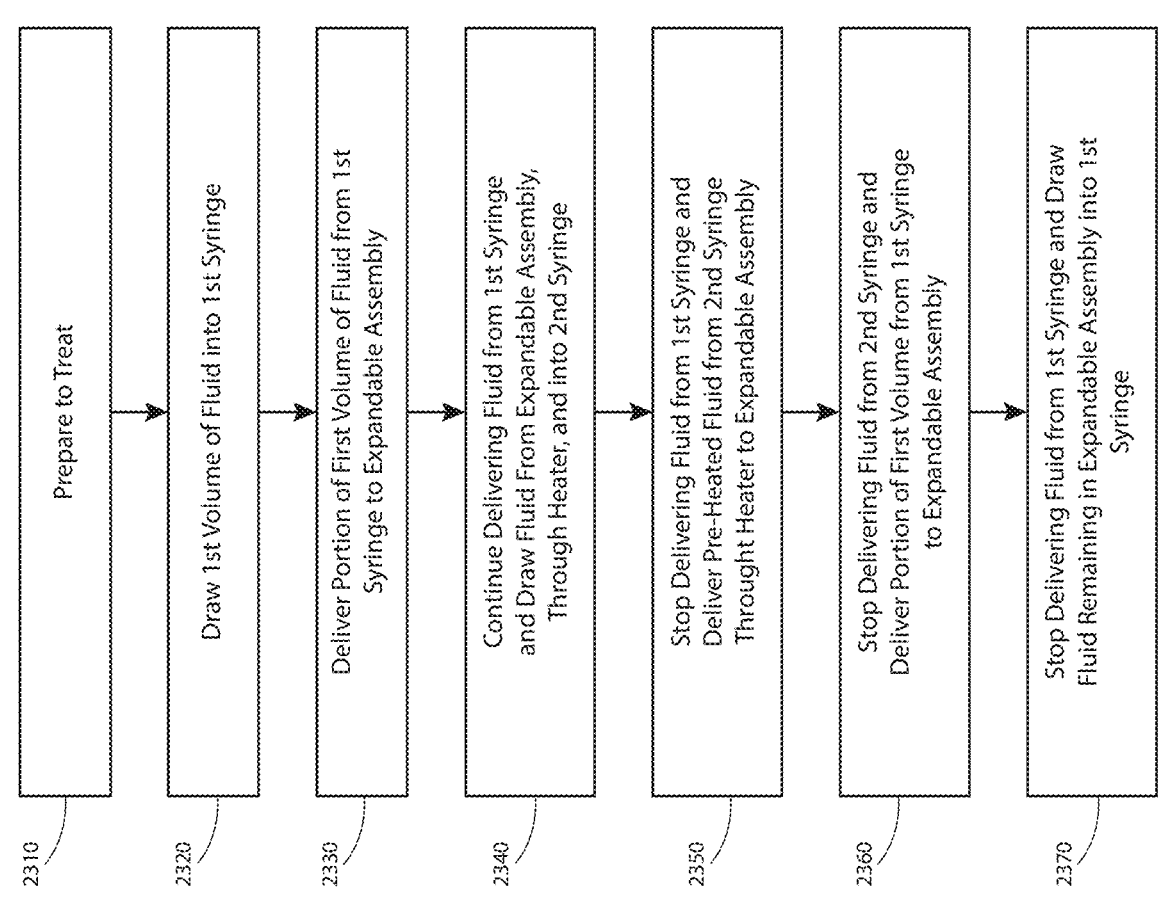

Prepare to Treat

Draw 1st Volume of Fluid into 1st Syringe

Deliver Portion of First Volume of Fluid from 1st Syringe to Expandable Assembly Continue Delivering Fluid from 1st Syringe and Draw Fluid From Expandable Assembly, Through Heater, and into 2nd Syringe Stop Delivering Fluid from 1st Syringe and Deliver Pre-Heated Fluid from 2nd Syringe Through Heater to Expandable Assembly Stop Delivering Fluid from 2nd Syringe and Deliver Portion of First Volume from 1st Syringe to Expandable Assembly Stop Delivering Fluid from 1st Syringe and Draw Fluid Remaining in Expandable Assembly into 1st Syringe

2310

2320

2330

2340

2350

2360

2370

2300

FIG 6G

TISSUE TREATMENT SYSTEM WITH FLUID DELIVERY CONSOLE

CROSS-REFERENCE TO RELATED APPLICATIONS

This application claims the benefit of PCT Application No. PCT/US2021/038371, filed Jun. 22, 2021, which claims the benefit of U.S. Provisional Application No. 63/042,356, filed Jun. 22, 2020, the content of which is incorporated herein by reference in its entirety.

This application is related to: U.S. patent application Ser. No. 16/438,362, entitled "Heat Ablation Systems, Devices and Methods for the Treatment of Tissue", filed Jun. 11, 2019; U.S. patent application Ser. No. 14/515,324, entitled "Tissue Expansion Devices, Systems and Methods", filed Oct. 15, 2014; U.S. patent application Ser. No. 16/711,236, entitled "Electrical Energy Ablation Systems, Devices and Methods for the Treatment of Tissue", filed Dec. 11, 2019; U.S. patent application Ser. No. 14/673,565, entitled "Methods, Systems and Devices for Performing Multiple Treatments on a Patient", filed Mar. 30, 2015; U.S. patent application Ser. No. 16/379,554, entitled "Methods, Systems and Devices for Reducing the Luminal Surface Area of the Gastrointestinal Tract", filed Apr. 9, 2019; U.S. patent application Ser. No. 14/917,243, entitled "Systems, Methods and Devices for Treatment of Target Tissue", filed Mar. 7, 2016; U.S. patent application Ser. No. 16/742,645, entitled "Intestinal Catheter Device and System", filed Jan. 14, 2020; U.S. patent application Ser. No. 16/798,117, entitled "Systems, Devices and Methods for Performing Medical Procedures in the Intestine", filed Feb. 21, 2020; U.S. patent application Ser. No. 15/812,969, entitled "Systems, Devices and Methods for Performing Medical Procedures in the Intestine", filed Nov. 14, 2017; U.S. patent application Ser. No. 16/400,491, entitled "Systems, Devices and Methods for Performing Medical Procedures in the Intestine", filed May 1, 2019; U.S. patent application Ser. No. 16/905,274, entitled "Material Depositing System for Treating a Patient", filed Jun. 18, 2020; International PCT Patent Application Serial Number PCT/US2020/025925, entitled "Systems, Devices and Methods for Treating Metabolic Medical Conditions", filed Mar. 31, 2020; U.S. patent application Ser. No. 17/021,798, entitled "Methods, Systems and Devices for Reducing the Luminal Surface Area of the Gastrointestinal Tract", filed Sep. 15, 2020; International PCT Patent Application Serial Number PCT/US2020/056627, entitled "Systems, Devices, and Methods for Performing Medical Procedures in the Intestine", filed Oct. 21, 2020; U.S. patent application Ser. No. 17/095,108, entitled "Systems, Devices and Methods for the Creation of a Therapeutic Restriction in the Gastrointestinal Tract", filed Nov. 11, 2020; U.S. patent application Ser. No. 17/096,855, entitled "Methods and Systems for Treating Diabetes and Related Diseases and Disorders", filed Nov. 12, 2020; U.S. patent application Ser. No. 17/110,720, entitled "Injectate Delivery Devices, Systems and Methods", filed Dec. 3, 2020; International PCT Patent Application Serial Number PCT/US2021/013072, entitled "Tissue Treatment Devices, Systems, and Methods", filed Jan. 12, 2021; International PCT Patent Application Serial Number PCT/US2021/013600, entitled "Automated Tissue Treatment Devices, Systems, and Methods", filed Jan. 15, 2021; U.S. Provisional Patent Application Ser. No. 63/148,551, entitled "System for Treating a Patient", filed Feb. 11, 2021; U.S. patent application Ser. No. 17/181,969, entitled "Methods and Systems for Treating Diabetes and Related Diseases and Disorders", filed Feb. 22, 2021; U.S. patent application Ser. No. 17/189,772, entitled "Methods and Systems for Treating Diabetes and Related Diseases and Disorders", filed Mar. 2, 2021; U.S. patent application Ser. No. 14/609,334, entitled "Ablation Systems, Devices, and Methods for the Treatment of Tissue", filed Mar. 4, 2021; International PCT Patent Application Serial Number PCT/US2021/022938, entitled "Systems, Devices and Methods for Treating Diabetes", filed Mar. 18, 2021; U.S. patent application Ser. No. 17/214,157, entitled "Systems and Methods for Deposition Material in a Patient", filed Mar. 26, 2021; and U.S. patent application Ser. No. 17/222,480, entitled "Devices and Methods for the Treatment of Tissue", filed Apr. 5, 2021; the contents of each of which is incorporated herein by reference in its entirety for all purposes.

TECHNICAL FIELD

The present inventive concepts relate generally to tissue treatment systems, and in more particular, tissue treatment systems that include a fluid delivery console and a treatment device.

BACKGROUND

Numerous diagnostic and therapeutic procedures are performed in the small and large intestine, as well as other locations of the gastrointestinal tract. Devices used in these procedures can be difficult to maneuver and otherwise operate, and they often have limited functionality. There is a need for improved systems and devices for treating and diagnosing tissue of the intestine, as well as a need for methods of treating intestinal tissue to provide an improved therapy for various diseases and disorders.

BRIEF SUMMARY

According to an aspect of the present inventive concepts, a system for performing a medical procedure in the intestine of a patient, the system comprises: a catheter for insertion into the intestine, the catheter comprising a shaft including a distal portion, and a functional assembly positioned on the distal portion of the shaft, such that the functional assembly is configured to receive fluid; a console comprising a fluid reservoir configured to store the fluid, a first syringe pump assembly configured to deliver the fluid to the functional assembly, a second syringe pump assembly configured to deliver the fluid to the functional assembly, a fluid heater configured to heat the fluid, and a waste fluid reservoir configured to receive the fluid; and a connector configured to operably attach the catheter to the console. The system can be configured to treat target tissue of the intestine of the patient.

In some embodiments, the functional assembly comprises a balloon.

In some embodiments, the system is configured to treat the target tissue by: providing a first volume of fluid at a temperature below body temperature and recirculating the first volume of fluid within the functional assembly to cool the target tissue and tissue proximate the target tissue; and providing a second volume of fluid at an elevated ablative temperature and recirculating the second volume of fluid within the functional assembly to ablate the target tissue. The system can be configured to deliver the first volume of fluid prior to the delivery of the second volume of fluid or after the delivery of the second volume of fluid. The system can be configured to deliver the first volume of fluid prior to the delivery of the second volume of fluid, and the system can be further configured to deliver a third volume of fluid after the delivery of the second volume of fluid, and the third volume of fluid can comprise fluid at a temperature below body temperature that during its delivery cools the target tissue and tissue proximate the target tissue. At least a portion of the first volume of fluid and the second volume of fluid can comprise the same fluid. The fluid heater can comprise an inline heater, and the second volume of fluid can be heated by the inline heater via two passes through the inline heater. During the first pass through the inline heater, the inline heater can be powered to a higher level than during the second pass through the inline heater. The console can operate at a peak power level while the heater is powered to the higher level. The second volume of fluid can be delivered to the functional assembly at a rate of at least 8 mL/s, 9 mL/s, and/or 10 mL/s. The first volume of fluid can comprise fluid at room temperature. The treatment can further comprise delivering a third volume of fluid to cool the target tissue after the target tissue has been ablated. The console can be configured to prevent delivery of the second volume of fluid to the functional assembly unless a volume of at least the third volume of fluid is present in the first syringe pump assembly prior to the delivery of the second volume of fluid to the functional assembly.

In some embodiments, the fluid heater comprises an inline heater, and the fluid heater is configured to be pre-heated prior to the second volume of fluid passing therethrough. The system can be configured to perform multiple treatment steps, and the fluid heater can be configured to be pre-heated between each of the multiple treatment steps.

In some embodiments, the system further comprises a closed-loop control algorithm configured to control the fluid heater.

In some embodiments, the system comprises at least one reusable component, and the system is configured to perform a disinfection procedure of the at least one reusable component. The disinfection procedure can comprise a low-level disinfection procedure. The disinfection procedure can comprise a high-level disinfection procedure. The system can be configured to heat at least a portion of the at least one reusable component to at least 93° C., at least 95° C., or at least 97° C., for a minimum time period of at least 45 seconds, at least 60 seconds, and/or at least 90 seconds, and/or for a maximum time period of no more than 3 minutes, no more than 4 minutes, and/or no more than 5 minutes.

In some embodiments, the console is configured to determine one or more parameters related to the treatment of the target tissue. The one or more treatment parameters can be selected from the group consisting of: a flow rate; a fluid temperature; an energy level; a pressure; a duration; and combinations thereof. The one or more treatment parameters can be based on ambient temperature. At least one of the one or more parameters can be predetermined prior to a treatment procedure.

In some embodiments, the system is configured to treat a first axial segment of the intestine that includes a first portion of the target tissue, and subsequently treat a second axial segment of the intestine that includes a second portion of the target tissue. The system may not maintain a reservoir of fluid at an ablative temperature during the medical procedure. The system may not maintain a reservoir of fluid at an ablative temperature between the treatment of the first axial segment and the second axial segment. The fluid reservoir can comprise a first reservoir, and the system can comprise a second reservoir configured to maintain fluid at an ablative temperature during at least a portion of the medical procedure. The fluid heater can be configured to heat fluid within the second reservoir to the ablative temperature. The fluid reservoir can comprise a first reservoir, and the system can comprise a second reservoir configured to maintain fluid at an ablative temperature between the treatment of the first axial segment and the treatment of the second axial segment. The fluid heater can be configured to heat fluid within the second reservoir to the ablative temperature.

In some embodiments, the system is configured to heat fluid within the second syringe pump assembly to an ablative temperature and to deliver the heated fluid from the second syringe pump assembly to the functional assembly to ablate the target tissue.

In some embodiments, the system further comprises a user-activated control, and the system is configured to prevent the performance of one or more procedural steps until the user-activated control is activated. The user-activated control can be configured to be activated by an operator of the system when the functional assembly is properly positioned within the intestine of the patient. The one or more procedural steps can comprise a tissue expansion step. The one or more procedural steps can comprise a tissue ablation step.

In some embodiments, the first syringe pump assembly and/or the second syringe pump assembly comprise at least one syringe operably attachable to the console. The at least one syringe can be configured to rotate to lockingly engage with the console. The first syringe pump assembly and/or second syringe pump assembly can provide user feedback when the at least one syringe is properly connected to the console. The system can be configured to detect when the at least one syringe is properly connected to the console.

In some embodiments, the first syringe pump assembly and/or the second syringe pump assembly comprise at least one syringe comprising an integral rotatably-locking style connector.

In some embodiments, the system further comprises a cartridge configured to operably attach to the console and/or to the connector. The system can be configured to detect when the cartridge is properly connected to the console. The cartridge can comprise one or more integral connectors fixedly attached to a wall of the cartridge without the use of any adhesive. At least one of the one or more integral connectors can be fixedly attached to the wall of the cartridge with a press fit connection. At least one of the one or more integral connectors can be configured to rotatably attach to a mating connector of the cartridge. The at least one integral connector can be configured to rotatably attach in a single-handed operation. At least one of the one or more integral connectors can comprise a rotatably-locking style connector. The cartridge can comprise one or more fluid conduits constructed and arranged to withstand one or more functional conditions. The one or more functional conditions can comprise a vacuum pressure of at least −3 psi, −7 psi, and/or −14.7 psi. At least a portion of at least one of the one or more fluid conduits can be constructed and arranged to collapse to an occlusion condition under a compressing force of a pinch valve. The system can be configured to detect if a pinch valve fails to collapse a conduit to an occlusion condition. The one or more functional conditions can comprise a temperature of at least 60° C., 80° C., and/or 100° C.

In some embodiments, the fluid reservoir comprises a flexible housing. The housing can comprise a softened polyvinyl chloride. The reservoir can comprise a handle. The reservoir can comprise an intake manifold. The fluid reservoir can comprise a temperature sensor operably connected to the console. The console can comprise an infrared temperature sensor configured to measure the temperature of fluid within the fluid reservoir.

In some embodiments, the system is configured to use no more than a target procedural volume of fluid to perform the medical procedure, and the target procedure volume comprises no more than 5 L, 4 L, 3 L, and/or 2 L of fluid. The first reservoir can be configured to be filled with at least the target procedural volume of fluid prior to the starting the medical procedure.

In some embodiments, the connector comprises two conduits that have been formed in a single extrusion process.

In some embodiments, the system further comprises a first conduit and a second conduit, and the connector comprises the second conduit, and the first conduit is fluidly attached between the fluid heater and the second conduit, and the second conduit is further fluidly attached to the functional assembly, and the first conduit comprises a length of less than 10 inches, 8 inches, and/or 6 inches.

In some embodiments, the functional assembly comprises a balloon manufactured using a non-compliant material.

In some embodiments, the console further comprises a backup power supply. The backup power supply can comprise a battery. The backup power supply can comprise an energy capacity sufficient to allow the system to transition one or more components of the system into a patient-safe mode. The system can be configured to transition from a treatment mode to a patient-safe mode in the event of a power failure during treatment of the target tissue.

In some embodiments, the system comprises one or more valves, and the waste fluid reservoir is positioned below the functional assembly when the functional assembly is positioned within the intestine of the patient, and in the event of a power loss, the one or more valves are configured to automatically open to cause fluid within the functional assembly to flow into the waste fluid reservoir.

In some embodiments, the console is configured to monitor one or more parameters of the system to assess the mechanical integrity of the catheter. The console can be configured to identify leaks and/or obstructions based on the one or more parameters. The identification of leaks and/or obstructions can be based on comparing the one or more parameters to one or more thresholds. The one or more thresholds can be adjusted based on the temperature of fluid being circulated through the functional assembly. The system can be configured to monitor for leaks while fluid at an ablative temperature is be being circulated through the functional assembly and to cause cooling fluid to be delivered to the functional assembly upon detection of a leak. The system can be configured to monitor for obstructions while fluid at an ablative temperature is be being circulated through the functional assembly and to remove fluid from the functional assembly upon detection of an obstruction.

In some embodiments, the system is further configured to perform a tissue expansion procedure. The system can be configured to control the volume of fluid within the functional assembly during the tissue expansion procedure and to control a flow rate of fluid to and/or from the functional assembly during the target tissue treatment. The system can further comprise a syringe pump assembly configured to perform the controlling of the volume of fluid within the functional assembly and the controlling of the flow rate of fluid to the functional assembly. The catheter can further comprise multiple fluid delivery elements configured to deliver injectate into tissue to perform the tissue expansion procedure. The system can further comprise multiple fluid delivery assemblies, and each fluid delivery assembly can be configured to independently deliver injectate to a corresponding fluid delivery element. The multiple fluid delivery assemblies can each comprise a syringe pump. The system can be configured to prevent the treatment of target tissue if a tissue expansion procedure has not been performed. The system can be configured to treat the target tissue after performing the tissue expansion procedure. The system can be configured to prevent the treating of the target tissue if a maximum time period has elapsed since performing the tissue expansion procedure. The maximum time period can comprise a duration of no more than 10 minutes and/or no more than 5 minutes.

In some embodiments, the system does not comprise more than two syringe pump assemblies configured to deliver fluid to the functional assembly, and the first syringe pump assembly comprises a single syringe and the second syringe pump assembly comprises a single syringe. The single syringe of the first syringe pump assembly and the single syringe of the second syringe pump assembly can each comprise a maximum volume of 500 mL, 300 mL, 200 mL, and/or 150 mL.

In some embodiments, the system is configured to prevent the treatment of target tissue if fluid in the fluid reservoir is not above a minimum volume.

In some embodiments, the system is configured to prevent the treatment of target tissue if space in the waste reservoir is not above a minimum volume.

In some embodiments, the system further comprises at least one microcontroller. The at least one microcontroller can comprise a first microcontroller configured to control at least the first syringe pump assembly and a second microcontroller configured to control the fluid heater. The system further comprise at least one valve assembly, and the at least one microcontroller can comprise a first microcontroller configured to control at least the first syringe pump assembly and a second microcontroller configured to control the valve assembly.

In some embodiments, the system further comprises an electromechanical safety mechanism configured to prevent a fluid pressure from exceeding a safety threshold. The electromechanical safety mechanism can comprise a mechanism selected from the group consisting of: a load cell; an overpressure valve; a sheer nut on a linear drive mechanism; a clutch on a linear drive mechanism; a current limiter; and combinations thereof.

In some embodiments, the system further comprises an umbilical configured to operably connect the catheter to the console. The umbilical can comprise one or more insulating layers, insulating conduits, and/or other insulating materials. The umbilical can comprise a heater.

In some embodiments, the system comprises at least one user-replaceable assembly secured to the console with hooks, latches, and/or locks.

The technology described herein, along with the attributes and attendant advantages thereof, will best be appreciated and understood in view of the following detailed description taken in conjunction with the accompanying drawings in which representative embodiments are described by way of example.

INCORPORATION BY REFERENCE

All publications, patents, and patent applications mentioned in this specification are herein incorporated by reference to the same extent as if each individual publication, patent, or patent application was specifically and individually indicated to be incorporated by reference. The content of all publications, patents, and patent applications mentioned in this specification are herein incorporated by reference in their entirety for all purposes.

BRIEF DESCRIPTION OF THE DRAWINGS

FIG. 6G illustrates a flow chart of a method of treating tissue, consistent with the present inventive concepts.

DETAILED DESCRIPTION OF THE DRAWINGS

Figure 1:
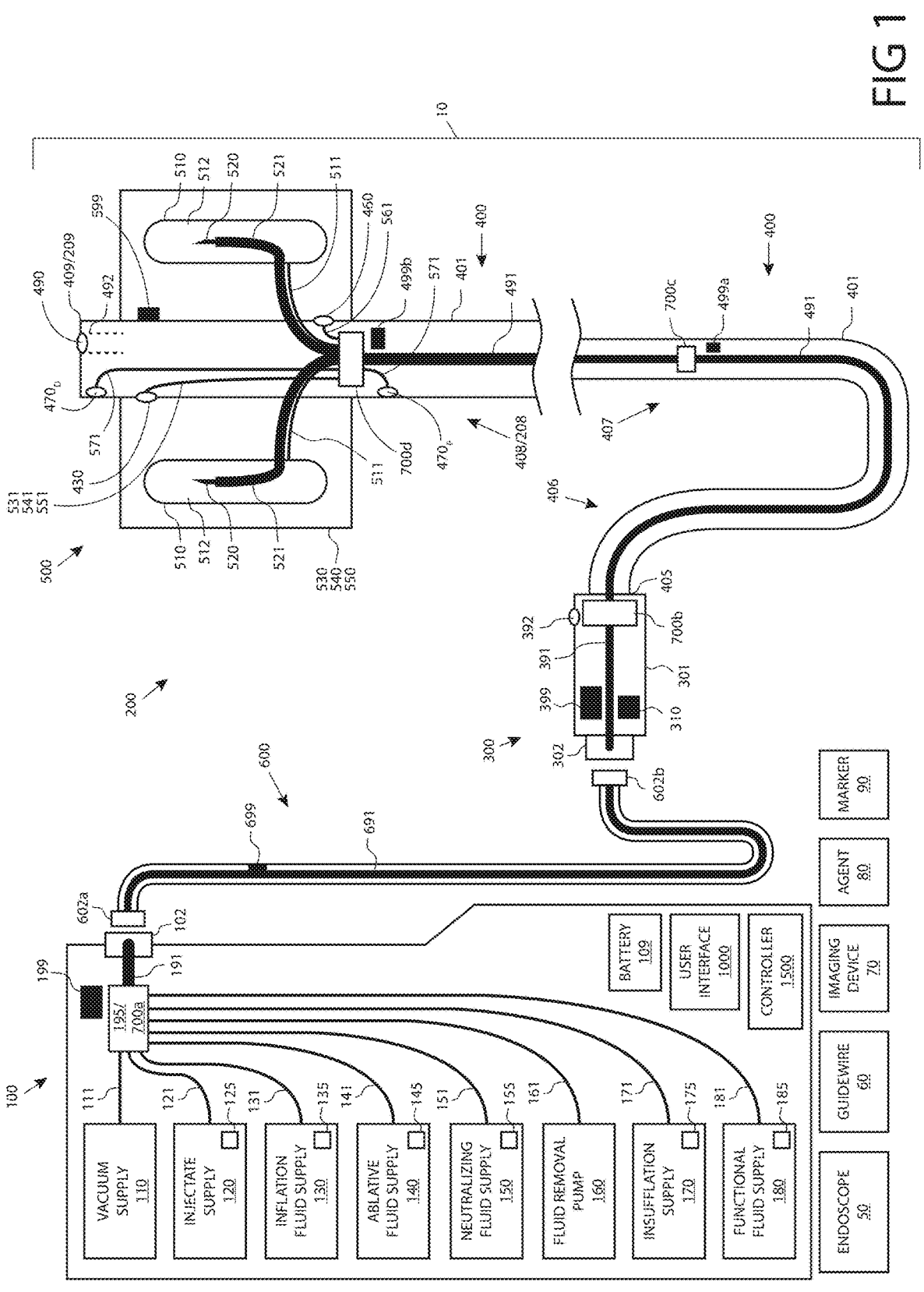
FIG. 1 illustrates a system for treating and/or diagnosing gastrointestinal tissue, consistent with the present inventive concepts.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third, etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

As used herein, the term "proximate", when used to describe proximity of a first component or location to a second component or location, is to be taken to include one or more locations near to the second component or location, as well as locations in, on and/or within the second component or location. For example, a component positioned proximate an anatomical site (e.g. a target tissue location), shall include components positioned near to the anatomical site, as well as components positioned in, on and/or within the anatomical site.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence. Correspondingly, the terms "prevent", "preventing", and "prevention" shall include the acts of "reduce", "reducing", and "reduction", respectively.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "one or more", where used herein can mean one, two, three, four, five, six, seven, eight, nine, ten, or more, up to any number.

The terms "and combinations thereof" and "and combinations of these" can each be used herein after a list of items that are to be included singly or collectively. For example, a component, process, and/or other item selected from the group consisting of: A; B; C; and combinations thereof, shall include a set of one or more components that comprise: one, two, three or more of item A; one, two, three or more of item B; and/or one, two, three, or more of item C.

In this specification, unless explicitly stated otherwise, "and" can mean "or", and "or" can mean "and". For example, if a feature is described as having A, B, or C, the feature can have A, B, and C, or any combination of A, B, and C. Similarly, if a feature is described as having A, B, and C, the feature can have only one or two of A, B, or C.

As used herein, when a quantifiable parameter is described as having a value "between" a first value X and a second value Y, it shall include the parameter having a value of: at least X, no more than Y, and/or at least X and no more than Y. For example, a length of between 1 and 10 shall include a length of at least 1 (including values greater than 10), a length of less than 10 (including values less than 1), and/or values greater than 1 and less than 10.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

As used herein, the term "threshold" refers to a maximum level, a minimum level, and/or range of values correlating to a desired or undesired state. In some embodiments, a system parameter is maintained above a minimum threshold, below a maximum threshold, within a threshold range of values, and/or outside a threshold range of values, such as to cause a desired effect (e.g. efficacious therapy) and/or to prevent or otherwise reduce (hereinafter "prevent") an undesired event (e.g. a device and/or clinical adverse event). In some embodiments, a system parameter is maintained above a first threshold (e.g. above a first temperature threshold to cause a desired therapeutic effect to tissue) and below a second threshold (e.g. below a second temperature threshold to prevent undesired tissue damage). In some embodiments, a threshold value is determined to include a safety margin, such as to account for patient variability, system variability, tolerances, and the like. As used herein, "exceeding a threshold" relates to a parameter going above a maximum threshold, below a minimum threshold, within a range of threshold values and/or outside of a range of threshold values.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

As used herein, the term "functional element" is to be taken to include one or more elements constructed and arranged to perform a function. A functional element can comprise a sensor and/or a transducer. In some embodiments, a functional element is configured to deliver energy and/or otherwise treat tissue (e.g. a functional element configured as a treatment element). Alternatively or additionally, a functional element (e.g. a functional element comprising a sensor) can be configured to record one or more parameters, such as a patient physiologic parameter; a patient anatomical parameter (e.g. a tissue geometry parameter); a patient environment parameter; and/or a system parameter. In some embodiments, a sensor or other functional element is configured to perform a diagnostic function (e.g. to gather data used to perform a diagnosis). In some embodiments, a functional element is configured to perform a therapeutic function (e.g. to deliver therapeutic energy and/or a therapeutic agent). In some embodiments, a functional element comprises one or more elements constructed and arranged to perform a function selected from the group consisting of: deliver energy; extract energy (e.g. to cool a component); deliver a drug or other agent; manipulate a system component or patient tissue; record or otherwise sense a parameter such as a patient physiologic parameter or a system parameter; and combinations of one or more of these. A functional element can comprise a fluid and/or a fluid delivery system. A functional element can comprise a reservoir, such as an expandable balloon or other fluid-maintaining reservoir. A "functional assembly" can comprise an assembly constructed and arranged to perform a function, such as a diagnostic and/or therapeutic function. A functional assembly can comprise an expandable assembly. A functional assembly can comprise one or more functional elements.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such as: light (e.g. a transducer comprising a light emitting diode or light bulb), sound (e.g. a transducer comprising a piezo crystal configured to deliver ultrasound energy); pressure (e.g. an applied pressure or force); heat energy; cryogenic energy; chemical energy; mechanical energy (e.g. a transducer comprising a motor or a solenoid); magnetic energy; and/or a different electrical signal (e.g. different than the input signal to the transducer). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one or more of these.

As used herein, the term "fluid" can refer to a liquid, gas, gel, or any flowable material, such as a material which can be propelled through a lumen and/or opening.

As used herein, the term "material" can refer to a single material, or a combination of two, three, four, or more materials.

It is appreciated that certain features of the inventive concepts, which are, for clarity, described in the context of separate embodiments, may also be provided in combination in a single embodiment. Conversely, various features of the inventive concepts which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the inventive concepts have been simplified to focus on elements that are relevant for a clear understanding of the inventive concepts, while eliminating, for purposes of clarity, other elements that those of ordinary skill in the art will appreciate may also comprise a portion of the inventive concepts. However, because such elements are well known in the art, and because they do not necessarily facilitate a better understanding of the inventive concepts, a description of such elements is not provided herein.

Terms defined in the present disclosure are only used for describing specific embodiments of the present disclosure and are not intended to limit the scope of the present disclosure. Terms provided in singular forms are intended to include plural forms as well, unless the context clearly indicates otherwise. All of the terms used herein, including technical or scientific terms, have the same meanings as those generally understood by an ordinary person skilled in the related art, unless otherwise defined herein. Terms defined in a generally used dictionary should be interpreted as having meanings that are the same as or similar to the contextual meanings of the relevant technology and should not be interpreted as having ideal or exaggerated meanings, unless expressly so defined herein. In some cases, terms defined in the present disclosure should not be interpreted to exclude the embodiments of the present disclosure.

Provided herein are tissue treatment systems including a fluid delivery console and a treatment device, as well as methods for treating target tissue. The systems can be configured to ablate mucosal tissue, such as mucosal tissue of the duodenum or other intestinal location. The system can include both disposable and reusable components. The treatment device can comprise a catheter or other device that includes a functional assembly for receiving fluid, such as fluid that is at an ablative temperature. The console can include various components for delivering the fluid to the treatment device, as well as components for withdrawing fluid from the treatment device. In some embodiments, the console includes one, two, or more pumping assemblies, such as syringe pumping assemblies. The console can include a heater configured to heat the fluid, and a waste fluid reservoir configured to store fluid that has been withdrawn from the treatment device.

Referring now to FIG. 1, a system for treating and/or diagnosing ("treating" herein) gastrointestinal tissue is illustrated, consistent with the present inventive concepts. System 10 includes console 100 that operably attaches to a catheter, catheter 200. System 10 and catheter 200 can be used by an operator (e.g. one or more clinicians) to perform a therapeutic procedure and/or a diagnostic procedure. Catheter 200 can be constructed and arranged to treat and/or diagnose target tissue, such as tissue of the small intestine (e.g. mucosal tissue of the duodenum and/or jejunum) and/or other locations within the gastrointestinal (GI) tract. Catheter 200 can be constructed and arranged to ablate or remove tissue, such as by delivering energy to tissue. Alternatively or additionally, catheter 200 can be constructed and arranged to expand one or more layers of tissue of the GI tract, such as when a submucosal tissue expansion procedure is performed in one segment of the GI tract after which an energy delivery to mucosal tissue is performed in that same segment. Catheter 200 can be constructed and arranged to treat multiple relatively contiguous segments ("contiguous segments" herein) or non-contiguous segments of the GI tract. In some embodiments, two or more axial segments of submucosal tissue of intestine are expanded, after which a single ablation procedure is performed (e.g. an ablation of a length of tissue of similar or lesser length as compared to the cumulative length of submucosal tissue expanded, such as when the length treated by a single ablation step is greater than the length expanded in a single tissue expansion step), such as is described herein in reference to FIGS. 1B and 1C.

In some embodiments, system 10 comprises one or more body access devices, such as endoscope 50 shown. Catheter 200 can be configured to be inserted through one or more working channels of endoscope 50 and/or alongside endoscope 50. In some embodiments, catheter 200 is inserted through a sheath attached to endoscope 50. Catheter 200 can comprise a length such that it can be inserted through the patient's mouth and into one or more locations within the stomach, the duodenum, the jejunum and/or the ileum.

In some embodiments, system 10 comprises one or more guidewires, such as guidewire 60 shown. In these embodiments, catheter 200 can be advanced over guidewire 60, such as by using standard over-the-wire techniques, through one or more lumens of catheter 200.

Console 100 can include one or more conduits, conduit 191 configured to transport fluid to and/or from console 100. Console 100 can include pump assembly 195 that includes one or more pumps or other fluid delivery mechanisms ("pump" herein) that deliver fluid (e.g. a liquid, a gas, and/or a gel) into one or more fluid pathways or other locations within catheter 200. Console 100 can include one or more reservoirs that store these fluids to be delivered. Alternatively or additionally, console 100 can be attachable to a fluid-storing reservoir separate from console 100 (or positioned in a second housing of console 100). Pump assembly 195 and/or another component of console 100 can include one or more pumps or other fluid removal mechanisms ("pump" herein) that extract fluid from one or more lumens or other locations within catheter 200. Console 100 can include one or more reservoirs that store these removed fluids, or they can be stored in a reservoir separate from console 100 (or positioned in a second housing of console 100). Pump assembly 195 and/or another component of console 100 can include one or more pumps or other vacuum generating mechanisms ("pump" herein) that generate a vacuum that can cause a negative pressure within one or more lumens or other locations within catheter 200.

Console 100 can comprise one or more discrete components, such as one or more components each with a discrete (i.e. separate) housing that surround one or more pumps and/or reservoirs.

In some embodiments, console 100 comprises vacuum supply 110. Vacuum supply 110 can comprise one or more pumps configured to generate a vacuum within catheter 200 and/or other component of system 10. In some embodiments, vacuum supply 110 includes one or more reservoirs configured to reduce variations in vacuum pressure. Vacuum supply 110 can provide a vacuum to one, two, three or more ports configured to engage tissue, such as tissue capture chambers 510 described herein. Vacuum supply 110 can be configured to provide a vacuum pressure of between −2 psi and −14.7 psi, such as between −4 psi and −14.7 psi. In some embodiments, system 10 can be configured to operate with vacuum supply 110 providing a vacuum pressure of between −6 psi and −12.5 psi. Additionally or alternatively, vacuum supply 110 and/or another component of console 100 can comprise at least one sensor, such as a sensor-based functional element 199, configured to monitor the pressure of vacuum supply 110, and provide an alert (e.g. an alert to the operator and/or enter a system wide alert mode) if the vacuum pressure is insufficient or otherwise undesired (e.g. if the vacuum pressure is above or below a desired level, an expected level, and/or other threshold). In some embodiments, a minimum vacuum threshold can comprise a threshold of at least −4.4 psi, at least −6 psi, and/or at least −12 psi. In some embodiments, vacuum supply 110 provides an aspiration reservoir, such as to remove a fluid from locations proximate the distal end of catheter 200 (e.g. gas or other fluid within the GI tract removed in a desufflation procedure and/or a fluid removed from a distal portion of catheter 200).

In some embodiments, console 100 comprises injectate fluid supply 120. Injectate supply 120 can comprise one or more pumps configured to deliver one or more injectates, injectate 125 shown, to catheter 200 and/or other component of system 10. In some embodiments, injectate supply 120 includes one or more reservoirs configured to store injectate 125. In some embodiments, injectate supply 120 comprises a pump (e.g. a syringe pump configured to drive 1, 2, 3 or more syringes simultaneously or sequentially), such as a pump that is part of pump assembly 195. In some embodiments, injectate supply 120 comprises injectate 125. Injectate supply 120 can deliver fluid to one, two, three or more elements configured to deliver injectate 125 onto and/or into tissue, such as injectate delivery elements 520 described herein. In some embodiments, a single syringe pump is configured to deliver fluid to two or more injectate delivery elements 520. Injectate supply 120 can be configured to deliver fluid at a flow rate of at least 10 mL/min, such as at a flow rate of at least 15 mL/min, 20 mL/min, 40 mL/min, 60 mL/min, or 120 mL/min. In some embodiments, injectate supply 120 delivers fluid via two or more injectate delivery elements 520 simultaneously (e.g. in a tissue expansion procedure), at a rate of at least 10 mL/min per injectate delivery element 520, such as at a rate of at least 12.5 mL/min, 15 mL/min, 20 mL/min, 40 mL/min, 60 mL/min, or 120 mL/min per fluid delivery element. In some embodiments, injectate supply 120 is configured to deliver a volume between 2 mL and 20 mL (e.g. approximately 10 mL) to multiple injectate delivery elements 520 simultaneously (e.g. two, three or four injectate delivery elements 520 simultaneously) in a time period less than 60 seconds, less than 40 seconds, less than 30 seconds, less than 20 seconds, less than 10 seconds, and/or less than 5 seconds (e.g. in a tissue expansion procedure). Injectate supply 120 can be further configured to deliver fluid (e.g. to injectate delivery elements 520, conduits 521, and/or another component of system 10) at a pressure of at least 40 psi, such as at a pressure of at least 75 psi, 100 psi, 200 psi, or 300 psi. Injectate supply 120 can be configured to provide a bolus of injectate 125 to two, three or more injectate delivery elements 520 (simultaneously or sequentially) in order to expand an axial segment of submucosal tissue (e.g. a full or partial circumferential band of submucosal tissue with a length of at least 0.25 cm, at least 0.5 cm, at least 0.75 cm, at least 1 cm, at least 2 cm, or at least 3 cm) to achieve an expansion of the submucosal layer to a thickness of at least 250 μm, at least 400 μm, or at least 650 μm (e.g. in the area surrounding the volume of mucosal tissue to be subsequently ablated).

Injectate 125 can comprise one or more liquids, gels, and/or other flowable materials for injecting into tissue, such as to expand one or more layers of tissue (e.g. submucosal tissue expanded prior to a mucosal ablation procedure) and/or to narrow a lumen of the intestine and/or other segment of the GI tract (e.g. to create a therapeutic restriction). Alternatively or additionally, injectate 125 can comprise an agent configured to cause tissue necrosis. Alternatively or additionally, injectate 125 can comprise a warming and/or cooling fluid delivered onto and/or into tissue (e.g. a neutralizing fluid such as neutralizing fluid 155 configured to limit, stop and/or at least reduce ablation performed by functional assembly 500). In some embodiments, injectate 125 comprises one, two or more materials selected from the group consisting of: a peptide polymer (e.g. a peptide polymer configured to stimulate fibroblasts to produce collagen); polylactic acid; polymethylmethacrylate (PMMA); a hydrogel; ethylene vinyl alcohol (EVOH); a material configured to polymerize EVOH; dimethyl sulfoxide (DMSO); saline; material harvested from a mammalian body; autologous material; fat cells; collagen; autologous collagen; bovine collagen; porcine collagen; bioengineered human collagen; dermis; a dermal filler; hyaluronic acid; conjugated hyaluronic acid; calcium hydroxylapatite; fibroblasts; a sclerosant; an adhesive; cyanoacrylate; a pharmaceutical agent; a visualizable material; a radiopaque material; a visible dye; ultrasonically reflective material; a combination of materials configured to cause an endothermic reaction when mixed (e.g. when mixed in tissue); a combination of materials configured to cause an exothermic reaction when mixed (e.g. when mixed in tissue); a combination of material configured to expand when mixed (e.g. when mixed in tissue); and combinations of one or more of these. In some embodiments, injectate 125 comprises beads (e.g. pyrolytic carbon-coated beads) suspended in a carrier (e.g. a water-based carrier gel). In some embodiments, injectate 125 comprises a solid silicone elastomer (e.g. heat-vulcanized polydimethylsiloxane) suspended in a carrier, such as a bio-excretable polyvinylpyrrolidone (PVP) carrier gel. In some embodiments, injectate 125 has an adjustable degradation rate, such as an injectate 125 comprising one or more cross linkers in combination with polyalkyleneimines at specific concentrations that result in hydrogels with adjustable degradation properties. In some embodiments, injectate 125 and/or agent 80 (e.g. as described herein) comprises living cells, such as living cells injected into the mucosa or submucosa of the intestine to provide a therapeutic benefit.

In some embodiments, injectate 125 comprises a visualizable and/or otherwise detectable (e.g. magnetic) material (e.g. in addition to one or more materials of above) selected from the group consisting of: a dye; a visible dye; indigo carmine; methylene blue; India ink; SPOT' dye; a visualizable media; radiopaque material; radiopaque powder; tantalum; tantalum powder; ultrasonically reflective material; magnetic material; ferrous material; and combinations of one or more of these.

In some embodiments, a volume of injectate 125 is delivered into tissue to create a therapeutic restriction (e.g. a therapeutic restriction with an axial length between 1 mm and 20 mm), as described herein, and/or as is described in applicant's co-pending U.S. patent application Ser. No. 17/095,108, entitled "Systems, Devices and Methods for the Creation of a Therapeutic Restriction in the Gastrointestinal Tract", filed Nov. 11, 2020. In some embodiments, a volume of injectate 125 is delivered into tissue to create a safety margin of tissue prior to an ablation procedure, as is described herein.

In some embodiments, injectate 125 comprises a fluorescent-labeled material or other biomarker configured to identify the presence of a biological substance, such as to identify diseased tissue and/or other tissue for treatment by functional assembly 500 (e.g. to identify target tissue). For example, injectate 125 can comprise a material configured to be identified by imaging device 70 (described below), such as to identify a visualizable change to injectate 125 that occurs after contacting one or more biological substances. In these embodiments, imaging device 70 can comprise a molecular imaging device, such as when imaging device 70 comprises a molecular imaging probe and injectate 125 comprises an associated molecular imaging contrast agent. In these embodiments, injectate 125 can be configured to identify diseased tissue and/or to identify a particular level of one or more of pH, tissue oxygenation, blood flow, and the like. Injectate 125 can be configured to be delivered onto the inner surface of intestinal or other tissue, and/or to be delivered into tissue (i.e. beneath the surface).

In some embodiments, console 100 comprises inflation fluid supply 130. Inflation fluid supply 130 can comprise one or more pumps configured to deliver one or more fluids, inflation fluid 135 shown, to inflate one or more portions of catheter 200 and/or other component of system 10. In some embodiments, inflation fluid supply 130 includes one or more reservoirs configured to store inflation fluid 135. In some embodiments, inflation fluid supply 130 comprises inflation fluid 135. Inflation fluid supply 130 can deliver inflation fluid 135 to a balloon or other reservoir (e.g. other fluid expandable component), such as expandable element 530 described herein. Inflation fluid supply 130 can be configured to deliver a bolus volume of fluid to expandable element 530, such as a bolus of between 0.1 mL and 12 mL, such as an operator selectable bolus volume of 6 mL, 8 mL, and/or 10 mL. Inflation fluid supply 130 can be configured to deliver fluid to expandable element 530 at a pressure of between 0.1 psi and 5 psi. In some embodiments, inflation fluid supply 130 delivers fluid to expandable element 530 prior to a tissue expansion procedure as described herein, in which a separate fluid, injectate 135, is delivered directly into submucosal or other tissue via one, two or more injectate delivery elements 520. In these embodiments, the fluid provided to expandable element 530 by inflation fluid supply 130 can comprise inflation fluid 135 and/or a different fluid, such as neutralizing fluid 155. Neutralizing fluid 155 can be delivered to expandable element 530 in a submucosal expansion procedure, such as to provide the additional function of pre-cooling or pre-warming tissue proximate element 530 prior to a subsequent thermal ablation procedure (e.g. a heat ablation or cryogenic ablation, respectively, performed by element 530). Alternatively or additionally, inflation fluid supply 130 can deliver neutralizing fluid 155 to element 530 in a tissue expansion procedure performed shortly after a (previous) ablation procedure, such as to perform a post-cooling and/or post-warming of tissue configured to limit the effects of a heat ablation or cryogenic ablation, respectively. For example, pre or post-cooling, and/or pre or post-warming can be performed to reduce time in a previous and/or subsequent ablation step.

In some embodiments, console 100 comprises ablative fluid supply 140. Ablative fluid supply 140 can comprise one or more pumps configured to deliver one or more ablative fluids, ablative fluid 145 shown, to one or more portions of catheter 200 and/or other component of system 10. In some embodiments, ablative fluid supply 140 includes one or more reservoirs configured to store ablative fluid 145. In some embodiments, ablative fluid supply 140 comprises ablative fluid 145. Ablative fluid supply 140 can deliver ablative fluid 145 to a balloon and/or other fluid storing assembly and/or component of catheter 200, such as an ablative fluid reservoir (e.g. a balloon), expandable element 540 and/or another expandable element 530 described herein. Alternatively or additionally, ablative fluid supply 140 can deliver ablative fluid 145 to one, two, three or more fluid delivery elements configured to deliver fluid onto and/or within tissue, such as injectate delivery elements 520 described herein. Ablative fluid supply 140 can be configured to deliver ablative fluid at a flow rate of at least 5 mL/s, such as at least 8 mL/s, 9 mL/s, 10 mL/s, 15 mL/s, and/or 20 mL/s. In some embodiments, catheter 200 comprises a hydraulic inflow resistance (resistance to ablative fluid supply 140 and/or another fluid supply described herein) of less than 0.05 psi/(mL/min), such as less than 0.036 psi/(mL/min) (e.g. when measured at 85° C. at a flow rate of 570 mL/min). In some embodiments, catheter 200 comprises a hydraulic inflow resistance of at least 0.020 psi/(mL/min), such as at least 0.030 psi/(mL/min) (e.g. when measured at 85° C. at a flow rate of 570 mL/min). In some embodiments, catheter 200 comprises a hydraulic outflow resistance less than 0.070 psi/(mL/min), such as less than 0.63 psi/(mL/min) (e.g. when measured at 85° C. at a flow rate of 570 mL/min). In some embodiments, catheter 200 comprises a hydraulic outflow resistance of at least 0.040 psi/(mL/min), such as at least 0.53 psi/(mL/min) (e.g. when measured at 85° C. at a flow rate of 570 mL/min). Additionally or alternatively, ablative fluid supply 140 can be configured to deliver ablative fluid at a pressure of approximately 40 psi (pressure leaving console 100), such that the pressure of the ablative fluid within expandable element 530 is approximately 20 psi. In some embodiments, ablative fluid supply 140 provides fluid at an ablative temperature (e.g. sufficiently hot or sufficiently cold temperature) in a recirculating manner.

In some embodiments, catheter 200 comprises an inflow pressure drop (e.g. a pressure drop due to flow resistance) of between 17 psi and 21 psi, such as when tested with a flow rate of 10 mL/s of water at 80° C. Additionally or alternatively, catheter 200 can comprise an inflow pressure drop of between 21 psi and 25 psi, such as when tested with a flow rate of 10 mL/s of water at 20° C. In some embodiments, the inflow pressure drop is no more than 50 psi, such as no more than 30 psi, such as no more than 20.5 psi. In some embodiments, the inflow pressure drop is at least 0.5 psi, such as at least 1 psi, such as at least 5 psi, such as at least 15 psi. In some embodiments, catheter 200 comprises a total pressure drop (e.g. a pressure drop due to the flow resistance throughout the entire fluid path) of between 30 psi and 40 psi, such as when tested with a flow rate of 10 mL/s of water at 80° C. Additionally or alternatively, catheter 200 can comprise a total pressure drop of between 39 psi and 50 psi, such as when tested with a flow rate of 10 mL/s of water at 20° C. In some embodiments the total inflow pressure drop is no more than 80 psi, such as no more than 60 psi, such as no more than 50 psi. In some embodiments, the total pressure drop is at least 1 psi, such as at least 5 psi, such as at least 15 psi, such as at least 30 psi, such as at least 35 psi.

In some embodiments, console 100 comprises neutralizing fluid supply 150. Neutralizing fluid supply 150 can comprise one or more pumps configured to deliver one or more neutralizing fluids, neutralizing fluid 155 shown, to one or more portions of catheter 200 and/or other component of system 10 (e.g. a fluid configured to neutralize ablative effects of an ablative fluid delivered by ablative fluid supply 140). In some embodiments, neutralizing fluid supply 150 includes one or more reservoirs configured to store neutralizing fluid 155. In some embodiments, neutralizing fluid supply 150 comprises neutralizing fluid 155. Neutralizing fluid supply 150 can deliver neutralizing fluid 155 to a balloon and/or other fluid storing assembly or component of catheter 200, such as a neutralizing fluid reservoir, expandable element 550, expandable element 540, and/or other expandable element 530 described herein. Alternatively or additionally, neutralizing fluid supply 150 can deliver neutralizing fluid 155 to one, two, three or more fluid delivery elements configured to deliver fluid onto and/or within tissue, such as injectate delivery elements 520 described herein. Neutralizing fluid supply 150 can be configured to deliver neutralizing fluid at a flow rate of at least 5 mL/s, such as at least 8 mL/s, 9 mL/s, 10 mL/s, 15 mL/s, or 20 mL/s. Additionally or alternatively, neutralizing fluid supply 150 can be configured to deliver neutralizing fluid at a pressure of approximately 40 psi (pressure leaving console 100), such that the pressure of the neutralizing fluid within expandable element 530 is approximately 20 psi. In some embodiments, neutralizing fluid supply 150 is configured to deliver neutralizing fluid 155 at a pressure of between 20 psi and 60 psi, such as between 30 psi and 50 psi. In some embodiments, neutralizing fluid 155 pressure is delivered at less than 100 psi. In some embodiments, ablative fluid 145 provided by ablative fluid supply 140 is delivered to a fluid storing component of catheter 200 (e.g. expandable element 530) and neutralizing fluid 155 provided by neutralizing fluid supply 150 is delivered onto and/or within tissue (e.g. via one or more injectate delivery elements 520). Alternatively or additionally, ablative fluid 145 provided by ablative fluid supply 140 can be delivered onto and/or within tissue (e.g. via one or more injectate delivery elements 520), while neutralizing fluid 155 provided by neutralizing fluid supply 150 is delivered to a balloon and/or other fluid storing assembly or component of catheter 200, such as expandable element 530, expandable element 540, and/or expandable element 550 described herein. In some embodiments, ablative fluid supply 140 comprises neutralizing fluid supply 150 (e.g. a single assembly comprising one or more pumps that provide both ablative fluid 145 and neutralizing fluid 155 from one, two or more reservoirs).

In some embodiments, inflation fluid supply 130, ablative fluid supply 140, neutralizing fluid supply 150 and/or another fluid delivery assembly of console 100 is configured to provide fluid (e.g. inflation fluid 135, ablative fluid 145 and/or neutralizing fluid 155) to functional assembly 500 (e.g. to one or more expandable elements 530) at a flow rate of at least 2 mL/sec, such as at least 5 mL/sec, or at a flow rate of approximately 9.5 mL/sec. In some embodiments, console 100 provides fluid to functional assembly 500 at a flow rate of no more than 30 mL/sec.

In some embodiments, console 100 comprises fluid removal pump 160. Fluid removal pump 160 can comprise one or more pumps configured to remove fluid from one or more portions of catheter 200 or other component of system 10. In some embodiments, fluid removal pump 160 includes one or more reservoirs configured to store the one or more removed fluids. In some embodiments, fluid removed by fluid removal pump 160 is recirculated to one or more other assemblies of console 100, such as inflation fluid supply 130, ablative fluid supply 140, neutralizing fluid supply 150, insufflation supply 170 (described herein) and/or functional fluid supply 180 (also described herein). Fluid removal pump 160 can remove fluid from a balloon or other fluid storing assembly or component of catheter 200, such as expandable element 530, expandable element 540, and/or expandable element 550 described herein. In some embodiments, fluid removal pump 160 is configured to remove (e.g. from catheter 200 and/or any component of system 10) injectate 125, inflation fluid 135, ablative fluid 145, neutralizing fluid 155, insufflation fluid 175, and/or functional fluid 185, each as described herein. In some embodiments, catheter 200 comprises a hydraulic outflow resistance as described herein in reference to ablation fluid supply 140. In some embodiments, ablative fluid supply 140 and/or neutralizing fluid supply 150 comprise fluid removal pump 160. In some embodiments, pump assembly 195 comprises fluid removal pump 160.

In some embodiments, console 100 comprises insufflation supply 170. Insufflation supply 170 can comprise one or more pumps configured to deliver a gas or other insufflation fluid, insufflation fluid 175 shown, to inflate the duodenum or other segment of the patient's GI tract. Alternatively or additionally, insufflation supply 170 can be configured to remove insufflation fluid 175 and/or other fluid from the duodenum or other segment of the patient's GI tract (i.e. perform a desufflation). In some embodiments, insufflation supply 170 includes one or more reservoirs configured to store insufflation fluid 175 (to be provided and/or recently removed). In some embodiments, insufflation supply 170 comprises insufflation fluid 175. Insufflation supply 170 can deliver and/or remove fluids via catheter 200 and/or a separate component of system 10, such as an endoscope or other body access device, endoscope 50.

In some embodiments, console 100 comprises functional fluid supply 180. Functional fluid supply 180 can provide functional fluid 185 to one or more components or assemblies of catheter 200 and/or other component of system 10. In some embodiments, functional fluid 185 comprises a hydraulic or pneumatic fluid ("hydraulic fluid" herein). In some embodiments, functional fluid 185 comprises a conductive fluid, such as a fluid configured to transmit electrical power and/or electrical signals between functional assembly 500 and console 100.

As described herein, console 100 can comprise one or more pumps, pump assembly 195. Pump assembly 195 can be configured to deliver and/or extract fluids from catheter 200 (e.g. with or without an intermediate connection device such as umbilical 600 described herein). In some embodiments, pump assembly 195 is fluidly attached to at least injectate supply 120 and/or inflation supply 130, such as to supply injectate 125 and/or inflation fluid 135, respectively, to catheter 200. In some embodiments, pump assembly 195 is fluidly attached to injectate supply 120, inflation fluid supply 130, ablative fluid supply 140, neutralizing fluid supply 150, insufflation supply 170, and/or functional fluid supply 180, such as to deliver and/or remove their associated fluids to and/or from catheter 200. In some embodiments, one or more of injectate supply 120, inflation fluid supply 130, ablative fluid supply 140, neutralizing fluid supply 150, insufflation supply 170, and/or functional fluid supply 180 comprise one or more pumps integrated into their assembly (e.g. one or more pumps of pump assembly 195 are integrated into the supply). In some embodiments, pump assembly 195 is configured as described herebelow in reference to FIG. 1A.

Console 100 comprises one or connectors, connector 102 shown, which fluidly connects to one or more of assemblies 110, 120, 130, 140, 150, 160, 170, and/or 180 of console 100 described herein, via conduits 111, 121, 131, 141, 151, 161, 171, and/or 181, respectively. In some embodiments, console 100 comprises pump assembly 195, which fluidly connects conduits 111, 121, 131, 141, 151, 161, 171, and/or 181 to connector 102 via one or more other conduits, such as conduit 191 shown. Alternatively or additionally, console 100 can comprise one or more manifolds, manifold 700*a* shown, which fluidly connects conduits 111, 121, 131, 141, 151, 161, 171, and/or 181 to connector 102 via one or more other conduits, such as conduit 191 shown. Alternatively, conduits 111, 121, 131, 141, 151, 161, 171, and/or 181 directly attach to connector 102 (i.e. without pump assembly 195 and/or without manifold 700*a*). Manifold 700*a* can be constructed and arranged to fluidly combine one or more of conduits 111, 121, 131, 141, 151, 161, 171 and/or 181. Alternatively or additionally, manifold 700*a* can be constructed and arranged to split (divide) one or more of conduits 111, 121, 131, 141, 151, 161, 171, and/or 181 into multiple conduits. In some embodiments, manifold 700*a* includes one or more valves configured to control flow of fluid in a conduit. In some embodiments, manifold 700*a* includes one or more sensors (e.g. temperature and/or pressure sensors) configured to provide a signal related to a parameter (e.g. temperature and/or pressure) of fluid within a conduit.

In some embodiments, system 10 comprises a connecting device, umbilical 600 which operably connects (e.g. at least fluidly connects) catheter 200 to console 100. Alternatively or additionally, catheter 200 can attach directly to console 100 (e.g. connector 102 of console 100 attaches directly to connector 302 of catheter 200). Umbilical 600 comprises one or more proximal connectors, connector 602*a* shown, which operably attaches to mating connector 102 of console 100. Umbilical 600 comprises one or more distal connectors, connector 602*b* shown, which operably attaches to mating connector 302 of handle assembly 300 of catheter 200. Umbilical 600 can comprise one or more fluid delivery tubes or other fluid-transporting conduits, conduit 691 shown. Conduit 691 comprises one or more lumens or other conduits configured to allow passage of one or more similar and/or dissimilar fluids between console 100 and catheter 200. Each conduit can be configured to receive one or more shafts or other conduits which transport one or more fluids. In some embodiments, umbilical 600 further comprises one or more of: wires or other electrical filaments configured to transmit electrical power and/or signals; optical fibers or other conduits configured to transmit optical power and/or signals; waveguides or other sound conduits configured to transmit sonic power and/or signals; mechanical linkages (e.g. translatable rods); and/or other elongate structures configured to transmit energy, signals, and/or mechanical motion between console 100 and catheter 200. In some embodiments, umbilical 600 comprises one or more sensors, transducers, and/or other functional elements, such as functional element 699 described herein. Functional element 699 can be positioned proximate conduit 691 as shown, positioned proximate connector 602*a*, and/or positioned proximate connector 602*b*. In some embodiments, umbilical 600 comprises one or more insulating layers, insulating conduits, and/or other insulating materials, such as to prevent heat loss when a heated fluid is passed through a lumen of umbilical 600. In some embodiments, functional element 699 comprises a heating element configured to heat fluid as it enters and/or exits umbilical 600. For example, functional element 699 can comprise a heating element and a temperature sensor, and system 10 can be configured to heat the fluid exiting umbilical 600 to a desired temperature, such as in a closed-loop manner. In some embodiments, one or more conduits of umbilical 600 are manufactured such that one or more dimensions of umbilical 600 (e.g. at least the overall length) are provided to a user within a tolerance of no more than 10% variance, such as no more than 5%, or no more than 3% variance.

Catheter 200, including distal portion 208 and distal end 209, comprises handle assembly 300, shaft assembly 400, and functional assembly 500. Handle assembly 300 is positioned on the proximal end or at least a proximal portion of shaft assembly 400, and functional assembly 500 is positioned on catheter 200 distal portion 208 (e.g. on the distal end or at least a distal portion of shaft assembly 400).

Shaft assembly 400 includes at least one elongate shaft, shaft 401, which comprises one or more lumens or other conduits, conduit 491, each of which can be configured to attach to one or more conduits of handle 300, conduit 391. In some embodiments, one or more conduits of conduit 491 simply passes through handle 300 (e.g. to operably attach to umbilical 600 and/or console 100). Each conduit of shaft 401 can be configured to transport fluid and/or it can be sized to receive (e.g. slidingly receive) one or more separate shafts, such as one or more shafts that transport fluid. In some embodiments, on or more lumens of shaft 401 receive a separate shaft, and fluid is transported within the received shaft and/or between the outer diameter of the received shaft and the wall of the lumen of shaft 401, such as is described herein. Alternatively or additionally, each lumen of shaft 401 and/or one or more shafts inserted within the lumen can surround (e.g. slidingly or fixedly surround) one or more conduits configured to transmit energy, signals, and/or mechanical motion between console 100 and catheter 200, as described herein. In some embodiments one or more conduits 491 are fixedly attached within shaft 401 with adhesive, such as with one or more rings of adhesive positioned about the outer wall of a conduit 491 and a surrounding wall (e.g. the inner wall of a sleeve, lumen, or other tube) onto which conduit 491 is to be fixedly attached. For example, two or more rings of adhesive can be positioned between the outer wall of a conduit 491 and a surrounding wall (e.g. a surrounding wall of a sleeve) to prevent undesired translation of the conduit 491.

Shaft assembly 400 comprises proximal end 405, proximal portion 406, middle portion 407, distal portion 408, and distal end 409. Distal portion 408 is shown in a magnified view. Positioned on distal portion 408 is functional assembly

500, configured as a treatment assembly and/or diagnostic assembly (e.g. an assembly configured to treat and/or diagnose tissue of the intestine or other GI tract tissue). In some embodiments, shaft 401 extends through and beyond functional assembly 500 (as shown in FIG. 1, where catheter 200 distal end 209 is the same as shaft assembly 400 distal end 409). Alternatively, functional assembly 500 can be positioned on the distal end of shaft 401. In some embodiments, shaft 401 comprises a twist, such as is described herebelow in reference to FIG. 4. In some embodiments, shaft 401 comprises a bulbous tip. In some embodiments, shaft 401 comprises a tapered tip, such as is described herebelow in reference to FIGS. 3A and 3B.

In some embodiments, shaft assembly 400 comprises a lumen to slidingly receive a guidewire, such as a passageway including a lumen which exits at a location proximate the distal end 409 of shaft assembly 400 at an opening, port 490. In some embodiments, shaft assembly 400 comprises one or more lumens for performing insufflation and/or desufflation ("insufflation" herein), such as conduit 571 comprising one or more lumens which terminate in one or more openings, such as port 470D positioned distal to functional assembly 500 and port 470_P positioned proximal to functional assembly 500, each as shown and described herein. In some embodiments, port 470_P and/or port 470D is configured to perform desufflation only, or insufflation only.

In some embodiments, shaft assembly 400 comprises one or more manifolds, manifold 700c and/or 700d shown, which fluidly connects one or more conduits of conduit 491 to one or more other conduits (e.g. one or more other conduits of conduit 491 or one or more other conduits of catheter 200). Manifolds 700c and/or 700d can be constructed and arranged to fluidly combine one or more of lumens of conduit 491. Alternatively or additionally, manifolds 700c and/or 700d can be constructed and arranged to split (divide) one or more of lumens of conduit 491 into multiple lumens. In some embodiments, manifolds 700c and/or 700d includes one or more valves (e.g. one or more one-way valves) configured to control flow of fluid in a conduit. In some embodiments, manifolds 700c and/or 700d includes one or more sensors (e.g. temperature and/or pressure sensors) configured to provide a signal related to a parameter (e.g. temperature and/or pressure) of fluid within a conduit.

In some embodiments, shaft assembly 400 comprises one or more sensors, transducers, and/or other functional elements, such as functional element 499a (e.g. positioned in a mid-portion of shaft 401 and/or proximate manifold 700c) and/or functional element 499b (e.g. positioned proximate manifold 700d and/or functional assembly 500) as shown and described herein. In some embodiments, functional element 499a and/or 499b comprises a radiopaque marker and/or other visualizable marker, as described herein, configured to allow an operator to visualize translation and/or rotation of shaft assembly 400 (e.g. to visualize translation and/or rotation of functional assembly 500), such as via imaging device 70 (e.g. a fluoroscope or other imaging device).

Shaft 401 can comprise a length of at least 60", such as at least 72". In some embodiments, shaft 401 comprises an outer diameter of less than 0.3", such as a diameter less than 0.256", 0.1", or 0.08". Shaft 401 can comprise a material selected from the group consisting of: a polyether block amide such as Pebax™; a thermoplastic elastomer, such as Tygon™, Arnitel™, or Hytrel™; and combinations of one or more of these. In some embodiments, at least a portion of shaft 401 comprises a radiopaque additive, such as barium sulfate. In some embodiments, at least a portion of shaft 401 comprises a lubricious coating or additive, such as Propell™ low friction compound manufactured by Foster Corporation of Putnam, CT. In some embodiments, at least a portion of shaft 401 comprises a heat stabilizer, a light stabilizer, and/or other stabilizing agent, such as an HLS™ heat and light stabilizer manufactured by the Foster Corporation of Putnam, CT.

Functional assembly 500 comprises one or more assemblies configured to treat and/or diagnose tissue. In some embodiments, functional assembly 500 is configured to both treat and diagnose tissue. Functional assembly 500 can be configured to treat and/or diagnose duodenal tissue or other tissue of the GI tract. Functional assembly 500 can be positioned on distal portion 408 of shaft assembly 400 as shown. Functional assembly 500 can be configured to radially expand and/or radially contract, such as when functional assembly comprises one or more expandable reservoirs, such as one or more of expandable elements 530, 540 and/or 550 shown (singly or collectively, expandable element 530). Each expandable element 530, 540 and/or 550 (singly or collectively expandable element 530) can comprise a balloon or other expandable reservoir ("balloon" herein), an expandable cage, a furlable element, and the like. Expandable element 530 can comprise one or more balloons that circumferentially surround shaft 401 (e.g. in a linear arrangement), or multiple partially circumferential balloons (e.g. in a radial arrangement). Expandable elements 530 can comprise one or more balloons that expand radially out from shaft 401, at the same or different axial locations along shaft 401. An expandable element 530 can comprise an array of balloons in a lobed configuration, circumferentially spaced. An expandable element 530 can comprise one or more inner balloons 540 surrounded by one or more outer balloons 550 (e.g. where the inner balloon receives a first fluid at a first temperature and the space between the inner and outer balloons receives a second fluid at a second temperature, different than the first temperature). Expandable element 530 can comprise a balloon or other element configured to expand to a diameter of less than or equal to 35 mm, such as less than or equal to 30 mm or 25 mm. Expandable element 530 can comprise a material as described herein. Expandable element 530 can comprise a balloon with a wall thickness as described herein. In some embodiments, one or more portions of expandable element 530 comprise a non-compliant material and one or more other portions of expandable element 530 comprises a compliant material. In some embodiments, expandable element 530 is configured to withstand an inflation pressure of up to 50 psi, such as up to 60 psi, 100 psi, or 200 psi. In some embodiments, a first expandable element 530 comprises at least a portion comprising a non-compliant material and a second expandable element 540 comprises at least a portion comprising a compliant material.

Functional assembly 500 can comprise one or more balloons configured to receive one or more fluids, such as an expandable element 540 configured to receive an ablative fluid (e.g. a fluid at an ablative temperature received from ablative fluid supply 140), an expandable element 550 configured to receive a neutralizing fluid (e.g. a fluid received from neutralizing fluid supply 150 and comprising a temperature configured to cool or warm tissue after a heat or cryogenic ablation, respectively), or other expandable element 530. In some embodiments, at least expandable element 540 and expandable element 550 are the same reservoir (e.g. the same one or more balloons) that receive both ablative fluid and neutralizing fluid.

In some embodiments, functional assembly 500 is configured to expand one or more layers of tissue, such as to expand one or more layers of submucosal tissue prior to a tissue treatment procedure in which a mucosal layer of tissue is treated (e.g. thermally or chemically ablated). In these embodiments, functional assembly 500, catheter 200 and/or any component of system 10 can be of similar construction and arrangement to that described in: applicant's co-pending U.S. patent application Ser. No. 14/515,324, entitled "Tissue Expansion Devices, Systems and Methods", filed Oct. 15, 2014; applicant's co-pending U.S. patent application Ser. No. 17/095,108, entitled "Systems, Devices and Methods for the Creation of a Therapeutic Restriction in the Gastrointestinal Tract", filed Nov. 11, 2020; and applicant's co-pending U.S. patent application Ser. No. 17/110,720, entitled "Injectate Delivery Devices, Systems and Methods", filed Dec. 3, 2020.

In some embodiments, functional assembly 500 is configured to receive an ablative fluid (e.g. a recirculating hot or cold fluid at a tissue-ablating temperature) to treat tissue. In some embodiments, functional assembly 500 is configured to deliver an ablation fluid directly onto tissue (e.g. a hot or cold liquid or gas at a tissue-ablating temperature, and/or a chemically ablative fluid). In these embodiments, functional assembly 500, catheter 200 and/or any component of system 10 can be of similar construction and arrangement to that described in: applicant's co-pending U.S. patent application Ser. No. 16/438,362, entitled "Heat Ablation Systems, Devices and Methods for the Treatment of Tissue", filed Jun. 11, 2019 and applicant's co-pending U.S. patent application Ser. No. 14/917,243, entitled "Systems, Methods and Devices for Treatment of Target Tissue", filed Mar. 7, 2016.

Functional assembly 500 can include one or more ports configured to capture and/or engage tissue (singly or collectively "capture" or "engage" herein) or otherwise stabilize functional assembly 500 within a GI lumen, such as tissue capture chambers 510 shown and described herein. Each tissue capture chamber 510 includes an opening, opening 512. In some embodiments, functional assembly 500 (or another portion of catheter 200) includes two, three, four or more tissue capture chambers 510. Each tissue capture chamber 510 can be attached to a source of vacuum, such as conduit 511 which is fluidly attached to a source of vacuum provided by console 100, such as vacuum supply 110. Each tissue capture chamber 510 can be of similar construction and arrangement to any chamber 510 described herein. In some embodiments, injectate delivery element 520 is positioned above (radially out from) a source of vacuum that is provided to tissue capture chamber 510. In some embodiments, one or more tissue capture chambers 510 is constructed of a metal or other material with a relatively high thermal conductance, such as to efficiently transfer heat from and/or to expandable element 530 (e.g. from and/or to temperature-ablative fluid within expandable element 530), such as to avoid non-ablated tissue regions proximate tissue capture chambers 510.

Functional assembly 500 can comprise one or more elements configured to deliver fluid into tissue, such as injectate delivery elements 520 shown, each positioned within or at least proximate a tissue capture chamber 510. In some embodiments, functional assembly 500 (or another portion of catheter 200) includes two, three, four or more injectate delivery elements 520. Injectate delivery elements 520 can comprise one or more elements selected from the group consisting of: needle; fluid jet; iontophoretic element; and combinations of one or more of these. Each injectate delivery element 520 can be operably attached to one or more conduits of catheter 200, such when fluidly connected to conduit 521 shown or when fluidly attached to a separate conduit slidingly received by conduit 521 as described herein. Each injectate delivery element 520 can be connected to a source of fluid, such as a fluid provided by console 100 via injectate supply 120, ablative fluid supply 140, neutralizing fluid supply 150, and/or functional fluid supply 180. One or more injectate delivery elements 520 can comprise a needle with a diameter between 16 gauge and 34 gauge, such as a needle with a 27 gauge or 29 gauge diameter One or more injectate delivery elements 520 can comprise a needle with a bevel angle of approximately 10° (e.g. with a bevel length of 0.008"), such as a bevel angle of at least 5° and/or a bevel angle no more than 45° or no more than 80°. One or more injectate delivery elements 520 can be advanced into the tissue contained in the associated tissue capture chambers 510, while avoiding the potential of the injectate delivery elements 520 penetrating an outer layer and/or outside of the GI wall tissue (e.g. injectate delivery elements 520 do not exit chambers 510). In some embodiments, tissue is penetrated by a needle-based injectate delivery element 520 at the time of the application of the vacuum to chamber 510, without the advancement of injectate delivery elements 520 (e.g. when the distal end of each injectate delivery element 520 is positioned within the associated chamber 510). In some embodiments, one or more injectate delivery elements 520 comprises a fluid jet, and injectate 125 or other fluid can be delivered into tissue captured within chamber 510 without advancement of the fluid jet. Each tissue capture chamber 510 can be configured to slidingly receive an injectate delivery element 520 (e.g. at a time in which tissue is captured within chamber 510 and the injectate delivery element 520 penetrates the captured tissue upon advancement), such as when a tissue capture chamber 510 is configured to slidingly receive at least a 29 gauge needle, or at least a 27 gauge needle. Each injectate delivery element 520 can be configured to be advanced a distance of at least 2.5 mm, at least 3.5 mm, or at least 4.5 mm. Each tissue capture chamber 510 can comprise a width of at least 0.010", at least 0.040" or at least 0.060". Each tissue capture chamber 510 can comprise a width of no more than 0.25", or no more than 0.35". Each tissue capture chamber 510 can comprise a length of at least 0.010", at least 0.040" at least 0.060", at least 0.090", or at least 0.120". Each tissue capture chamber 510 can comprise a length of no more than 0.9", no more than 0.7", or no more than 0.5". Each tissue capture chamber 510 can comprise a depth of at least 300 μm, at least 500 μm, at least 700 μm, or at least 1000 μm. Each tissue capture chamber 510 can comprise a depth of no more than 2500 μm, such as no more than 2000 μm.

Functional assembly 500 of FIG. 1 can comprise two tissue capture chambers 510 (e.g. separated circumferentially at approximately 180°) or three tissue capture chambers 510 (e.g. separated circumferentially at approximately 120°), and each can surround an injectate delivery element 520. In some embodiments, four or more tissue capture chambers 510 are included. Each tissue capture chamber 510 can be configured to engage with tissue, such as to maintain contact between functional assembly 500 and tissue (e.g. during delivery and/or removal of energy to and/or from tissue). Alternatively or additionally, tissue capture chamber 510 can be configured to capture tissue within tissue capture chamber 510, via application of a vacuum, as described herein, such as to allow delivery of fluid or a fluid delivery element (e.g. a needle) into the captured tissue.

Functional assembly 500 can comprise one or more ports (e.g. openings) in shaft assembly 400 that are configured to deliver fluid into and/or remove fluid from expandable element 530, such as ports 430 and 460 shown. Ports 430 and 460 can be positioned in various locations within expandable element 530. In some embodiments, port 460 is configured to remove fluid from expandable element 530, and is positioned in a proximal portion of functional assembly 500. In some embodiments, port 430 is configured to deliver fluid into expandable element 530, and can be positioned in a distal (as shown), middle or proximal portion of functional assembly 500. Port 430 can comprise one or more openings which are fluidly attached to one or more conduits, such as conduits 531, 541, and/or 551 as shown, which are fluidly connected to one or more of inflation fluid supply 130, ablative fluid supply 140 and/or neutralizing fluid supply 150, respectively, or other fluid supply of console 100 (e.g. functional fluid supply 180). Port 460 can comprise one or more openings fluidly connected to one or more conduits, such as conduit 561 as shown, which is fluidly connected to fluid removal pump 160 of console 100. In some embodiments, port 460 is fluidly attached to conduits 531, 541, and/or 551, which are fluidly connected to one or more of inflation fluid supply 130, ablative fluid supply 140 and/or neutralizing fluid supply 150, respectively, or other fluid supply of console 100 (e.g. functional fluid supply 180).

In some embodiments, functional assembly 500 comprises one or more sensors, transducers, and/or other functional elements, such as functional element 599 shown and described herein. In some embodiments, functional element 599 comprises a radiopaque marker and/or other visualizable marker, as described herein, configured to allow an operator to visualize translation and/or rotation of functional assembly 500, such as via imaging device 70 (e.g. a fluoroscope or other imaging device). In some embodiments, functional element 599 comprises a heat-generating transducer, such as an element comprising one, two, or more electrodes through which radiofrequency (RF) energy is passed, such as to heat expandable element 530, 540, and/or 550, and/or to heat fluid (e.g. saline) contained within expandable element 530, 540, and/or 550. Alternatively or additionally, functional element 599 can comprise a cooling transducer (e.g. a Peltier cooling element), such as to cool expandable element 530, 540, and/or 550, and/or to cool fluid contained within expandable element 530, 540, and/or 550.

Handle assembly 300 comprises a handle for an operator to manipulate catheter 200, including housing 301. Handle assembly 300 can be positioned in proximal end 405 of shaft assembly 400 as shown. Handle assembly 300 comprises one or more conduits, conduit 391. Conduit 391 can be configured to operably attach (e.g. on its proximal end or ends) to connector 102 of console 100 or to conduit 691 of umbilical 600. Conduit 391 is configured to operably attach (e.g. on its distal end or ends) to conduit 491 of shaft assembly 400. In some embodiments, handle assembly 300 comprises one or more manifolds, manifold 700b shown, which fluidly connects one or more conduits of conduit 391 to one or more other conduits (e.g. one or more other conduits of conduit 391 and/or conduit 491). Manifold 700b can be constructed and arranged to fluidly combine one or more of lumens of conduit 391. Alternatively or additionally, manifold 700b can be constructed and arranged to split one or more of lumens of conduit 391 into multiple lumens. In some embodiments, manifold 700b includes one or more valves configured to control flow of fluid in a conduit. In some embodiments, manifold 700b includes one or more sensors (e.g. temperature and/or pressure sensors) configured to provide a signal related to a parameter (e.g. temperature and/or pressure) of fluid within a conduit.

Handle assembly 300 can include one or more controls, control 310, which can be configured to activate, manipulate and/or otherwise operate one or more functions of catheter 200. In some embodiments control 310 comprises a control for advancing and/or retracting one or more injectate delivery elements 520 (e.g. simultaneously advancing and/or retracting two, three or more injectate delivery elements 520). In some embodiments, control 310 is configured to adjust one or more operating parameters of console 100 (e.g. via a wired or wireless connection).

Handle assembly 300 can include an entry port, such as port 392, for passage of a guidewire or other filament, such as guidewire 60. In some embodiments, port 392 is positioned on a proximal portion of shaft assembly 400. Port 392 can be operably connected to a lumen of shaft 401, such as is described herein.

In some embodiments, handle assembly 300 comprises one or more sensors, transducers, and/or other functional elements, such as functional element 399 shown and described herein. In some embodiments, functional element 399 comprises a tactile transducer configured to alert an operator of a particular state of catheter 200 (e.g. an alarm or warning state, a "ready" state, a "function completed" state, and the like). For example, functional element 399 can alert an operator that a particular function is being performed, such as a function selected from the group consisting of: heating of tissue is being performed (e.g. via hot fluid present in functional assembly 500); a cooling of tissue is being performed (e.g. via cold fluid present in functional assembly 500); injectate is being delivered into tissue (e.g. injectate 125 is being delivered into submucosal or other tissue via one, two, three or more injectate delivery elements 520); needles or other injectate delivery elements 520 have been advanced into tissue; and combinations of one or more of these. Functional element 399 can comprise a tactile transducer selected from the group consisting of: a vibrational transducer (e.g. a vibrational transducer that alerts an operator that injectate is being delivered into tissue and/or injectate delivery elements 520 are presently advanced into tissue); a heating element (e.g. a heating element that alerts an operator that a heat ablation and/or warming of tissue is in process); a Peltier element or other cooling element (e.g. a cooling element that alerts an operator that a cryogenic ablation and/or cooling of tissue is in process); and combinations of one or more of these. In some embodiments, handle assembly 300 includes a portion configured to alert an operator of one or more particular functional states of catheter 200.

One or more functional elements can be included in system 10, such as functional element 199 of console 100, functional element 399 of handle assembly 300, functional element 499a and/or 499b of shaft assembly 400, functional element 599 of functional assembly 500, and/or functional element 699 of umbilical 600.

Endoscope 50 can comprise one or more endoscopes configured to reach at least one or more portions of the duodenum from the patient's mouth. In some embodiments, endoscope 50 comprises an endoscope similar to Olympus model number PCF-PH190.

Guidewire 60 can comprise an outside diameter of approximately 0.035". Guidewire 60 can comprise a "stiff" or "super stiff" configuration, such as a guidewire similar to a Jagwire Stiff Straight guidewire, a Wallstent Super Stiff guidewire, a Dreamwire Superstiff, and/or a Savary Gilliard guidewire. Guidewire 60 can comprise a length of at least twice the length of catheter 200 and/or endoscope 50, such that one or more devices can be "exchanged" over guidewire 60. Guidewire 60 can comprise a material selected from the group consisting of: nitinol; stainless steel; and combinations of one or more of these. Guidewire 60 can comprise a hydrophilic or other lubricious coating, such as a Teflon coating.

In some embodiments, system 10 further comprises imaging device 70, which can comprise an imaging device constructed and arranged to provide an image of the patient's anatomy (e.g. inner wall or any part of the intestine of the patient) and/or an image of all or part of catheter 200 or other portion of system 10, as described in detail herein. Imaging device 70 can comprise an imaging device selected from the group consisting of: endoscope camera; visible light camera; infrared camera; X-ray imager; fluoroscope; CT Scanner; MRI; PET Scanner; ultrasound imaging device; molecular imaging device; and combinations of one or more of these. In some embodiments, a patient image is used to set, confirm and/or adjust one or more system 10 parameters, such as when imaging device 70 comprises a sensor of the present inventive concepts configured to produce a signal.

In some embodiments, system 10 further comprises one or more agents, agent 80 shown. Agent 80 can be delivered by one or more components of system 10, such as by endoscope 50 (via one or more working channels of endoscope 50) and/or by catheter 200 (e.g. via one or more injectate delivery elements 520 or ports 470). Agent 80 can comprise a material selected from the group consisting of: anti-peristaltic agent, such as L-menthol (i.e. oil of peppermint); glucagon; buscopan; hyoscine; somatostatin; a diabetic medication; an analgesic agent; an opioid agent; a chemotherapeutic agent; a hormone; and combinations of one or more of these. In some embodiments, agent 80 comprises cells delivered into the intestine, such as living cells delivered into intestinal mucosa or submucosa via one or more injectate delivery elements 520. In some embodiments, agent 80 comprises one or more agents configured to be delivered into expandable element 530 and to pass through at least a portion of expandable element 530 and into the intestine (e.g. when expandable element 530 comprises at least a portion that is porous). In some embodiments, agent 80 comprises a mucolytic agent configured to remove mucus from a tissue surface.

In some embodiments, system 10 comprises a tissue marker, marker 90 shown, which can comprise a dye or other visualizable media configured to mark tissue (e.g. a dye delivered using a needle-based tool, and/or a visualizable temporary implant used to mark tissue, such as a small, temporary anchor configured to be attached to tissue and removed at the end of the procedure or otherwise passed by the natural digestive process of the patient shortly after procedure completion). Marker 90 can be deposited or deployed in reference to (e.g. to allow an operator to identify) non-target tissue (e.g. a marker positioned proximate the ampulla of Vater to be visualized by an operator to avoid damage to the ampulla of Vater), and/or to identify target tissue (e.g. tissue to be ablated). In some embodiments, marker 90 is deposited or deployed in reference to tissue selected from the group consisting of: gastrointestinal adventitia; duodenal adventitia; the tunica serosa; the tunica muscularis; the outermost partial layer of the submucosa; ampulla of Vater; pancreas; bile duct; pylorus; and combinations of one or more of these.

Shaft 401 can comprise at least six lumens, at least eight lumens, or at least ten lumens. In some embodiments, shaft 401 comprises a single shaft comprising the at least six lumens or at least eight lumens. In these embodiments, a first pair of lumens of shaft 401 can be in fluid communication with a first tissue capture chamber 510, a second pair of lumens of shaft 401 can be in fluid communication with a second tissue capture chamber 510; and a third pair of lumens of shaft 401 can be in fluid communication with expandable element 530 (e.g. via openings in shaft 401, ports 430 and 460). The first pair of lumens of shaft 401 can comprise a vacuum lumen and a lumen that slidingly receives a first tube attached to a first injectate delivery element 520. The second pair of lumens of shaft 401 can comprise a vacuum lumen and a lumen that slidingly receives a second tube attached to a second injectate delivery element 520. The third pair of lumens of shaft 401 can comprise a fluid delivery lumen that delivers fluid to expandable element 530 and a fluid removal lumen that removes fluid from expandable element 530 (e.g. via ports 430 and 460, respectively), as described herein. In some embodiments, the at least one flexible elongate shaft comprises at least eight lumens, and a fourth pair of lumens are in fluid communication with a third tissue capture chamber 510. In some embodiments, shaft 401 further comprises, as described herein, one or more of: a guidewire lumen; a first insufflation lumen; and/or a second insufflation lumen. In some embodiments, shaft 401 comprises multiple shafts, such as two shafts 401 that each include at least a pair of lumens, or three shafts 401 that each include at least a pair of lumens.

In some embodiments, shaft 401 comprises a first lumen for delivering fluid to expandable element 530 (e.g. delivering to element 530 one or more of: inflation fluid 135, ablative fluid 145 and/or neutralizing fluid 150), and a second lumen for removing fluid from expandable element 530 (e.g. removing from element 430 one or more of inflation fluid 135, ablative fluid 145 and/or neutralizing fluid 155). In some embodiments, shaft 401 comprises two, three or more lumens configured to provide and remove fluid from expandable element 530 in a recirculating manner.

Expandable element 530, 540 and/or 550 (singly or collectively expandable element 530) can comprise various materials and dimensions that are configured to optimize the performance of one or more functions, such as submucosal tissue expansion (e.g. duodenal submucosal tissue expansion), mucosal tissue treatment (e.g. duodenal mucosal tissue ablation or other treatment), and/or substance delivery (e.g. delivery of one or more substances into the mucosa, submucosa, and/or other luminal wall location of the duodenum, jejunum, ileum, and/or other GI wall location). In some embodiments, expandable element 530 comprises a diameter (e.g. an expanded diameter of a balloon-based expandable element 530) of at least 5 mm and/or of no more than 45 mm, such as a diameter of at least 18 mm and/or of no more than 32 mm, such as a diameter of at least 23.5 mm and/or no more than 26.5 mm, such as a diameter of approximately 24 mm or 25 mm. In some embodiments, expandable element 530 comprises a balloon with a wall thickness (e.g. thickness of a single wall of the balloon) of at least 0.0001 in and/or of no more than 0.01 in, such as a wall thickness of at least 0.00025 in and/or no more than 0.003 in, such as a wall thickness of at least 0.0005 in and/or no more than 0.001 in, such as a wall thickness of approximately 0.00075 in. In some embodiments, expandable element 530 comprises a balloon with varied wall thickness, such as wall thickness that varies and has a thickness of at least 0.00025 in and/or no more than 0.003 in. For example, expandable element 530 can comprise an increased wall thickness proximate tissue capture cambers 510. In some embodiments, expandable element 530 comprises a material selected the group consisting of: a compliant material; a non-compliant material; both a compliant and a non-compliant material; PET; polyimide; nylon; nylon 12; PEEK; a silicone elastomer; polyether block amide; a polyurethane; a thermoplastic elastomer; and combinations thereof. In some embodiments, expandable element 530 comprises a balloon manufactured using a non-compliant material that prevents or at least resists geometric changes (e.g. the expanded diameter of the balloon) due to pressure variations within the balloon (e.g. pressure changes that may occur while fluid is recirculated within the balloon). In some embodiments, expandable element 530 (e.g. a balloon-based expandable element 530) comprises a compliance of at least 0.0001% and/or no more than 200%, such as a compliance of at least 0.0001% and/or no more than 15%, such as a compliance between at least 0.0001% and/or no more than 8%. In some embodiments, expandable element 530 comprises one or more materials with a thermal conductivity (W/(m*K)) of at least 0.01 and/or nor more than 10, such as a thermal conductivity of at least 0.1 and/or no more than 0.6, such as a thermal conductivity of approximately 0.29. In some embodiments, expandable element 530 comprises a contact length (e.g. a length of expandable element 530 in contact with duodenal or other luminal wall tissue when inflated or otherwise expanded) of at least 5 mm and/or no more than 500 mm, such as a contact length of at least 10 mm and/or no more than 50 mm, such as a contact length of at least 19 mm and/or no more than 21 mm, such as a contact length of approximately 20 mm. In some embodiments, expandable element 530 (e.g. an inflated balloon-based expandable element 530) comprises a tapered proximal and/or distal end, such as a tapered end with a taper angle (e.g. a proximal and/or distal taper angle) of at least 5° and/or no more than 120°, such as a taper angle of at least 30° and/or no more than 90°, such as a taper angle of at least 57° and/or no more than 63°, such as a taper angle of approximately 60°. Expandable element 530 can comprise proximal and distal tapers that are similar or dissimilar. In some embodiments, expandable element 530 comprises a balloon which includes a braid on and/or within its wall, such as a metal braid and/or non-metal braid (e.g. a nylon braid).

Injectate delivery elements 520 can comprise one or more needles or other fluid delivery elements as described herein. Injectate delivery elements 520 can comprise one or more needles or other fluid delivery elements that are configured to deliver fluid or other material to tissue to perform one or more functions, such as submucosal tissue expansion (e.g. duodenal submucosal tissue expansion), mucosal tissue treatment (e.g. duodenal mucosal tissue ablation or other treatment), and/or substance delivery (e.g. delivery of one or more substances into the mucosa, submucosa, and/or other luminal wall location of the duodenum, jejunum, ileum, and/or other GI wall location). In some embodiments, injectate delivery elements 520 comprise elements (e.g. needles) constructed of a material selected from the group consisting of: metal; stainless steel, plastic; PEEK, liquid crystal polymer; and combinations of these. In some embodiments, injectate delivery element 520 comprises one or more needles with an inner diameter of at least 0.0014 in and/or no more than 0.033 in, such as an inner diameter of at least 0.00625 in and/or no more than 0.01325 in, such as an inner diameter of at least 0.0075 in and/or no more than 0.009 in, such as an inner diameter of approximately 0.008 in. In some embodiments, injectate delivery element 520 comprises one or more needles constructed and arranged to have an exposed length of at least 0.125 mm and/or no more than 10 mm, such as an exposed length of at least 1 mm and/or no more than 5 mm, such as an exposed length of at least 2 mm and/or no more than 3 mm, such as an exposed length of approximately 2.5 mm. In some embodiments, injectate delivery element 520 comprises one or more needles with a diameter (e.g. Birmingham gauge) of at least 36 gauge and/or no more than 10 gauge, such as a gauge of at least 35 and/or no more than 20, such as a gauge of at least 27 and/or no more than 26. In some embodiments, injectate delivery element 520 comprises one or more needles with a bevel angle of at least 1° and/or no more than 90°, such as a bevel angle of at least 5° and/or no more than 45°, such as a bevel angle of at least 9° and/or no more than 11°, such as a bevel angle of approximately 10°.

Console 100 can comprise one or more fluid supplies, as described herein, such as to deliver fluid to one or more injectate delivery elements 520. In some embodiments, console 100 is configured (e.g. during a submucosal tissue expansion procedure) to provide fluid to each injectate delivery element 520 at a flow rate of at least 0.1 mL/min and/or no more than 120 mL/min, such as a flow rate of at least 1 mL/min and/or no more than 60 mL/min, such as a flow rate of at least 5 mL/min and/or no more than 20 mL/min, such as a flow rate of approximately 12.5 mL/min. In some embodiments, console 100 is configured (e.g. during a submucosal tissue expansion procedure) to provide, to each injectate delivery element 520, an injection volume (e.g. for delivery at each injection site) of at least 0.1 mL and/or no more than 100 mL, such as an injection volume of at least 1 mL and/or no more than 30 mL, such as an injection volume of at least 8 mL and/or no more than 12 mL, such as an injection volume of at least 9 mL and/or no more than 11 mL, such as an injection volume of approximately 10 mL. In some embodiments, console 100 is configured to provide fluid, to each injectate delivery element 520 (e.g. during a submucosal tissue expansion procedure), at a pressure of at least 1 psi and/or no more than 400 psi, such as at a pressure of at least 20 psi and/or no more than 200 psi, such as at a pressure of at least 90 psi and/or no more than 110 psi, such as at a pressure of approximately 100 psi.

Catheter 200 can comprise multiple fluid-carrying conduits as described herein. For example, multiple conduits 521, also described herein, can each attach to a fluid delivery element 520 and travel to the proximal end or at least a proximal portion of catheter 200 (e.g. conduits 521 positioned within shaft 501 and fluidly attached to a port of handle assembly 300). In some embodiments, one or more conduits 521 comprises an inner diameter of at least 0.005 in and/or no more than 0.125 in, such as an inner diameter of at least 0.04 in and/or no more than 0.10 in, such as an inner diameter of at least 0.0177 in and/or no more than 0.0183 in, such as an inner diameter of approximately 0.018 in. In some embodiments, one or more conduits 521 each comprises a length of at least 12 in and/or no more than 250 in, such as a length of at least 36 in and/or no more than 120 in, such as a length of approximately 78 in.

Functional assembly 500 can comprise one, two, three, or more tissue capture chambers 510, such as are described herein. Tissue capture chambers 510 can comprise one or more materials selected from the group consisting of: a plastic; a liquid crystal polymer; a metal; stainless steel; a thermally conductive material; and combinations of these. Tissue capture chambers 510 can comprise a durometer of less than 63D, such as less than 50D, such as approximately 40D. Each tissue capture chamber 510 can be sized and arranged to capture tissue when a vacuum is applied to tissue capture chamber 510. Each tissue capture chamber 510 can be attached (e.g. fixedly attached) to expandable element 530 via an adhesive with a glass transition temperature (Tg) of at least −60° C. and/or no more than 200° C., such as a Tg of at least 60° C. and/or no more than 90° C., such as a Tg of approximately 77° C. Alternatively or additionally, one or more tissue capture chambers 510 can be attached to expandable element 530 via visco elastic tape and/or thermal welding. Each tissue capture chamber 510 can be attached (e.g. fixedly attached) to expandable element 530 via an adhesive configured to support an elongation (e.g. without failure) of at least 1% and/or no more than 500%, such as an elongation of at least 100% and/or no more than 400%, such as an elongation of approximately 300%. Each tissue capture chamber 510 can comprise an outer diameter of at least 0.1 mm and/or no more than 10 mm, such as a diameter of at least 1 mm and/or no more than 5 mm, such as at diameter of at least 2.28 mm and/or no more than 2.30 mm, such as a diameter of approximately 2.29 mm. Each tissue capture chamber can comprise a length of at least 2.5 mm and/or no more than 500 mm, such as a length of at least 10 mm and/or no more than 50 mm, such as a length of at least 17.25 mm and/or no more than 17.75 mm, such as a length of approximately 17.5 mm. Each tissue capture chamber 510 comprises an opening 512. Each opening 512 can comprise a length of at least 0.25 mm, or at least 0.5 mm, or at least 1 mm, and/or no more than 20 mm, such as a length of at least 2 mm and/or no more than 10 mm, such as a length of at least 3.45 mm and/or no more than 3.65 mm, such as a length of approximately 3.55 mm. Each opening 512 can comprise a width of at least 0.1 mm and/or no more than 10 mm, such as a width of at least 0.5 mm and/or no more than 4 mm, such as a width of at least 1.48 mm and/or no more than 1.68 mm, such as a width of approximately 1.58 mm. Each opening 512 can comprise a depth of at least 0.1 mm and/or no more than 10 mm, such as a depth of at least 1 mm and/or no more than 4 mm, such as a depth of at least 1.9 mm and/or no more than 2.1 mm, such as a depth of approximately 2.0 mm. Each opening 512 can be defined by walls that extend from the outer surface of port 510.

In some embodiments, console 100 comprises a control module, controller 1500. Controller 1500 can comprise one or more processors, algorithms, software routines, and/or electromechanical interfaces. For example, controller 1500 can include one or more electrical and/or mechanical components that interface with one or more components of console 100 and/or another component of system 10. Console 100 can further comprise one or more user interfaces, user interface 1000. User interface 1000 can comprise one or more user input devices, such as a mouse, keyboard, joystick, button, switch, microphone, touch screen, and/or other component configured to allow an operator to provide information to system 10. User interface 1000 can also comprise one or more user output devices, such as a display, speaker, light, tactile output device, and/or other component configured to provide information to an operator of system 10. In some embodiments, controller 1500 performs (e.g. controls) one or more console operations as described herein. For example, controller 1500 can perform the operations of console 100 described in reference to Method 2300 of FIG. 6G herein.

In some embodiments, one or more components of system 10 are reusable (i.e. used in many procedures). Additionally, one or more components of system 10 can be configured to be "resposable" meaning that they are used more than once, but less than a fully reusable component of system 10. For example, in some embodiments, catheter 200 can be configured for a single use, whereas umbilical 600 and/or cartridge 3500 are resposable, such that umbilical 600 and/or cartridge 3500 are configured to be sterilized and used a finite number of times prior to disposal. Portions of console 100 (e.g. the fluid pathways) can be sterilizable and console 100 can be configured to be used many times with sterilization of those portions performed prior to each use. In some embodiments, system 10 includes one or more assemblies and/or other components that are configured to sterilize one or more sterilizable components of console 100, cartridge 3500, umbilical 600, and/or catheter 200, such as is described in reference to FIG. 2 herein.

In some embodiments, console 100 comprises a backup power supply, battery 109. Battery 109 can comprise sufficient power (e.g. sufficient energy capacity) to maintain the functionality of console 100 (e.g. in the event of a power failure), such as to perform any actions necessary to transition one or more components of system 10 into a patient-safe mode. For example, in the event of a power failure during an ablative treatment step in which hot fluid is positioned in expandable element 530, battery 109 can comprise sufficient power to allow console 100 to sufficiently remove the hot fluid from expandable element 530. In some embodiments, when relying on power from battery 109, system 10 only performs the functions necessary to transition one or more components of system 10 into a patient-safe mode (e.g. hot fluid removal is prioritized versus non-essential functions of system 10).

System 10 as described in reference to FIG. 1 and otherwise herein, can be configured to provide a volumetric inflation (e.g. inflation with a known volume of fluid) of an expandable element (e.g. assembly 530 of catheter 200) in order to perform a tissue expansion procedure (e.g. deliver fluid into submucosal tissue of the small intestine), and also perform a flow rate-controlled tissue ablation procedure via an expandable element (e.g. assembly 530 configured to ablate mucosal tissue of the small intestine). The tissue expansion and tissue ablation can be performed using a single device (e.g. catheter 200). The volumetric inflation and flow rate-controlled ablation can be performed by a syringe pump mechanism (e.g. inflation fluid supply 130, ablative fluid supply 140, and neutralizing fluid supply 150 comprise a single, or multiple, syringe pumps).

Figure 3:
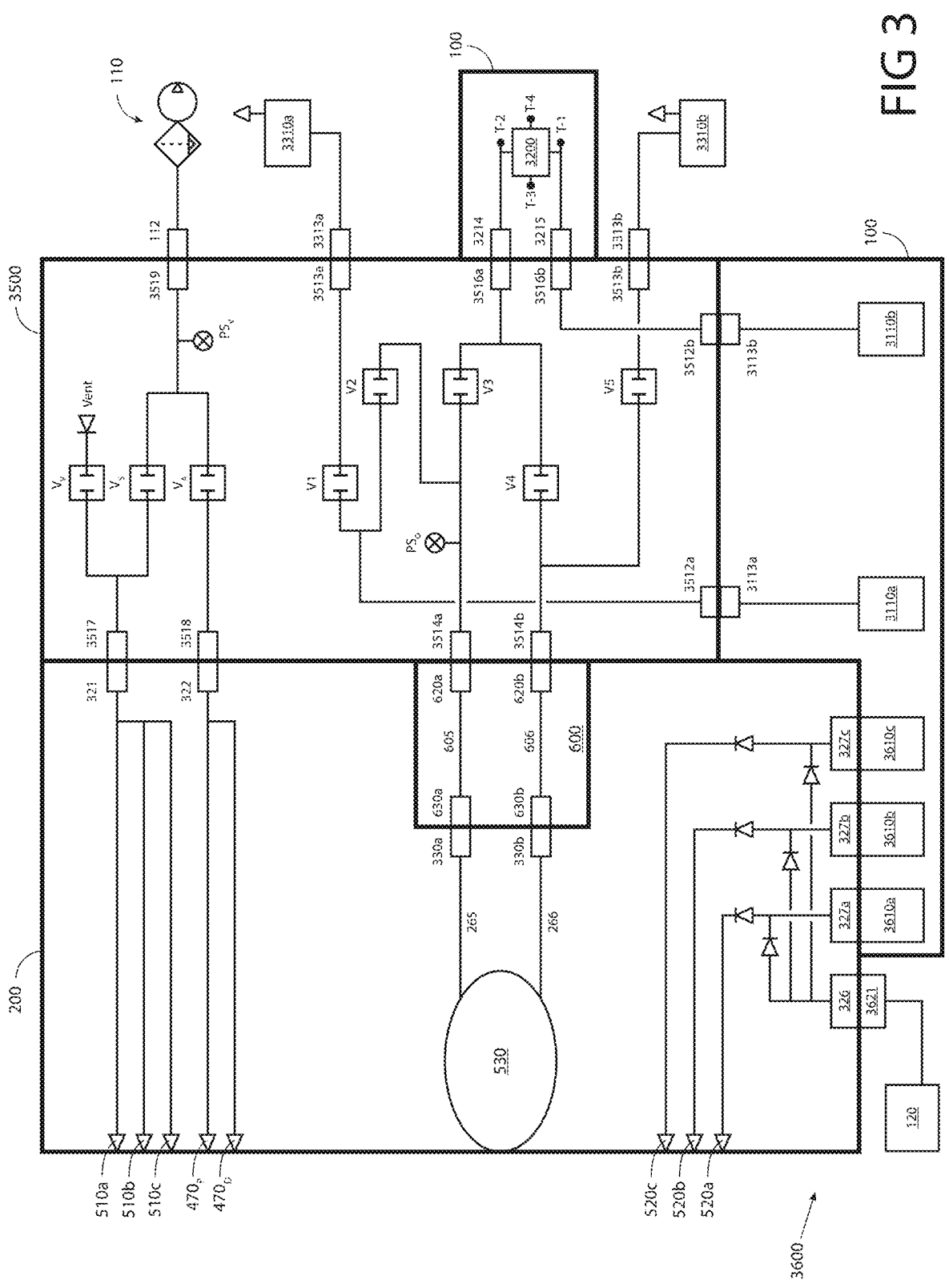
FIG. 3 illustrates a schematic view of another tissue treatment system including an elongate device, and a console with a cartridge, syringe pump assemblies, and fluid reservoirs attachable thereto, consistent with the present inventive concepts.

In some embodiments, catheter 200 comprises multiple injectate delivery elements 520 (e.g. two, three, four or more), and injectate supply 120 comprises an independent fluid delivery mechanism for each delivery element 520 (e.g. a separate syringe pump or other pumping mechanism and associated fluid pathway for each element 520, such as is described in reference to FIG. 3 herein). This independent fluid delivery can be configured to ensure that each delivery element 520 delivers a desired amount of injectate 125 (e.g. each delivery element 520 delivers the same amount of injectate 125). Alternatively, injectate supply 120 can comprise a single syringe pump or other pumping mechanism that provides injectate 125 to two or more delivery elements 520 and the associated fluid pathways of console 100 and catheter 200 are constructed and arranged to have similar flow resistances, such that similar volumes of injectate 125 are delivered by the multiple delivery elements 520. In some embodiments, injectate supply 120 is configured to provide a pressure-limited delivery of injectate 125, such as to avoid over-pressurizing one or more fluid pathways of console 100 and/or catheter 200.

In some embodiments, system 10 is configured to perform one, two, three or more ablation cycles during a clinical procedure, without maintaining a reservoir of ablation temperature fluid during the procedure. For example, an "ablation cycle" can comprise the thermal treatment of an axial segment of the GI tract, such as is described herebelow in reference to FIG. 3 and others herein. The necessity of maintaining a reservoir of fluid at a temperature sufficient to ablate tissue during an entire tissue treatment procedure can be costly and/or technologically complicated, and the ability to perform the required number of ablation cycles without such a reservoir can provide numerous advantages. As described herein, in some embodiments system 10 utilizes a two-pass heating method for providing ablation temperature hot fluid, avoiding the necessity of maintaining (e.g. continuously maintaining) a reservoir of ablation temperature hot fluid. Alternatively or additionally, system 10 can include a reservoir configured to maintain ablation temperature fluid during a procedure, such as a when system 10 comprises a reservoir that includes a low cost and/or reusable heating element. In some embodiments, system 10 comprises an intermediate reservoir (e.g. a reservoir positioned inline between a main reservoir of fluid and catheter 200) comprising a heating element configured to heat the fluid within the intermediate reservoir (e.g. only the fluid within the intermediate reservoir) to an ablative temperature between ablations.

As described herein, system 10 can utilize a two-pass heating method for providing ablation temperature fluid. In some embodiments, system 10 comprises a heater with a power capacity of less than 1200 W, such as less than 1000 W or less than 900 W. A heater with a higher power rating can be cost prohibitive and can also produce waste heat (e.g. heat not applied directly to the ablative fluid), which requires management by system 10 (e.g. heat sinks or other heat dissipation devices or methods). In a single pass heating system, an inline heater may require a power rating of 3000 W or more to provide ablative fluid at a desired flow rate of at least 8 mL/s, such as at least 9 mL/s or at least 10 mL/s. As described herein, in some embodiment using a two-pass method, ablative fluid is passed through a heating element at a slower rate on the first pass (e.g. less than 8 mL/s, 7 mL/s, or 6 mL/s), and a faster rate on the second pass (e.g. at least 8 mL/s, 9 mL/s, or 10 mL/s). In some embodiments, system 10 is configured to limit the power provided to the heater (e.g. limit the power provided over a time period) such that no more than the required amount of power is provided to sufficiently heat the fluid for a single ablation cycle.

As described herein, system 10 can be configured to perform two, three, or more ablation cycles during a clinical procedure. In some embodiments, system 10 is configured to perform a tissue treatment procedure with a reservoir comprising less than 5 L of fluid, such as less that 4 L, 3 L, or 2 L. As described herein, system 10 can be configured to minimize the fluid used during the tissue treatment procedure by reusing fluid which has been used to precool target tissue to subsequently ablate target tissue (e.g. by recirculating and heating the fluid between a precooling and ablation step, as described herein).

Figure 1A:
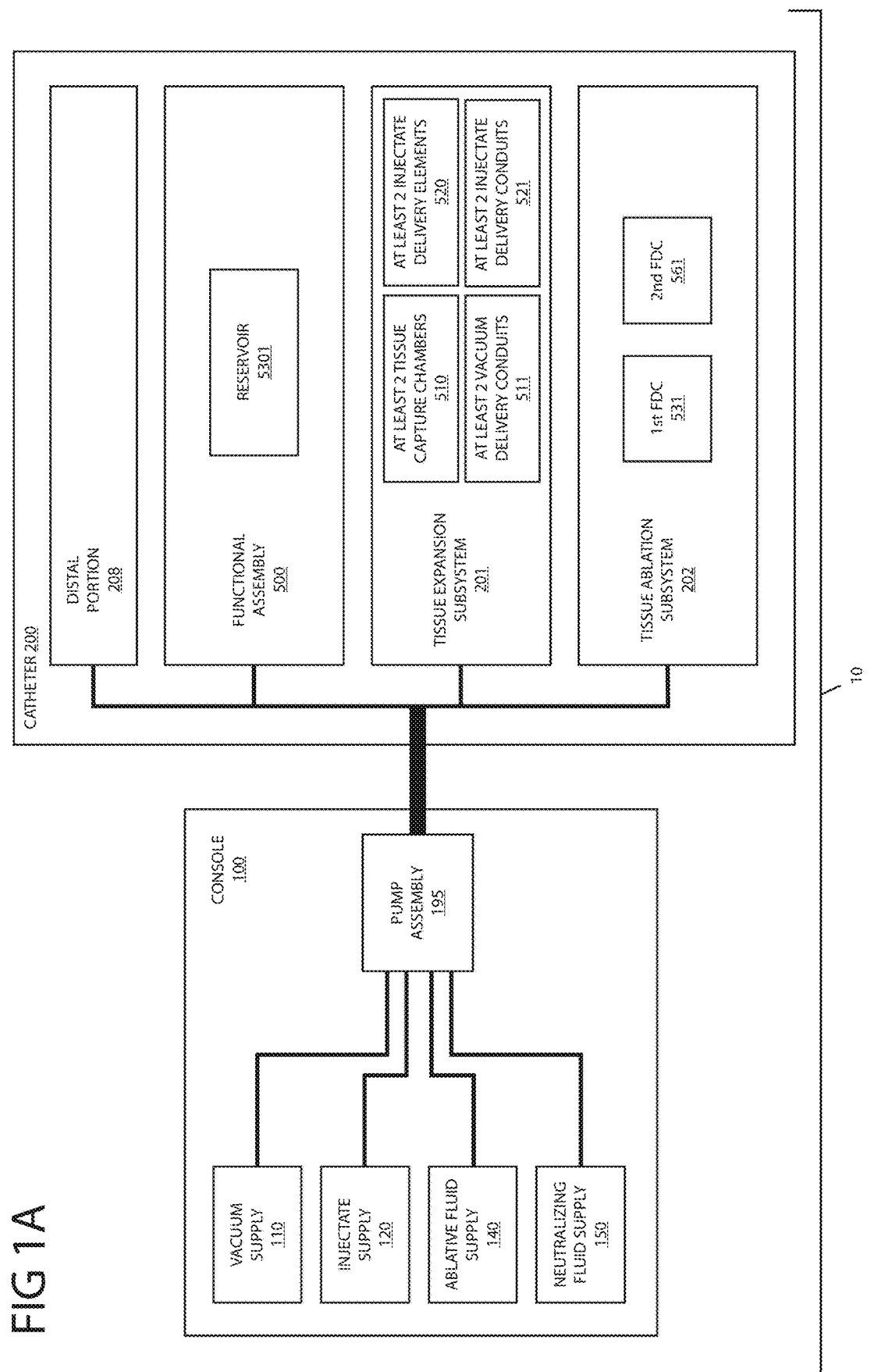
FIG. 1A illustrates a schematic view of a system for performing a medical procedure in the intestine of a patient, consistent with the present inventive concepts.

Referring now to FIG. 1A, a schematic view of a system for performing a medical procedure in the intestine of a patient is illustrated, consistent with the present inventive concepts. System 10 comprises console 100 and catheter 200. Console 100, catheter 200, and/or other components of system 10 of FIG. 1A can be of similar construction and arrangement to those described hereabove in reference to FIG. 1. Console 100 of FIG. 1A comprises at least vacuum supply 110, injectate supply 120, ablation fluid supply 140, and neutralizing fluid supply 150, each of which can be included within a single housing or multiple housings of console 100. Console 100 can include other fluid supplies and assemblies as described herein. Console 100 is fluidly and otherwise operatively attached to catheter 200, such as via an umbilical or other conduit, not shown but such as umbilical 600 described herein. Console 100 comprises one or more pumps, pumping assembly 195, which propels fluids between console 100 and catheter 200, also as described herein.

Catheter 200 comprises a distal portion 208 and a functional assembly 500 which can be positioned on distal portion 208. Functional assembly 500 comprises one or more balloons or other expandable reservoirs, such as reservoir 5301 shown. Console 100 can be configured to transport fluids into and out of reservoir 5301, such as to expand and contract, respectively, reservoir 5301, as described herein.

Catheter 200 further comprises a tissue expansion subsystem 201 configured to expand sub-surface tissue, such as submucosal tissue of the GI tract. Tissue expansion subsystem 201 can comprise conduits within catheter 200 which transport tissue expansion fluids to functional assembly 500 and provide a vacuum to functional assembly 500, each as described herein. Tissue expansion subsystem 201 can comprise at least two tissue capture chambers 510 configured to capture tissue when vacuum is applied via at least two vacuum delivery conduits 511 (e.g. vacuum provided by vacuum supply 110 of console 100). Tissue expansion subsystem 201 can comprise at least two injectate delivery elements 520 (e.g. needles or fluid jets) which can receive the tissue expansion fluid (e.g. injectate 125 provided by injectate supply 120 of console 100) via at least two injectate delivery conduits 521. Injectate delivery elements 520 can be configured to deliver the tissue expansion fluid to tissue captured by tissue capture chambers 510. One or more injectate delivery elements 520 can each comprise a needle configured to penetrate tissue (e.g. via advancement of the needle into chamber 510 when tissue is captured within the chamber 510 via the applied vacuum), after which fluid can be delivered into the tissue. Alternatively or additionally, one or more injectate delivery elements 520 can each comprise a fluid jet configured to deliver fluid through a surface of and into tissue captured within chamber 510.

Catheter 200 further comprises tissue ablation subsystem 202 comprising conduits within catheter 200 which transport ablation fluids and neutralizing fluids to and from functional assembly 500. Tissue ablation subsystem 202 comprises a first conduit, conduit 531, configured to provide fluid to functional assembly 500 (e.g. to reservoir 5301) and a second conduit, conduit 561, configured to remove fluid from functional assembly 500 (e.g. from reservoir 5301). Conduit 531 can be configured to provide to functional assembly 500 ablative fluid (e.g. fluid at an ablative temperature that is provided by ablative fluid supply 140 of console 100), as well as neutralizing fluid (e.g. neutralizing fluid provided by neutralizing fluid supply 150 of console 100 for cooling or warming of tissue prior to and/or after heat ablation or cryogenic ablation, respectively). Conduit 561 can be configured to remove ablative fluid and neutralizing fluid from functional assembly 500. In some embodiments, console 100 is configured to recirculate ablative fluid within functional assembly 500 (e.g. within one or more reservoirs of functional assembly 500), and to also recirculate neutralizing fluid within functional assembly 500 (e.g. within similar or dissimilar reservoirs of functional assembly 500). In some embodiments, console 100 is configured to sequentially recirculate ablative fluid and neutralizing fluid in a single reservoir (e.g. reservoir 5301) of functional assembly 500, such as to heat ablate tissue (e.g. target tissue) and subsequently cool tissue (e.g. target tissue and/or tissue proximate target tissue), or to pre-cool tissue and subsequently ablate tissue. In some embodiments, console 100 is configured to sequentially recirculate ablative fluid and neutralizing fluid in functional assembly 500 to pre-cool tissue, then ablate tissue, and then cool tissue.

Figure 1B:
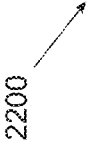
FIG. 1B illustrates a flow chart of a method of treating target tissue of a patient, consistent with the present inventive concepts.

Referring now to FIG. 1B, a flow chart of a method of treating target tissue of a patient is illustrated, consistent with the present inventive concepts. In some embodiments, the Method 2200 of FIG. 1B is accomplished using system 10 of FIG. 1 or otherwise as described herein. In Step 2210, a patient is selected for treatment, such as a patient selected to treat and/or diagnose ("treat" herein) a patient disease or disorder selected from the group consisting of: Type 2 diabetes; Type 1 diabetes; "Double Diabetes"; gestational diabetes; hyperglycemia; pre-diabetes; impaired glucose tolerance; insulin resistance; non-alcoholic fatty liver disease (NAFLD); non-alcoholic steatohepatitis (NASH); obesity; obesity-related disorder; polycystic ovarian syndrome (PCOS); hypertriglyceridemia; hypercholesterolemia; psoriasis; GERD; coronary artery disease (e.g. as a secondary prevention); stroke; TIA; cognitive decline; dementia; Alzheimer's Disease; neuropathy; diabetic nephropathy; retinopathy; heart disease; diabetic heart disease; heart failure; diabetic heart failure; and combinations of these. In some embodiments, the patient is selected to treat two or more of the above diseases or disorders, such as a patient selected to treat two or more of diabetes, insulin resistance, NAFLD, NASH, and/or PCOS.

The patient selected can be taking one or more medicines to treat their diabetes. The patient selected can have an HbA1c level between 7.5% and 12.0%, between 7.5% and 10%, or between 7.5% and 9.0%. In some embodiments, the patient selected can have an HbA1c level between 6.0% and 12.0%. Patients with higher HbA1c levels and/or other higher disease burden can receive more aggressive treatments (e.g. more tissue treated and/or higher number of repeated treatments over time) as described herebelow in reference to Step 2250.

Patient selection can be based on the current level of one or more parameters representing one or more various biomarkers or other representative values of physiologic conditions (e.g. as compared to an average among diabetic and/or non-diabetic patients), such as a level of a parameter selected from the group consisting of: body mass index (BMI) level; waist circumference; HbA1c level; fasting glucose; insulin resistance; liver fibrosis; cholesterol or triglyceride level; duration of years exhibiting type 2 diabetes; fasting insulin, fasting C-peptide or C-Peptide stimulation in response to a meal; age; and combinations of these.

Prior to placing one or more devices into the patient (e.g. catheter 200), or at any time thereafter (e.g. during or after the procedure), one or more agents can be introduced into the patient. In some embodiments, one or more agents are introduced into the GI tract directly, such as agent 80 described hereabove in reference to FIG. 1. In some embodiments, agent 80 comprises L-menthol (i.e. oil of peppermint) or other agent configured to provide an anti-peristalsis effect. In these embodiments, a few drops of agent 80 can be placed in an irrigation or other lumen of an inserted device (e.g. endoscope 50). In some embodiments, approximately 8 mL of L-menthol is mixed with approximately 0.2 mL of Tween 80 (polysorbate 80) in approximately 500 mL of distilled water (i.e. to create an approximately 1.6% solution). Approximately 20 mL of this mixture can be sprayed through a working channel of endoscope 50, or more as required to dampen peristalsis. In some embodiments, the solution can vary between approximately 1.6% and 3.2%. Tween and/or sorbitan monostearate can be used as an emulsifier.

One or more agents 80 can be delivered once endoscope 50 or any other agent delivery device of system 10 enters the duodenum. In some embodiments, agent 80 comprises one or more agents that are delivered intravenously, and can include glucagon and/or buscopan.

As described herein, in some embodiments, an endoscope is inserted into the patient (e.g. endoscope 50 of FIG. 1). In these embodiments, subsequently inserted devices can be placed through a working channel of endoscope 50 and/or alongside endoscope 50. In some embodiments, endoscope 50 and an attachable sheath are both inserted into the patient, and subsequently inserted devices can be placed through a working channel of endoscope 50, through the attachable sheath, and/or alongside endoscope 50 and the attached sheath. Each device placed within the patient can be inserted over a guidewire. In some embodiments, an endoscope stiffening device is used, such as an endoscope stiffening system provided by Zutron Medical of Lenexa, Kansas, USA.

In some embodiments, non-target tissue is identified. Non-target tissue can be identified with a visualization device, such as endoscope 50 and/or imaging device 70 described herein. The non-target tissue can comprise the ampulla of Vater, the pancreas, and/or other tissue to which treatment (e.g. ablation) may adversely affect the patient. Marking of the non-target tissue (or tissue proximate the non-target tissue) can be performed, such as with a tattoo, ink or other visualizable substance, such as a visual agent or clip placed in and/or on the mucosa and/or submucosa in or proximate the ampulla of Vater. In some embodiments, one or more markers similar to marker 90 described hereabove in reference to FIG. 1 are deployed in the patient to provide a reference location relative to non-target tissue. Tissue expansion and/or tissue treatment performed in subsequent steps can avoid treating (e.g. avoiding delivering ablative energy to) the non-target tissue identified and potentially marked (e.g. with one or more markers 90).

Next in Step 2210, a treatment catheter, such as catheter 200 of FIG. 1, is inserted through the patient's mouth and advanced through the stomach and into the small intestine. Step 2210 can include selecting a particular model of catheter 200, such as a particular size (e.g. treatment element length and/or diameter) or other configuration of catheter 200. Catheter 200 can be inserted over guidewire 60, such as are described hereabove in reference to FIG. 1. Guidewire 60 can be advanced such that its distal end is in the jejunum or more distal location. During advancement of catheter 200, guidewire 60 can be held taut in order to prevent catheter 200 from forming a loop in the stomach. As described herein, catheter 200 can be inserted through a working channel of endoscope 50 and/or alongside endoscope 50.

Catheter 200 is advanced (e.g. over guidewire 60) such that functional assembly 500 is positioned in the duodenum (or another GI location). One or more tissue capture chambers 510 (e.g. three tissue capture chambers 510 positioned on expandable element 530 of functional assembly 500) can be positioned at a first location in the intestine. The first location can be a most-proximal target location to be treated, such as a location in the duodenum at least 0.5 cm or at least 1 cm, but not more than 5 cm or 10 cm from the ampulla of Vater. In some embodiments, tissue capture chambers 510 are positioned based on the location of a previously placed marker, such as marker 90 described herein. Prior to and/or during insertion of catheter 200, a stiffening wire can be inserted within catheter 200. Endoscope 50 can be positioned adjacent catheter 200, such that the distal ends of each are positioned beyond the ampulla of Vater (e.g. beyond marker 90).

In some embodiments, Method 2200 does not continue beyond Step 2210 prior to receiving a positive operator confirmation (e.g. via operator input to system 10), such as in the event functional assembly 500 is in the proper position relative to the tissue to be expanded.

In Step 2220, submucosal tissue expansion is performed, or at least attempted, at the first location (e.g. a first axial segment of the duodenum). Saline and/or other fluid or material (injectate 125) is injected into submucosal tissue. In some embodiments, injectate 125 is delivered (e.g. simultaneously injected) by multiple injectate delivery elements 520 of functional assembly 500, each element 520 positioned in a corresponding tissue capture chamber 510 (e.g. three chambers 510 spaced approximately 120° apart along a circumference). Each injection (by a single injectate delivery element 520) can comprise at least 1 mL, such as at least 2 mL, at least 5 mL or at least 8 mL per each injectate delivery element 520 (e.g. when the cumulative amount of fluid delivered by the multiple injectate delivery element 520 comprises at least 3 mL, such as at least 6 mL, at least 15 mL, or at least 24 mL). Each injection can comprise no more than 20 mL, such as no more than 15 mL, or when each injection comprises approximately 10 mL (e.g. when the cumulative amount of fluid delivered by the multiple injectate delivery element 520 comprises no more than 60 mL, such as no more than 45 mL, or when the cumulative amount comprises approximately 30 mL). In some embodiments, each injection comprises at least 4 mL, at least 6 mL, or at least 8 mL. In some embodiments, the volume of injectate delivered (e.g. via three circumferentially positioned injectate delivery elements 520) can be configured to achieve an expansion of the submucosal layer to a thickness of at least 250 μm, or approximately 400 μm, in the area surrounding the volume of mucosal tissue to be ablated. Console 100 can be configured to deliver injectate 125 at a flow rate of at least 1 mL/min, or at least 10 mL/min, such as a flow rate of 50 mL/min, or 100 mL/min. In some embodiments, console 100 is configured to deliver the full volume of injectate for a single injectate delivery element 520 at a single site within a time period of no more than 2 minutes, no more than 1 minute, or no more than 30 seconds. In some embodiments, injectate 125 is injected into tissue in a closed loop fashion, such as until a pressure threshold is reached (e.g. pressure within a delivery element), until the pressure within a balloon or other functional element placed proximate the injection site increases above a threshold, and/or until the inner diameter of the duodenum is reduced to a certain size or by a percentage of its pre-injection size.

Volumes injected by the multiple injectate delivery elements 520 can be selected to achieve near full circumferential expansion of submucosal tissue (e.g. without gaps, full 360° expansion). Each submucosal tissue expansion step is configured to create a safety margin of expanded submucosal tissue, as described herein, this expanded tissue volume (e.g. a partial or full circumferential tubular volume of the intestine) defining an "expanded tissue periphery". In some embodiments, functional assembly 500 is constructed and arranged (e.g. the ablative portion is sized) such that a submucosal tissue expansion performed at a single axial location of the small intestine (e.g. via delivery of injectate 125 via two, three or more injectate delivery elements 520, simultaneously or sequentially at the single axial location)

creates an expanded tissue periphery that is sufficiently sized to surround an "ablation periphery" that is created during ablation via functional assembly 500 (as described herebelow in reference to Step 2250). This sufficiently sized expanded tissue periphery avoids transmission of significant energy beyond the submucosal layer (e.g. avoids transmission of energy at a level sufficient to ablate the deeper, muscular layers of the GI tract). For example, in cases of full circumferential submucosal tissue expansion, if the axial length of the expanded submucosal tissue achieved by injectate 125 delivery in Step 2220 is greater than the axial length of the tissue to be ablated, the submucosal tissue expanded is sufficient to provide a safety margin for the ablation (e.g. when during ablation functional assembly 500 is relatively centered within the expanded length of tissue).

In some embodiments, the expanded tissue periphery created in a single submucosal tissue expansion step is not sufficiently sized to support the ablation periphery created by functional assembly 500, and an optional Step 2225 is performed (e.g. one or more times), comprising additional submucosal tissue expansion. For example, a second submucosal tissue expansion can be performed at a neighboring (e.g. relatively adjacent and more distal) axial segment of the duodenum, such as by translating (e.g. advancing) catheter 200 to reposition functional assembly 500. In some embodiments, Step 2225 is not performed prior to receiving a positive operator confirmation (e.g. via operator input to system 10 via a user-activated control), such as in the event functional assembly 500 is in the proper position relative to the tissue to be expanded. Functional assembly 500 can be at least partially collapsed (e.g. ablation fluid 145, neutralizing fluid 155, and/or other fluid is removed from functional assembly 500) prior to translation. Translations of catheter 200 (advancements and/or retractions of functional assembly 500 or other portion of catheter 200) can be performed under visualized guidance, such as when functional elements 499a, 499b and/or 599 described herein comprise a radiopaque band or other visualization marker that can be visualized by imaging device 70 (e.g. a fluoroscope). Alternatively or additionally, rotations of catheter 200 (e.g. rotations of functional assembly 500 or other portion of catheter 200) can be performed under similar visualized guidance. In Step 2225, catheter 200 can be translated (e.g. advanced) a pre-determined distance (e.g. a distance of at least 0.3 cm, or at least 0.6 cm), after which delivery of injectate 125 can begin. Delivery of injectate 125 via the injectate delivery elements 520, as described hereabove in reference to Step 2220, creates a second (e.g. contiguous) volume of expanded submucosal tissue that in combination with the first expanded volume of submucosal tissue defines a larger expanded tissue periphery than that which is created in a single tissue expansion step. This larger expanded tissue periphery can support larger ablation peripheries (e.g. longer full circumferential lengths of tissue to be ablated), such as may be required by functional assembly 500 in a single ablation. For example, in cases of full circumferential submucosal tissue expansion, if the axial length of the expanded submucosal tissue achieved by injectate 125 delivery in the combined deliveries of Step 2220 and Step 2225 is greater than the axial length of the tissue to be ablated, the submucosal tissue expanded is sufficient to provide a safety margin for the ablation.

Figure 1C:
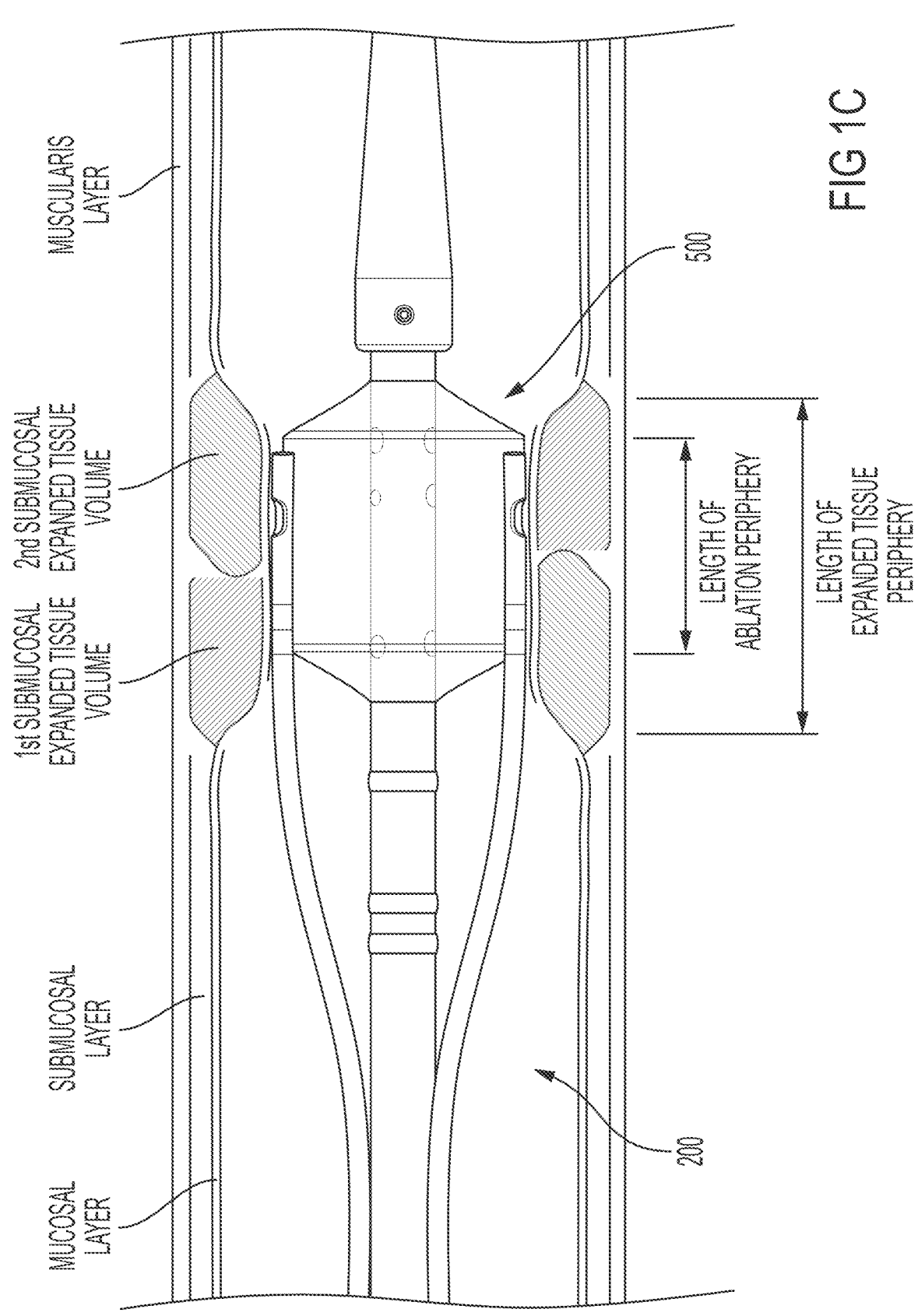
FIG. 1C illustrates a representative expanded periphery and ablation periphery of two full circumferential expansions followed by a single full circumferential ablation, each performed by a catheter via a console as described herein, consistent with the present inventive concepts.

Referring additionally to FIG. 1C, a representative expanded periphery and ablation periphery of two full circumferential expansions followed by a single full circumferential ablation, each performed by catheter 200 via console 100 as described herein, are illustrated. A first and second circumferential submucosal tissue expansion combine to form an expanded tissue periphery with a length as shown. Functional assembly 500 can deliver energy to an ablation periphery that is positioned within the expanded tissue periphery.

Optional Step 2225 can be performed two or more times, resulting in three or more injections of fluid into tissue (e.g. submucosal tissue), with or without an intervening ablation performed via Step 2250. Sequential injections of injectate 125 can be performed at an axial separation distance of between 1 cm and 2 cm apart from a previous injection (e.g. 1 cm to 2 cm distally in the duodenum, jejunum, or other GI location). In some embodiments, multiple injections are positioned at least 0.5 cm apart along the axis of the small intestine, such as between 1.0 cm and 5.0 cm apart, such as approximately 1.0 cm, 2.0 cm, 3.0 cm, 4.0 cm and/or 5.0 cm apart from one another along the axis of the small intestine. In some embodiments, axial separation of injection sites (i.e. translation distance of catheter 200 between injections) can approximate half the length of expandable element 530 onto which injectate delivery elements 520 are mounted, such as half the length of expandable element 530 of FIG. 1. In some embodiments, a series of 5-15 sets (e.g. 8-12 sets) of injections (e.g. each set comprising injections from 2, 3 or more injectate delivery elements 520) can be performed (with or without an intervening ablation step) by delivering injectate 125 (e.g. a fluid containing a visualizable dye) to the tissue to be expanded and subsequently translating catheter 200 to a new axial location (e.g. after proper expansion of tissue is confirmed visually as described herebelow in Steps 2230 and 2235, or otherwise). Each advancement and/or retraction of catheter 200 can be made in unison with advancement and/or retraction of an endoscope positioned alongside catheter 200.

As described herein, tissue expansion can begin at a location proximate but distal to the ampulla of Vater, such as at a location at least 1 cm distal to but not more than 5 cm or 10 cm from the ampulla of Vater. A series of relatively contiguous, full circumferential submucosal tissue expansions can be performed (e.g. moving distally), for example to a distal location up to the Ligament of Treitz. In alternate embodiments, multiple full circumferential tissue expansions are performed by moving catheter 200 from distal to proximal locations, or in a discontinuous (back and forth) manner.

Volumes of injections and/or axial separation of injection sites can be chosen to avoid axial gaps between neighboring expanded volumes of tissue (e.g. when an ablation step is to be performed proximate one or both expanded volumes of tissue). After injections, gaps identified circumferentially and/or axially (e.g. via endoscope camera, fluoroscope or ultrasound imaging device), can be filled in as deemed necessary via additional injection (e.g. with or without rotation and/or translation of catheter 200).

In some embodiments, console 100 is configured to reduce the amount of fluid (e.g. liquid such as water or gas such as air or carbon dioxide) in expandable element 530 supporting injectate delivery elements 520 as the injectate 125 is delivered into tissue, such as to prevent excessive force being applied to tissue proximate the expanding tissue (i.e. due to the decreasing lumen of the intestine proximate the expanding tissue in contact with expandable element 530).

Multiple injections (e.g. two, three or more injections from two, three or more equally separated injectate delivery elements 520) can be performed simultaneously or sequentially in a single axial segment of the intestine (e.g. without moving functional assembly 500). A vacuum can be applied (e.g. automatically or otherwise via system 10, such as via a working channel of endoscope 50 and/or via ports 470P or 470D of catheter 200) to the intestinal lumen (e.g. desufflation) prior to delivery of injectate 125, such as to draw tissue toward each injectate delivery element 520 (e.g. into the associated chambers 510). After injectate 125 delivery, the vacuum can be removed and an ablation performed (e.g. in Step 2250 below without additional translation or other movement of functional assembly 500), or catheter 200 can be advanced (or retracted) for a subsequent (additional) tissue expansion.

In Step 2230, an assessment of submucosal tissue expansion is performed (e.g. manually by an operator and/or automatically by system 10). Step 2230 can be performed after Step 2225, as shown in FIG. 1B (e.g. if Step 2225 is performed), and/or directly after Step 2220 (e.g. when a single tissue expansion is sufficient for the subsequent ablation or simply when an assessment is desired directly after a tissue expansion). In some embodiments, assessment of submucosal tissue expansion is performed via a camera view provided by endoscope 50 (e.g. an endoscope with a camera positioned to view the submucosal tissue expansion). Alternatively or additionally, submucosal tissue expansion can be performed using a visualization device of system 10, such as when imaging device 70 described hereabove in reference to FIG. 1 provides one or more images used to perform the assessment. Injectate 125 delivered in Steps 2220 and/or 2225 can include an agent that is directly visualizable by an operator and/or an agent whose location (e.g. a volume of tissue that has been expanded by injectate 125) can be (at least partially) assessed by system 10 (e.g. via an image processing algorithm of console 100 or other component of system 10). For example, injectate 125 can comprise a material selected from the group consisting of: a visible material (such as India Ink, Indigo Carmine, and the like) visualized by an endoscope 50 camera, catheter 200 camera (e.g. when functional element 599 comprises a camera), or other camera; a radiopaque material visualizable by an imaging device 70 comprising a fluoroscope or other X-ray imaging device; an ultrasonically reflectable material visualizable by an imaging device 70 comprising an ultrasound imaging device; any visualizable material; and combinations of one or more of these. Visualization of the expanded tissue can be used to determine (e.g. automatically determine by an algorithm of system 10) that a proper volume of injectate has been delivered as well as sufficient tissue expansion has been achieved, such as to ensure sufficient thickness, elimination of gaps, sufficient axial length, and/or sufficient circumferentially (e.g. full or near-full circumferential nature) of tissue expansion has occurred. The pressure of expandable element 530 or the volume of fluid within expandable element 530 can also be monitored to determine if a proper volume of injectate has been delivered to achieve adequate tissue expansion. In particular, the expanded tissue can be analyzed to identify areas of relatively poor expansion which may indicate regions of adherent submucosal tissue (such as scarred and/or fibrotic submucosal tissue not amenable to tissue expansion).

As described above, in some embodiments, assessment of submucosal tissue expansion performed in Step 2230 is performed (at least) using a camera of endoscope 50. In these embodiments, prior to and/or during the assessment of submucosal tissue expansion performed in Step 2230, functional assembly 500 can be at least partially collapsed (e.g. inflation fluid 135, and/or other fluid is removed from functional assembly 500), to provide an increased view of the expanded tissue. Alternatively or additionally, functional assembly 500 is at least partially collapsed to allow advancement of endoscope 50 toward and potentially into the axial segment of intestinal tissue to which the submucosal tissue has been expanded, to provide a closer view of the expanded tissue.

In Step 2235, adequacy of submucosal tissue expansion is determined (e.g. a qualitative assessment performed by a clinician and/or a quantitative assessment performed automatically and/or semi-automatically using system 10). If submucosal tissue expansion is determined to be inadequate, Step 2240 is performed, in which a new (alternative) area for tissue expansion and subsequent ablation is selected, or the procedure is terminated (e.g. after limited or no ablations have been performed). In some embodiments, the Method 2200 of FIG. 1B is included in a medical procedure that is performed on a patient after (e.g. at least 24 hours after) a similar procedure has been performed on that same patient (e.g. a similar ablation procedure in the duodenum or other location of the patient's small intestine or GI tract). The assessment of submucosal expansion performed in Step 2230 can be an important diagnostic test that can confirm that it is safe to perform a repeated, similar procedure (e.g. the procedure of the present inventive concepts). Alternatively, the assessment may enable the identification of patients who may have: an active infection in their small intestine; a history of infection (such as tuberculosis) and/or malignancy that can cause a GI segment injury (e.g. a condition that may make submucosal expansion challenging or even impossible); and combinations of these, such as patients to which no or limited ablations should be performed. For example, there may be significant fibrosis and/or significant scar present at a target location (from a previous procedure or otherwise), which could prevent proper submucosal tissue expansion. In these instances, ablation should not be performed, at least not at that location of the intestine.

If the submucosal tissue expansion is determined to be adequate, Step 2250 is performed in which target tissue is treated (e.g. ablated) by functional assembly 500 of catheter 200. The target tissue can comprise one or more portions of the mucosal layer of the duodenum, jejunum, and/or other GI location proximate (e.g. on top of) the submucosal tissue that has been previously expanded (e.g. in one or more expansion steps 2220 and/or 2225). Treated tissue can further comprise at least an inner layer of neighboring submucosal tissue (e.g. a partial depth of the submucosal tissue layer previously expanded). In some embodiments, the ablation of Step 2250 is performed without repositioning (e.g. without translating) functional assembly 500, such as without repositioning after Step 2220 or without repositioning after Step 2225 (if the optional step is performed), such as to ensure that ablation is performed over an area of expanded submucosal tissue (e.g. over a sufficiently sized expanded tissue periphery as defined herein) that provides a safety margin to avoid adversely affecting tissue layers beyond (deeper than) the submucosal layer. One or more circumferential ablations, partial circumferential ablations, and/or other treatments can be performed along a length of the GI tract (e.g. along one or more axial segments of the GI tract), such as along a length of the duodenum at least 1 cm distal to the ampulla of Vater, such as at a location at least 1 cm distal to but within 3 cm, 5 cm or 10 cm of the ampulla of Vater. In some embodiments, all ablations are performed at least 2 cm or at least 3 cm distal to the ampulla of Vater (e.g. tissue within 1 cm, 2 cm or 3 cm of the ampulla of Vater is not ablated). In some embodiments, tissue treatments are only performed at locations that have had submucosal tissue expansion performed and/or confirmed (e.g. visually as described hereabove in reference to Step 2230 and 2235).

In some embodiments, Step 2250 must be performed within a predetermined time limit of the most recent submucosal tissue expansion step (e.g. Step 2220 or 2225). For example, in some embodiments, console 100 only allows Step 2250 to be performed within 10 minutes, such as within 5 minutes of Step 2220 or 2225. In some embodiments, if the predetermined time limit has elapsed, console 100 requires additional submucosal expansion to be performed before allowing a tissue treatment step to be performed.

In some embodiments, a thermal ablation is provided by sufficiently hot or sufficiently cold fluid introduced into expandable element 530 to ablate tissue. Alternatively or additionally, different forms of energy delivery or other tissue treatments can be performed (e.g. electromagnetic energy, light energy, mechanical energy and/or chemical energy).

Catheter 200 and console 100 can be configured to treat a series of axial segments of GI tract tissue comprising lengths between 1 cm and 5 cm each, such as approximately 2 cm in length each. Catheter 200 and console 100 can be configured to treat a cumulative axial length of GI tract tissue (e.g. an axial length of duodenal mucosal tissue) of less than or equal to 3 cm, 6 cm, 9 cm, 15 cm, or 20 cm. Catheter 200 and console 100 can be configured to treat more than 3 cm of axial length of duodenal mucosa, such as more than 3.4 cm, more than 6 cm, more than 7 cm, more than 8 cm or more than 9 cm (e.g. approximately 9.3 cm). In some embodiments, at least 10%, 15%, 25%, 30% and/or 50% of the duodenal mucosa distal to the ampulla of Vater is treated. The axial length and/or overall volume of tissue treated can correspond to a patient parameter, such as the longevity of the disease or other disease parameter as described herein (e.g. higher disease burden correlating to larger volumes of tissue treated).

In some embodiments, at least 3 axial segments of duodenal mucosal tissue are treated (e.g. sequentially ablated, such as a sequential treatment including at least one submucosal tissue expansion step performed before each ablation), such as with a functional assembly 500 configured to deliver energy to a delivery zone with a length between 0.5 cm and 4.0 cm (e.g. tissue contacting length of expandable element 530 filled with ablative fluid), such as a delivery zone length (e.g. tissue contacting length) between 0.5 cm and 4.0 cm, between 1.5 cm and 3.3 cm, or approximately 2 cm in length. In some embodiments, at least 4 axial segments of duodenal mucosal tissue are treated, such as when at least 6 axial segments of duodenal mucosal tissue are treated. In these embodiments, functional assembly 500 can be configured to deliver energy to a delivery zone with a length between 0.7 cm and 2.0 cm (e.g. tissue contacting length of expandable element 530 filled with ablative fluid). In some embodiments, functional assembly 500 comprises ablative fluid delivered into expandable element 530 (e.g. ablative fluid 145 provided by console 100). Multiple tissue treatments are performed by repositioning functional assembly 500, which can further include contracting expandable element 530 to reposition functional assembly 500. Contact between the target tissue and functional assembly 500 can be accomplished using desufflation techniques to bring the tissue toward expandable element 530 and/or via expansion of expandable element 530. Tissue treatment is performed, such as by filling expandable element 530 with ablative temperature fluid and/or delivering any form of energy to the target tissue. In embodiments where catheter 200 is delivered over a guidewire, the guidewire can be retracted (e.g. at least retracted to a location proximal to the treatment element) prior to any tissue treatments (e.g. prior to any energy deliveries).

Multiple treatments can be performed by advancing or retracting functional assembly 500 and/or catheter 200. In some embodiments, functional assembly 500 is positioned at a distal location and a series of tissue treatments are performed, such as at least 3 tissue treatments performed in which catheter 200 is retracted approximately the length of the tissue contacting portion of functional assembly 500 such as to treat relatively contiguous, non-overlapping, full circumferential axial segments of the duodenum (e.g. where at least one submucosal tissue expansion is performed prior to each ablation or other treatment). Prior to each treatment, an assessment of adequate submucosal tissue expansion can be performed, as described herein. Also prior to each tissue treatment, confirmation of being away from (e.g. distal to) any non-target tissue marked and/or otherwise identified can be performed (e.g. by visualizing a previously placed marker 90). In some embodiments, a marker 90 is placed to avoid any damage to the ampulla of Vater. In some embodiments, after three axial segments of duodenal mucosa are treated (e.g. treated distally to proximally), an assessment of the linear distance between the most-proximal treatment segment and the ampulla of Vater is performed (e.g. one or more components of system 10 is used to determine the distance). If sufficient length is determined (e.g. the determined distance is above a threshold), additional (more proximal) axial tissue segments can be treated. During translation of catheter 200 over a guidewire, undesired movement of the guidewire is prevented or otherwise reduced by the operator.

In some embodiments, the system of the present inventive concepts (e.g. system 10 of FIG. 1) is configured to allow only one ablation per (pre-determined) time period, such as to prevent two ablations within the time period such as to prevent repetitive ablation in the same or at least similar (e.g. overlapping) portions of the GI tract (e.g. rapid treatment of similar treatment zones).

In some embodiments, the tissue treatment of Step 2250 should be completed within approximately 120 minutes or within approximately 60 minutes of the initiation of tissue expansion performed in Step 2220 and/or step 2225, such as within approximately 45 minutes, 30 minutes and/or 20 minutes. Performance of tissue treatment within this time window prevents an unacceptable amount of injectate 125 from dissipating beyond the expanded submucosal tissue space (e.g. prevents an insufficient amount of submucosal tissue expansion being present during the tissue treatment). In some embodiments, system 10 is configured to prevent a tissue treatment (e.g. ablation) until an adequate submucosal expansion step has been performed and/or confirmed, such as is described in Step 2230. After one or more axial segments of duodenum or other GI segment is ablated in Step 2250, a determination is made in Step 2260 regarding additional axial segments to be treated. In some embodiments, a single axial segment is ablated in Step 2250, after which additional submucosal tissue is expanded (e.g. in one or more of Steps 2220 and/or 2225) and an additional ablation is performed proximate the additionally expanded submucosal tissue. In some embodiments, two axial segments of submucosal tissue are expanded for each single axial segment of mucosal tissue ablated. In some embodiments, a first ablation is performed proximate an area of two submucosal expansions (e.g. directly after the two submucosal expansions are performed), and subsequent ablations are performed after (e.g. directly after) two or less (e.g. one)

submucosal expansions are performed (e.g. expansions performed in the area of the subsequent ablations).

The cumulative amount of target tissue treated and/or the number of treatments performed can correlate to (e.g. be proportional to) one or more patient conditions (e.g. more severe correlates to more tissue treated and/or more treatments performed over time). This increased treatment can comprise an increased axial length of tissue treated (e.g. an increased cumulative axial length of duodenum ablated), an increased volume of tissue treated (e.g. an increased volume of duodenal mucosa treated via an increased mucosal surface area receiving ablation energy from functional assembly 500), a deeper depth of treatment, and/or a larger number of treatments performed over time in order to achieve a sustained treatment response. In some embodiments, the tissue treatment is modified to avoid creation of a duodenal stenosis or stricture, such as to limit one or more of: amount of energy delivered; peak energy delivered; duration of energy delivered; length of tissue treated; depth of tissue treated; and combinations of these.

Figure 2:
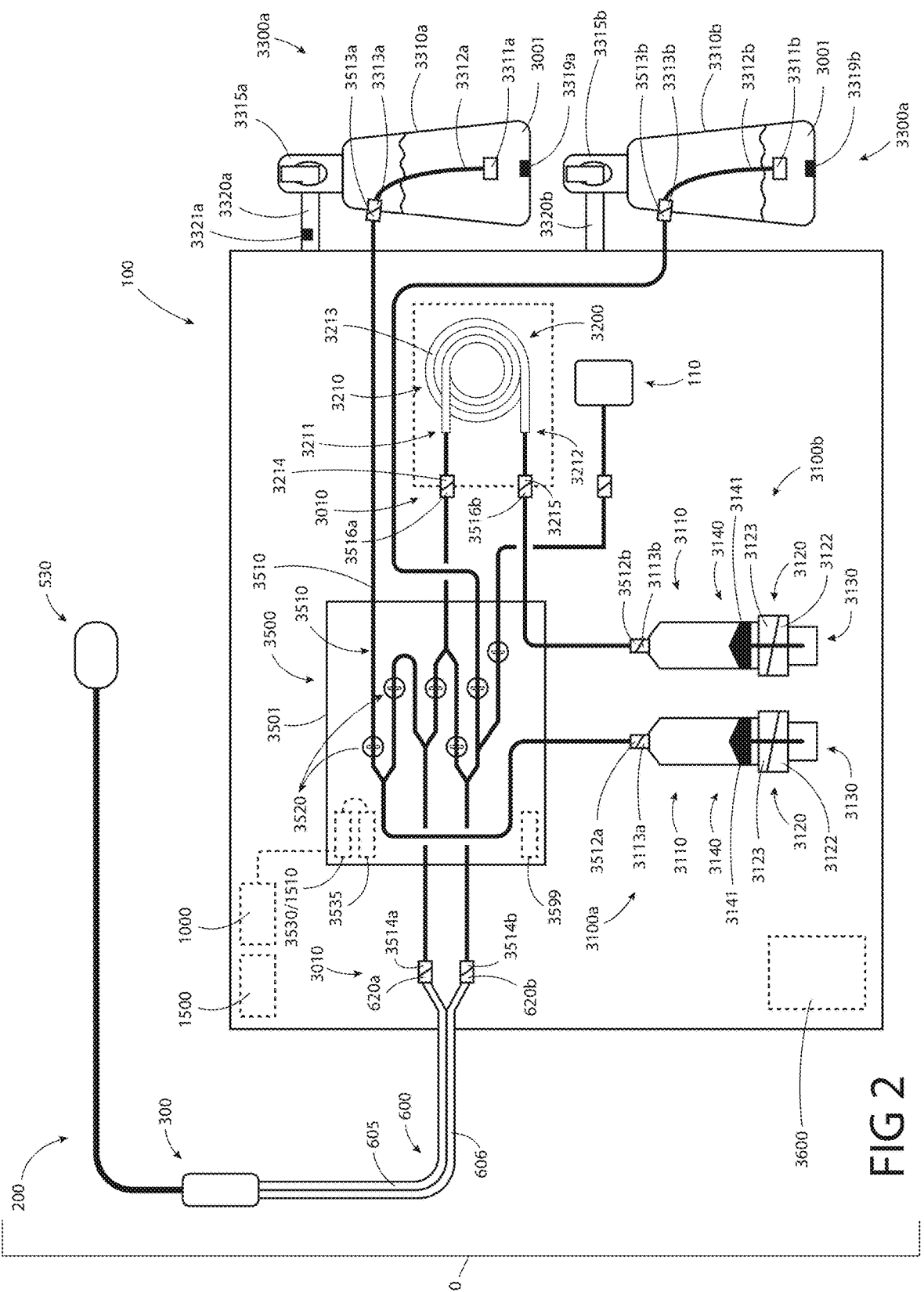
FIG. 2 illustrates a schematic view of a tissue treatment system including an elongate device, and a console with a cartridge, syringe pump assemblies, and fluid reservoirs attachable thereto, consistent with the present inventive concepts.

Referring now to FIG. 2, a schematic view of a tissue treatment system including an elongate device, and a console with a cartridge, syringe pump assemblies, and fluid reservoirs attachable thereto, is illustrated, consistent with the present inventive concepts. System 10 includes console 100 and a treatment device, catheter 200. A tubing set, umbilical 600 operably attaches catheter 200 to console 100. In some embodiments, console 100 includes an operator attachable fluid-pathway connection assembly, cartridge 3500. For example, cartridge 3500 can be attachable to console 100 by an operator of system 10 prior to a tissue treatment procedure performed using catheter 200. In some embodiments, console 100 can be configured to be used (e.g. sequentially used) with two or more cartridges 3500, umbilicals 600, and/or catheters 200, such as when console 100 comprises reusable capital equipment. The components described in reference to FIG. 2 are constructed and arranged to control, direct, manage, and/or otherwise manipulate ("control", "direct", "manage" or "manipulate" herein) a fluid, fluid 3001, such as to provide the fluid to an expandable element, element 530 shown, such as to treat tissue (e.g. mucosal tissue of the GI tract) proximate expandable element 530 (similar to as is described herein in reference to FIG. 1). Fluid 3001 can be similar to ablative fluid 145, neutralizing fluid 155, and/or functional fluid 185, each described herein in reference to FIG. 1.

Console 100 can comprise one or more heating assemblies, assembly 3200. In some embodiments, heater assembly 3200 comprises an inline heater, heater 3210. Heater 3210 can comprise a first port 3211 and a second port 3212, fluidly connected by lumen 3213. Heater 3210 can be configured to heat fluid 3001 as it flows through lumen 3213, either flowing from port 3211 to port 3212 and/or flowing from port 3212 to port 3211 (e.g. heater 3210 can support bidirectional flow of fluid). In some embodiments, heater 3200 is configured to be pre-heated (e.g. the heating elements, the heater body, and/or other fluid contacting portions are pre-heated) prior to a heating step in which fluid 3001 is passed through heater 3200 (e.g. prior to an ablation). Heater 3200 can be pre-heated to improve the temperature response of the system (e.g. decrease the time it takes fluid 3001 to reach a target temperature). In some embodiments, heater 3200 can be pre-heated (e.g. heated to a desired pre-heat temperature) between heating steps, such as between ablations. In some embodiments, system 10 comprises a closed-loop control algorithm (e.g. a control algorithm for a PID controller of system 10), that can be configured to adjust the power of heater 3200 in a closed-loop arrangement to achieve a desired temperature of fluid 3001. For example, each system 10 manufactured can comprise a closed-loop control algorithm (e.g. the same closed-loop control algorithm) that can result in minimizing variations in heating performance of heater 3200 from one system 10 to another (e.g. variations caused by manufacturing variability).

System 10 can comprise one or more vacuum supplies, vacuum supply 110 shown and as described herein. In some embodiments, vacuum supply 110 comprises a source of vacuum provided by console 100. Alternatively or additionally, console 100 can be configured to attach to a source of vacuum provided within a hospital room, such as a surgical suite that includes one or more attachment locations for attachment to a vacuum supply. In some embodiments, console 100 is configured to check (e.g. via a pressure sensor or other sensor) for the presence of a sufficient level of vacuum pressure prior to one or more steps of a treatment procedure being performed, as described herein.

System 10 can comprise one or more reservoir assemblies, reservoir assemblies 3300a and 3300b shown (singly or collectively reservoir assembly 3300 herein). Each reservoir assembly 3300 can be similar or dissimilar, such as when comprising one or more similar or dissimilar components described herein. Reservoir assembly 3300 can comprise a chamber, reservoir 3310, configured to store fluid 3001, provide fluid 3001 to, and/or receive fluid 3001 from, console 100. In some embodiments, reservoir 3310 comprises a flexible housing (e.g. a softened polyvinyl chloride or other flexible material arranged in a bag-like construction). Reservoir assembly 3300 can include an attachment mechanism, handle 3315. Handle 3315 can be attached to reservoir 3310 and it can be configured to attach reservoir 3310 to console 100. In some embodiments, console 100 comprises one or more attachment mechanisms, hooks 3320a and 3320b shown (singly or collectively hooks 3320 herein). Hooks 3320 can be configured to engage handles 3315 such that reservoirs 3310 can be removably attached to the side of console 100. Alternatively or additionally, console 100 can comprise one or more recesses configured to slidingly receive reservoir assemblies 3300, and/or reservoir assemblies 3300 can be fixedly attached to console 100 (e.g. fixedly attached but removable by a technician or operator of console 100). In some embodiments, console 100 and/or hook 3320 comprises a sensor, sensor 3321, which can be configured to monitor a fluid level within reservoir 3310. For example, sensor 3321 can comprise a load cell or other weight sensing device that is configured to determine the fluid level within reservoir 3310 based on the current weight of reservoir 3310 and the fluid it surrounds. Reservoir assembly 3300 can comprise one or more functional elements, functional element 3319. In some embodiments, functional element 3319 comprises a fluid level sensor configured to monitor the level (e.g. the volume or weight) of fluid 3001 within reservoir 3310. In some embodiments, functional element 3319 comprises a temperature sensor, such as a temperature sensor configured to be electrically, optically, and/or otherwise operatively connected to console 100. In some embodiments, console 100 comprises an infrared temperature sensor configured to measure the temperature of fluid within reservoir 3310.

Reservoir assembly 3300 can comprise an intake manifold, intake 3311, which can be fluidly attached to a lumen, intake lumen 3312. Intake lumen 3312 can be fluidly attached to a connector, connector 3313. In some embodiments, connector 3313 is "integral to" (e.g. molded into and/or otherwise fixedly attached to) the wall of reservoir

3310. Alternatively or additionally, lumen 3312 can extend from inside reservoir 3310 to outside reservoir 3310 (e.g. through a fluid tight seal), such that a portion of lumen 3312 extends outside of reservoir 3310 and fluidly attaches to connector 3313 (e.g. in a pigtail arrangement). Connector 3313 can be configured to fluidly attach to a connector of cartridge 3500 as described herein. In some embodiments, connector 3313 is integral to reservoir 3310 and positioned near the top of reservoir 3310, and lumen 3312 and/or intake 3311 are not included, such that fluid provided to connector 3313 is delivered directly into reservoir 3310 (e.g. when reservoir 3310 comprises a "waste" reservoir, and fluid is delivered to reservoir 3310 but not delivered from reservoir 3310).

Console 100 can comprise one or more syringe pump assemblies 3100, such as syringe pump assemblies 3100a and 3100b shown (singly or collectively syringe pump assembly(s) 3100 herein). In some embodiments, console 100 comprises no more than two syringe pump assemblies 3100. Each syringe pump assembly 3100 can be similar or dissimilar to another, such as when assembly 3100 comprises one or more similar or dissimilar components described herein. Syringe pump assembly 3100 can comprise a syringe 3110, with a first connector 3113 at the tip of syringe 3110, and a second connector 3123 at the base of syringe 3110. Second connector 3123 can mate with a connector of console 100, connector 3122. Connectors 3122 and 3123 form connector assembly 3120. Connector assembly 3120 is configured to enable syringe 3110 to operably and removably connect to console 100. Connector assembly 3120 can be configured as described in reference to FIGS. 5A-5C herein. Syringe pump assembly 3100 can further comprise syringe drive assembly 3130, wherein assembly 3130 can be configured to actuate a plunger assembly 3140 comprising a plunger 3141. Plunger 3141 can be retracted and/or advanced within syringe 3110, drawing fluid into syringe 3110 and/or forcing fluid from syringe 3110, respectively. In some embodiments, each syringe 3110 comprises a maximum volume (e.g. the maximum volume of fluid the syringe can hold) of 500 mL, such as 300 mL, 200 mL, or 150 mL.

Cartridge 3500 can be configured to operably attach to console 100. Cartridge 3500 can comprise a housing 3501, where housing 3501 surrounds at least a portion of one or more conduits (e.g. fluid carrying conduits), conduits 3510 shown. Conduits 3510 can extend beyond housing 3501, each terminating in a connector 3010 and configured to fluidly attach to a corresponding connector as described herein. In some embodiments, one or more of connectors 3010 comprise rotatably locking fluid connectors, such as a connector that includes an O-ring seal, twists to lock in one quarter of a turn, allows attached tubing to rotate freely, and/or provides a tactile and/or audible feedback when properly connected. In some embodiments, connectors 3010 can be similar to connectors from the SMC Series of subminiature couplings provided by Colder Products Company of St. Paul, Minnesota. Connectors 3010 can comprise connectors 620, 3514, 3512, 3113, 3516, 3214, 3215, and/or other connectors described herein. Cartridge 3500 can comprise one or more valves and/or other fluid control elements, valve assemblies 3520. Valve assemblies 3520 can be configured to manipulate the geometry of the walls of conduits 3510 (e.g. to pinch the walls of conduits 3510) such as to control the routing of fluid through cartridge 3500. The various conduits 3510 and connectors 3010 of cartridge 3500 fluidly attach to reservoir assemblies 3300, vacuum supply 110, heater assembly 3200, syringe pump assemblies 3100, and catheter 200 via umbilical 600, such as to enable the routing of fluid from reservoir assembly 3300a, through the various components of system 10, and to reservoir assembly 3300b. Valve assemblies 3520 can be configured as described in reference to FIGS. 9A-D herein.

In some embodiments, one or more of connectors 3010 are integral to the wall of housing 3501, integral connector 3010ᵢ, of cartridge 3500. For example, in some embodiments, conduit 3510 fluidly attaches to one side of integral connector 3010ᵢ within housing 3501, a portion of integral connector 3010ᵢ extends through housing 3501, and the opposite side of integral connector 3010ᵢ extends from housing 3501 (e.g. providing a fluid connection to another component of system 10). In some embodiments, at least a portion of the integral connector 3010ᵢ is rotationally fixed relative to cartridge 3500, such that an operator of system 10 can attach a mating connector 3010 to the integral connector 3010ᵢ by twisting the mating connector 3010 relative to a portion of cartridge 3500, for example in a single-handed operation. In some embodiments, an integral connector 3010ᵢ is fixedly attached to housing 3501 with a friction fit (e.g. a press fit between a flange of connector 3010ᵢ and a portion of an attached conduit 3510), without the use of an adhesive. In some embodiments, connectors 3010ᵢ are configured as described in reference to FIG. 4 herein.

Conduits 3510 can be constructed and arranged to withstand, without adverse effect, various functional conditions that may occur during the operation of system 10. For example, conduits 3510 can comprise a radial stiffness sufficient to withstand (e.g. withstand without collapsing) a vacuum pressure of at least −1 psi, such as at least −3 psi, such as at least −7 psi, such as −14.7 psi. Additionally or alternatively, conduits 3510 can comprise a radial stiffness low enough to fully collapse (e.g. collapse to an occlusion condition) when a valve assembly 3520 comprising a pinch valve applies a compression force to a conduit 3510 to stop or otherwise reduce the flow of fluid therethrough. In some embodiments, conduits 3510 comprise materials capable of withstanding (e.g. without permanent deformation) heat of at least 60° C., such as at least 80° C., or at least 100° C. Conduits 3510 can comprise a construction that is sufficient to achieve a burst pressure of at least 20 psi, such as at least 50 psi, such as at least 100 psi, such as at least 200 psi. In some embodiments, system 10 is configured to detect (e.g. via one or more sensors and/or algorithms of system 10) a condition in which a valve assembly fails to sufficiently collapse (e.g. pinch off) a conduit (e.g. to detect a condition in which valve assembly 3520 fails to fully collapse a conduit 3510). Once system 10 detects such an undesired condition, system 10 can enter an alert state (e.g. a state in which the operator is notified, and delivery of ablation energy can be stopped and/or modified).

Figure 6:
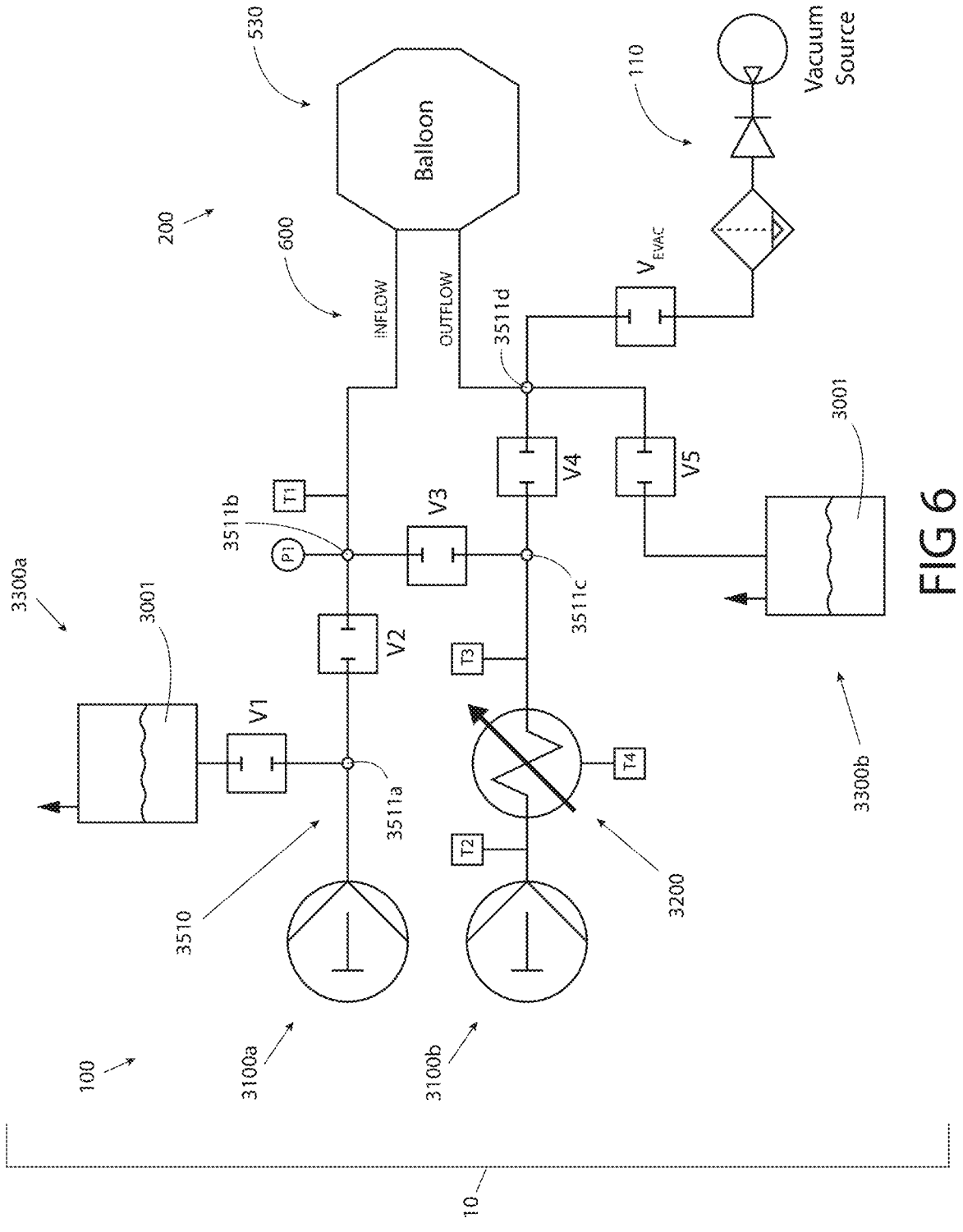
FIG. 6 illustrates a schematic view of a fluid pathway of a tissue treatment system, consistent with the present inventive concepts.

In some embodiments, console 100 and its associated components are configured as illustrated in FIG. 6, and fluid 3001 is routed through system 10 as described herein in reference to FIGS. 6A-6F.

In some embodiments, two conduits 3510 extend from housing 3501 and terminate in connectors 3512a and 3512b, shown. Connectors 3512a,b are each configured to operably attach to first connectors 3113a,b, respectively of syringe pump assemblies 3100. Connectors 3512 and 3113 can comprise connectors configured to operably (e.g. lockingly and fluidly) connect to each other. Connectors 3512 and 3113 can be configured to form a locked and/or otherwise secured connection by rotation of at least a portion of a connector 3512 relative to a connector 3113, such as by a rotation of less than 360°, such as less than 180°. Connectors 3512 and 3113 can be configured to provide tactile and/or audible (e.g. a clicking sound) feedback to the operator to confirm a proper connection has been made (e.g. sufficient rotation and/or engagement has been achieved). In some embodiments, connector 3512 can be integral to syringe 3110. Syringe 3110 can be rotationally fixed relative to console 100, such that an operator of system 10 can attach connector 3512 to connector 3113 by twisting connector 3512 relative to syringe 3110, for example in a single-handed operation (e.g. due to the integral construction of connector 3512 to syringe 3110). In some embodiments, connectors 3512 and 3113 comprise rotatably locking fluid connectors, such as rotatably locking fluid connectors described herein.

In some embodiments, two conduits 3510 extend from housing 3501 and terminate in connectors 3516a and 3516b, shown. Connectors 3516a,b are each configured to operably attach to connector 3214 that is fluidly attached to first port 3211, and connector 3215 that is fluidly attached to second port 3212 of heater assembly 3200, respectively. Connectors 3516a,b and 3214 and 3215 can comprise connectors configured to operably connect to each other. Connectors 3516a,b and 3214 and 3215 can be similar to other connectors 3010 described herein. In some embodiments, connectors 3214 and/or 3215 can be integral to a wall of console 100 (e.g. integral to a wall of a housing of console 100). At least a portion of connector 3214 and/or 3215 can be rotationally fixed relative to console 100, such that an operator of system 10 can attach connectors 3516a,b to connector 3214 or 3215, respectively, by twisting at least a portion of connector 3516a,b relative to connector 3214 or 3215, for example in a single-handed operation.

In some embodiments, two conduits 3510 extend from housing 3501 and terminate in connectors 3514a and 3514b, shown. Connectors 3514a,b are each configured to operably attach to connectors that are attached to the proximal end of umbilical 600, connectors 620a,b, respectively. In some embodiments, connector 620a is fluidly attached to an inflow lumen of umbilical 600, lumen 605, and connector 620b is fluidly attached to an outflow lumen of umbilical 600, lumen 606. In some embodiments, lumens 605 and 606 be defined by a shaft with two conduits configured in a side by side arrangement, such as a shaft formed from a single extrusion. In some embodiments, the functional length of conduits 3510 between connector 3514a and connector 3516a (e.g. the conduits 3510 connecting first port 3211 of heater assembly 3200 and input lumen 605 of umbilical 600) comprises a length of less than 10", such as less than 8", such as approximately 6".

In some embodiments, console 100 further comprises injectate assembly 3600, which can comprise one or more fluid delivery assemblies configured to supply one or more injectates (e.g. injectate 125 described herein) to tissue via catheter 200. Injectate assembly 3600 can be similar or dissimilar to one or more components described herein, such as injectate fluid supply 120 described herein. In some embodiments, injectate assembly 3600 is configured as described in reference to FIG. 3 herein. Injectate assembly 3600 can comprise one, two, three, or more syringes fluidly attached to one, two, three, or more injectate delivery elements, such as injectate delivery elements 520 described herein.

In some embodiments, console 100 comprises controller 1500. Controller 1500 can be similar to controller 1500 described in reference to FIG. 1 herein. Console 100 can further comprise an electrical and/or mechanical connector, connector 1510. Connector 1510 can electrically and/or mechanically connect to a mating connector of cartridge 3500, connector 3530. Cartridge 3500 can further comprise an electronics module 3535 operably connected to connector 3530. Cartridge 3500 can comprise a functional element 3599. Functional element 3599 can comprise an element selected from the group consisting of: a pressure sensor; a temperature sensor; a flow sensor; an optical sensor; a transducer; an ID-providing element, such as an RF ID; an accelerometer; and combinations of these. In some embodiments, functional element 3599 is operably attached to electronics module 3535, which can be operably attached to controller 1500 via connectors 3530 and 1510.

In some embodiments, system 10 is configured to perform an operation to sterilize at least a portion of console 100, cartridge 3500, umbilical 600, and/or catheter 200. For example, console 100 can comprise one or more fluid contacting components, such as one or more fluid pathways and/or functional elements (e.g. sensors or heaters) which are to be sterilized prior to each treatment procedure. The ability to position high precision, costly components (e.g. sensors) proximate (e.g. within and/or near) re-sterilizable fluid pathways within console 100 allows the properties of fluids within those pathways to be monitored with a level of precision otherwise difficult to achieve using a detachable interface (e.g. between a disposable component and a sensor of console 100), while avoiding the cost of such components being included in a disposable portion of system 10 (e.g. cartridge 3500). Additionally, the ability to sterilize (or re-sterilize, for example, after a procedure has been performed) fluid contacting portions of high precision and costly functional elements of console 100 can mitigate the cost of such components being included in a disposable portion of system 10 (e.g. cartridge 3500). The ability to sterilize, or re-sterilize, resposable components of system 10 can also help to mitigate the cost of continued operation of system 10. System 10 can be configured in an operational state during which fluid is heated to a temperature of at least 85° C., such as at least 95° C., and that fluid is circulated throughout the portions of console 100 (or other components of system 10) that require sterilization. In some embodiments, the fluid pathways to be sterilized by system 10 do not comprise any "dead leg" lengths of greater than 1 inch, such as none greater than 0.5 inches (e.g. for 1/16 inch ID silicone tubing). Alternatively or additionally, any dead leg lengths of the fluid pathways to be sterilized can comprise conductive materials, such that the fluid pathway included in the dead leg length is sufficiently heated by the sterilization procedure to ensure sterilization of the dead leg. In some embodiments, the sterilization procedure can be similar to that as described in applicant's co-pending International PCT Patent Application Serial Number PCT/US2020/056627, entitled "Systems, Devices, and Methods for Performing Medical Procedures in the Intestine", filed Oct. 21, 2020, the content of which is incorporated herein by reference in its entirety for all purposes.

In some embodiments, system 10 is configured to perform a low-level disinfection of at least a portion of console 100, cartridge 3500, umbilical 600, and/or catheter 200 (e.g. the reusable components of these). Alternatively or additionally, system 10 can be configured to perform a high-level disinfection of one or more of these components. In some embodiments, system 10 is configured to heat at least a portion of these components to at least 90° C., such as at least 93° C., at least 95° C., at least 97° C., or at least 101° C., for a minimum time period, such as for at least 45 seconds, at least 60 seconds, and/or at least 90 seconds, and/or for a maximum time period, such as for no more than 3 minutes, no more than 4 minutes, and/or no more than 5 minutes.

In some embodiments, one or more (e.g. all or at least a majority) of the fluid connections of system 10 described herein are made prior to use in a clinical setting (e.g. at least a majority of the fluid connections of system 10 are made during the manufacturing process), such that an operator of system 10 is required to make minimal fluid connections (e.g. none) prior to use, such as less than 5 fluid connections, less than 3 fluid connections, or less than one fluid connection.

In some embodiments, system 10 comprises one or more microcontrollers configured to control the various assemblies of the system. In some embodiments, various assemblies of system 10 each comprise a unique microcontroller, such as a microcontroller configured to control specific functions of that assembly. In some embodiments, one or more microcontrollers of system 10 function as servers, and one or more other microcontrollers of system 10 each function as a client. In some embodiments, the server microcontrollers monitor the client microcontrollers, such as to detect any issues with the client microcontrollers, such as to detect an issue and cause system 10 to enter a safe mode (e.g. a state in which operation is maintained but certain functions are limited) and/or other alert state. Alternatively or additionally, client microcontrollers can be configured to monitor a server microcontroller, and to enter a safe mode and/or other alert state if an error is detected with the server microcontroller. Each of syringe assembly 3100, valve assemblies 3520, heater assembly 3200, and/or other assemblies of system 10 can comprise a unique microcontroller (e.g. configured to monitor another microcontroller and/or be monitored by one or more microcontrollers).

In some embodiments, system 10 comprises one or more hardware-based (e.g. electromechanical) safety mechanisms for preventing fluid pressure from exceeding a safety threshold. For example, console 100 can comprise a load cell operably attached to syringe assembly 3100, where the load cell is configured to disconnect power from syringe assembly 3100 if a pressure threshold is reached (e.g. the force on the load cell exceeds a force threshold associated with a desired pressure threshold). Alternatively or additionally, console 100 can comprise an overpressure prevention mechanism selected from the group consisting of: an overpressure valve; a sheer nut on a linear drive mechanism; a clutch on a linear drive mechanism; a current limiter; and combinations of these.

In some embodiments, one or more assemblies of console 100 are provided to the user as multiples of the same assembly (e.g. two or more assemblies 3100 and/or 3200 are provided to the user). In these embodiments, console 100 can be configured such that the user can replace a first provided assembly (e.g. provided at the time of delivery of console 100) with a second provided assembly (e.g. provided as an extra at the time of delivery of console 100 or at a time subsequent to that). The replacement can be performed to replace a broken first assembly, and/or to provide an upgrade to console 100 via the installation of the second assembly. The one or more replaceable assemblies (e.g. assemblies 3100 and/or 3200) can be operably attached to console 100 using hooks, latches, and/or locks. In some embodiments, one or more sensors of console 100 can be configured to confirm acceptability of the replacement, such as to confirm acceptability of software and/or hardware associated with the replacement, and/or to confirm proper attachment of the new assembly. If an unacceptable replacement is made (e.g. as detected by the sensor), system 10 (e.g. console 100) can enter an alert state.

In some embodiments, system 10 is configured to be operated at a pressure at or above the boiling point of fluid 3001, based on the altitude at which the procedure is being performed.

Referring now to FIG. 3, a schematic view of another tissue treatment system including an elongate device, and a console with a cartridge, syringe pump assemblies, and fluid reservoirs attachable thereto, is illustrated, consistent with the present inventive concepts. Console 100, catheter 200, and/or other components of system 10 of FIG. 3 can be of similar construction and arrangement to those described in reference to other figures described herein. The schematic shown illustrates fluid connections between catheter 200, console 100, and cartridge 3500.

Catheter 200 can comprise one, two, or more tissue capture chambers, such as three tissue capture chambers 510a-c shown, each fluidly attached to connector 321. In some embodiments, each tissue capture chamber 510a-c connects to a unique connector 321, such that each tissue capture chamber 510a-c can fluidly attach to a vacuum source independently (e.g. when each unique connector 321 is fluidly attached to a source of vacuum). Alternatively, as described herein, each tissue capture chamber 510a-c connect to the same connector 321, such that vacuum is applied to each tissue capture chamber 510a-c when connector 321 is fluidly attached to a source of vacuum. In some embodiments, catheter 200 comprises one, two, or more ports, such as ports $470_P$ and $470_D$ shown (e.g. a port positioned proximal to and distal to expandable element 530, respectively). In some embodiments, each port $470_P$, $470_D$ connects to a unique connector 322, such that each port $470_P$, $470_D$ can fluidly attach to a vacuum source independently. Alternatively, as described herein, each port $470_P$, $470_D$ can connect to the same connector 322, such that vacuum is applied to each port $470_P$, $470_D$ when connector 322 is fluidly attached to a source of vacuum (e.g. an aspiration canister).

Cartridge 3500 can comprise connectors, conduits, and/or valves which fluidly connect to connectors 321 and 322 to vacuum assembly 110. Cartridge 3500 can comprise connectors 3517 and 3518, which fluidly connect to connectors 321 and 322, respectively, of catheter 200. Cartridge 3500 can comprise connector 3519, which fluidly connects to connector 112 of vacuum assembly 110. A valve for controlling the application of vacuum pressure to ports $470_P$ and $470_D$, valve $V_A$, can be positioned in-line between connectors 3518 and 3519. A valve for controlling the application of vacuum pressure to tissue capture chambers 510a-c, valve $V_S$, can be positioned in-line between connector 3517 and 3519. A valve for controlling the venting of tissue capture chambers 510a-c to atmospheric pressure (e.g. room pressure), valve $V_V$, can be positioned between connector 3517 and a vent that is open to the pressure of the external environment, such as the atmospheric pressure of a procedure room. In some embodiments, console 100 includes a positive pressure source (not shown), but operably connected to a port of catheter 200 (e.g. ports $470_P$ and/or $470_D$), such that an insufflation procedure can be performed. Alternatively or additionally, an endoscope can be used in conjunction with catheter 200 during a procedure, and insufflation and/or aspiration can be performed proximate expandable element 530 using the endoscope.

Catheter 200 can comprise one, two, or more injectate delivery elements, such as three injectate delivery elements 520a-c shown, each fluidly attached to a connector 327a-c, respectively. In some embodiments, each injectate delivery element 520a-c is fluidly attached to respective connector 327a-c via a conduit including a one-way valve (e.g. a one-way check valve) configured to allow fluid to flow in a single direction from connectors 327a-c to injectate delivery elements 520a-c, respectively. Each connector 327a-c can additionally be fluidly connected to a fourth connector, connector 326. In some embodiments, each connector 327a-c is fluidly attached to connector 326 via a conduit including a one-way valve (e.g. a one-way check valve), configured to allow fluid flow in a single direction from connector 326 to connectors 327a-c. System 10 can comprise one, two, or more injectate syringes, such as three syringes 3610a-c shown. Each syringe 3610 can fluidly connect to a connector 327a-c, respectively. In some embodiments, each syringe 3610 comprises an integral connector, such as a rotatably locking connector that operably connects to a matching rotatably locking connector, such as when connectors 327a-c comprise rotatably locking fluid connectors such as are described herein. System 10 can further comprise injectate supply 120, which can be fluidly connected to connector 326 via a mating connector 3621. As shown in FIG. 3, the one-way valves positioned between injectate delivery elements 520a-c, connectors 327a-c, and connector 326, are configured to enable syringes 3610a-c to both draw injectate 125 from injectate supply 120 (e.g. filling the syringes as the plungers of the syringes are withdrawn), and also to deliver injectate 125 to injectate delivery elements 520 (e.g. when the plungers of the syringes are advanced), without the need to change the fluid connections between these elements. Alternatively or additionally, syringes 3610a-c can be prefilled with injectate 125, and/or syringes 3610a-c can be filled and/or refilled with injectate 125 by automated and/or manual changes to the fluid pathway connections of injectate assembly 3600.

Catheter 200 can comprise an expandable element 530, fluidly attached to a first lumen, inflow lumen 265, and a second lumen, outflow lumen 266. Lumens 265 and 266 can extend from expandable element 530, proximally along the shaft of catheter 200 to the handle of catheter 200, each terminating in a connector, connectors 330a and 330b, respectively. Connectors 330a and 330b each fluidly connect to connectors 630a and 630b of umbilical 600, respectively. Umbilical 600 can comprise two lumens, inflow lumen 605 and outflow lumen 606, each extending between connectors 630a and 620a, and 630b and 620b, respectively.

Cartridge 3500 can include connectors 3512a,b, 3513a,b, 3514a,b, and 3516a,b. These connectors can be similar to those described in reference to other figures herein, for example as described in FIG. 2 herein. These connectors can be fluidly interconnected via a network of conduits and valves as illustrated and described herein. Connectors 3513a,b connect to connectors 3313a,b, respectively, fluidly attaching the network of conduits of cartridge 3500 to reservoirs 3310a,b, respectively. In some embodiments, reservoir 3310a and/or reservoir 3310b comprise a vent, such as to allow the pressure within the reservoir to equalize to room pressure as fluid is added to and/or removed from the reservoir. Connectors 3512a,b connect to connectors 3113a,b, respectively, fluidly attaching the network of conduits of cartridge 3500 to syringes 3110a,b, respectively. Connectors 3514a,b connect to connectors 620a,b, respectively, fluidly attaching the network of conduits of cartridge 3500 to umbilical 600, and thereby connecting to expandable element 530. Connectors 3516a,b connect to connectors 3214 and 3215, respectively, fluidly attaching the network of conduits of cartridge 3500 to heater assembly 3200 of console 100. Valves V1-V5 can be positioned inline within the network of conduits of cartridge 3500, as shown and as described herein.

In some embodiments, cartridge 3500 does not include a temperature sensor. Console 100 can include one or more temperature sensors, such as sensors T-1, T-2, T-3, and T-4 shown, and positioned proximate heater assembly 3200. In some embodiments, sensor T-1 is positioned at a first port of heater assembly 3200, and T-2 is positioned at a second port of heater assembly 3200 (e.g. ports 3211 and 3212, illustrated in FIG. 2). Sensors T-1 and T-2 can be configured to record the temperature of fluid entering and/or exiting the respective ports of heater assembly 3200. In some embodiments, sensor T-3 and/or T-4 are positioned on heater assembly 3200, such as to monitor the temperature of a portion of heater assembly 3200 and/or the fluid flowing through assembly 3200. In some embodiments, two or more of sensors T-1 through T-4 can be positioned such that the recorded values of the sensors can be analyzed by system 10 to confirm the functionality of one or more of the sensors T-1 through T-4. In some embodiments, cartridge 3500 comprises one or more pressure sensors, for example, sensors $PS_V$ and $PS_O$ shown. Sensor $PS_V$ can be positioned proximate connector 3519 and can monitor the level of vacuum at that location. Sensor $PS_V$ can be used by system 10 to confirm vacuum source 110 is properly connected and functioning before and/or during a procedure. Sensor $PS_O$ can be positioned proximate connector 3514a and can monitor the pressure of fluid leaving cartridge 3500 as it flows to expandable element 530. In some embodiments, cartridge 3500 does not include a pressure sensor. In some embodiments, console 100 comprises a pressure sensor configured to be fluidly attached (e.g. via a connection not shown) to a conduit of cartridge 3500, such as a conduit proximate and fluidly connected to connector 3519. In some embodiments, console 100 comprises a pressure sensor proximate connector 3214 configured to monitor the pressure of fluid leaving heating assembly 3200 as it flows to expandable element 530.

Figure 4:
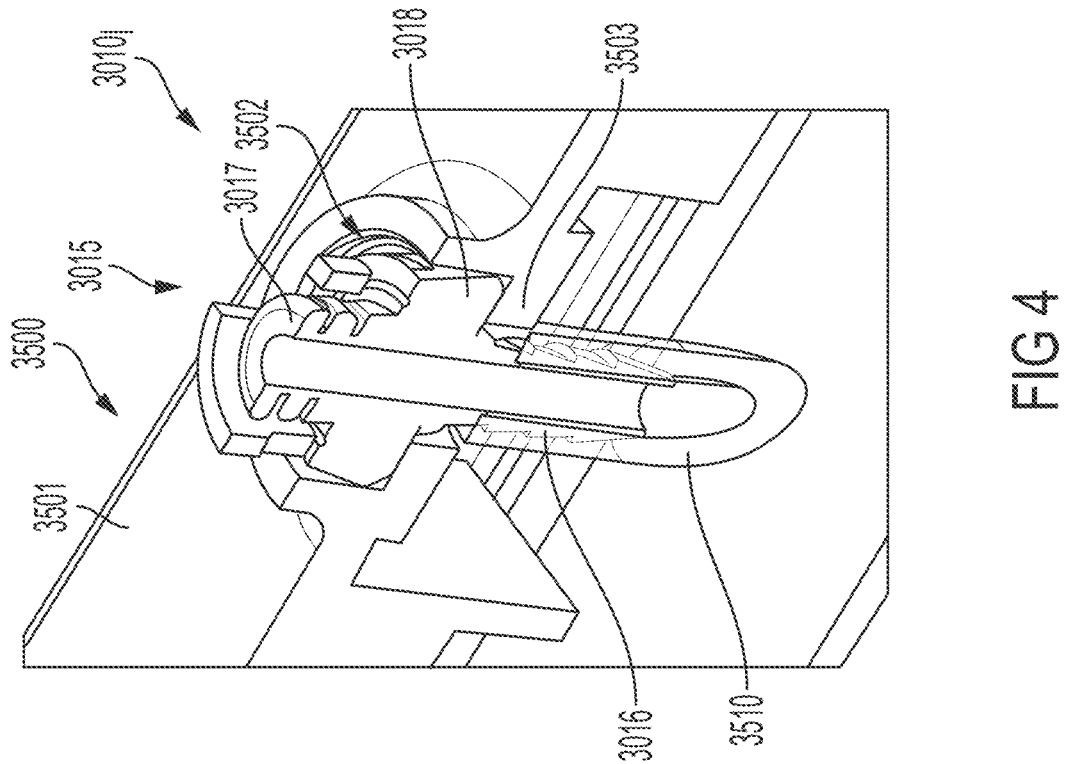
FIG. 4 illustrates a perspective sectional view of a portion of a cartridge, consistent with the present inventive concepts.

Referring now to FIG. 4, a perspective sectional view of a portion of a cartridge is illustrated, consistent with the present inventive concepts. Cartridge 3500 can comprise one or more integral connectors $3010_I$, such as are described herein. In some embodiments, at least a portion of one or more connectors $3010_I$ are fixedly attached to a wall of housing 3501 of cartridge 3500. For each integral connector $3010_I$, housing 3501 can comprise an opening, hole 3502. Hole 3502 can comprise a radial projection, rim 3503. Connector $3010_I$ includes a connecting member 3015, comprising a projection 3016, such as a barbed projection, on a first end, and a connecting element 3017, such as a locking connecting element, on an opposite end. Connecting element 3015 can comprise a projecting element, flange 3018, extending radially between projection 3016 and connecting element 3017. In some embodiments, connecting element 3017 can comprise a rotatably locking fluid connector, such as described herein. Connecting member 3015 can comprise a lumen extending between projection 3016 and connecting element 3017, such as to provide a fluid conduit through connecting member 3015.

In some embodiments, connector $3010_I$ is assembled (e.g. in a manufacturing process) by inserting connecting member 3015 through hole 3502, as shown. A conduit 3510 is slidingly received over projection 3016, such that housing 3501 (e.g. a portion of rim 3503) is captured between the end of conduit 3510 and flange 3018, thereby securing connecting member 3015 within hole 3502. In some embodiments, connecting member 3015 is secured within hole 3502 via frictional engagement, without the use of glue or other adhesive elements.

Figures 5A, 5B, 5C:
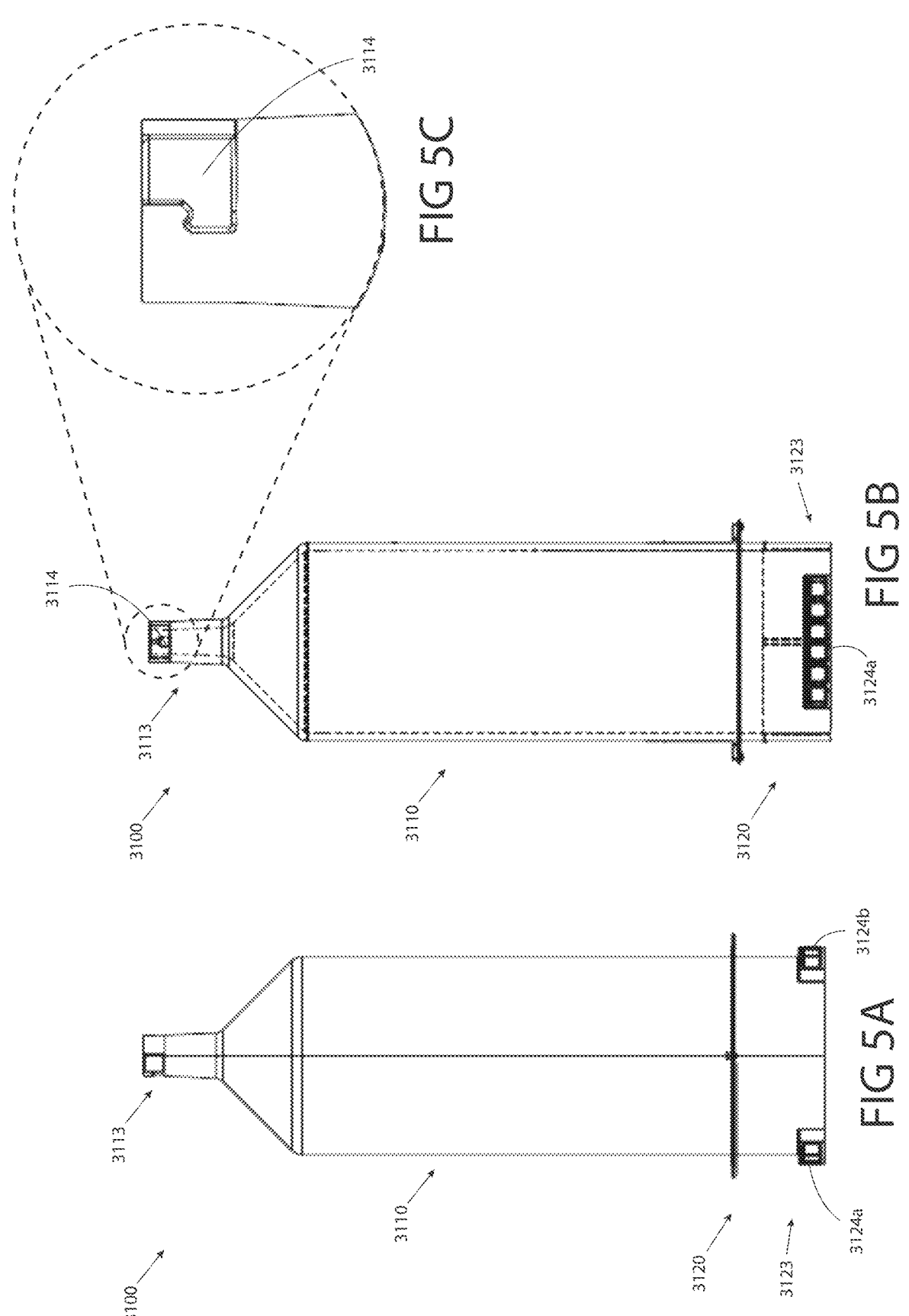
FIGS. 5A-5C illustrate two side views and a magnified side view of a syringe pump assembly, respectively, consistent with the present inventive concepts.

Referring now to FIGS. 5A-5C, two side views and a magnified side view of a syringe pump assembly are illustrated, respectively, consistent with the present inventive concepts. FIG. 5B illustrates the syringe 3110 of FIG. 5A that has been rotated 90°. FIG. 5C illustrates a magnified view of the tip of syringe 3110. As described herein, syringe pump assembly 3100 can comprise a syringe 3110, with a first connector 3113 at the tip of syringe 3110, and a second connector 3123 at the base of syringe 3110. Connector 3123 can comprise one or more connecting elements, flanges 3124a and 3124b shown. Flanges 3124a,b can be configured to releasably attach to a mating portion of connector assembly 3120, such as connector 3122 of console 100, not shown but described herein. For example, syringe 3110 can be configured to rotate (e.g. rotated by an operator of system 10) to lockingly engage with connector 3122. In some embodiments, connector assembly 3120 is configured to provide user feedback when a proper connection has been made, for example a haptic feedback or an audible feedback such as a click. As shown in FIG. 5C, connector 3113 can include a locking feature, projection 3114. Projection 3114 can be configured to lockingly engage with a mating connector, for example similar to a rotatably locking connector described herein. In some embodiments, system 10 is configured to detect when a syringe 3110 has been properly attached to console 100 (e.g. via one or more sensors of console 100). Alternatively or additionally, system 10 can be configured to detect if a syringe 3110 has been improperly and/or incompletely attached to console 100, and system 10 can be configured to enter an alert mode if an incorrect attachment has been detected, such as to alert an operator of the system.

Referring now to FIG. 6, a schematic view of a fluid pathway of a tissue treatment system is illustrated, consistent with the present inventive concepts. The valves, syringes, reservoirs, heaters, lumens, sensors, and other components described in reference to FIG. 6 are also described in reference to FIGS. 1 and C herein. FIG. 6 illustrates syringe pump assemblies 3100a and 3100b, heater assembly 3200, reservoir assemblies 3300a and 3300b, and vacuum source 110, each fluidly interconnected by one or more conduits 3510. Conduits 3510 are fluidly connected to expandable element 530 via inflow and outflow lumens of umbilical 600. In some embodiments, one or more connectors fluidly attach the various conduits of system 10, which in turn fluidly attach the associated components of FIG. 6. For illustrative clarity, these connectors are not shown in FIG. 6, but are described in detail in reference to FIG. 2 herein.

Five valve assemblies 3520 are illustrated, each configured to manipulate the flow of fluid 3001 through conduits 3510. In the embodiment of FIG. 6, conduits 3510 comprise fours junctions, junctions 3511a-d shown, each junction 3511 fluidly connecting three or more of the illustrated components. A first valve, valve V1 is positioned to control the flow of fluid 3001 between reservoir assembly 3300a and junction 3511a. Syringe pump assembly 3100a is also fluidly connected to junction 3511a. A second valve, valve V2 is positioned to control the flow of fluid 3001 between junctions 3511a and 3511b. The inflow conduit of umbilical 600 is fluidly connected to junction 3511b, such that junction 3511b is fluidly connected to expandable element 530. A third valve, valve V3 is positioned to control the flow of fluid 3001 between junctions 3511b and 3511c. Syringe pump assembly 3100*b* is fluidly connected to junction 3511*c* via heater assembly 3200. A fourth valve, valve V4 is positioned to control the flow of fluid 3001 between junctions 3511*c* and 3511*d*. The outflow conduit of umbilical 600 is fluidly connected to junction 3511*d*, such that junction 3511*d* is fluidly connected to expandable element 530. A fifth valve, valve V5 is positioned to control the flow of fluid 3001 between junction 3511*d* and syringe pump assembly 3300*b*. A sixth valve, valve V$_{EVAC}$ is positioned to control the flow of fluid 3001 between junction 3511*d* and vacuum source 110.

In some embodiments, valve V$_{EVAC}$ is normally open (e.g. in the open state when unpowered). Console 100 can be configured to provide power to valve V$_{EVAC}$ during normal operation of system 10, such as during the states described in reference to FIGS. 6A-6F described herein. In some embodiments, console 100 opens valve V$_{EVAC}$ in an alert state, such that vacuum source 110 is fluidly attached to conduits 3510, and draws fluid from within conduits 3510, and/or other fluidly connected components of system 10. For example, in the event of a power loss during a treatment step (e.g. a step in which expandable element 530 is fluidly attached to conduits 3510), the normally open valve V$_{EVAC}$ would open at the loss of power, fluidly connecting expandable element 530 to vacuum source 110, such that vacuum source 110 extracts fluid 3001 from expandable element 530. In some embodiments, conduits 3510 are not fluidly attached to vacuum source 110 (e.g. via valve V$_{EVAC}$), as described in reference to FIG. 6D herein. In some embodiments, one or more valves 3520 can comprise "fail in last" valves (e.g. valves configured to secure in their current state when a power failure occurs). In some embodiments, certain valves 3520 comprise normally open valves, normally closed valves, and/or fail in last valves, such that in any state of console 100, in the event of a power failure, any ablative fluid proximate the patient is automatically extracted. In some embodiments, console 100 can be configured to adjust the state of one or more valves 3250 based on the state of console 100 when a power loss occurs (e.g. using a backup power supply integral to console 100, not shown).

Referring now to FIGS. 6A-6F, schematic views of various operational states of system 10 are illustrated, consistent with the present inventive concepts. Console 100 can be configured to circulate fluid 3001 through expandable element 530 of catheter 200, such as to enable the various steps of a tissue treatment procedure, as described herein. In the operational modes described herein in reference to FIGS. 6A-6F, catheter 200 is operably attached (e.g. at least fluidly attached) to console 100 via umbilical 600, such as via connections described herein in reference to FIG. 2.

Figure 6A:
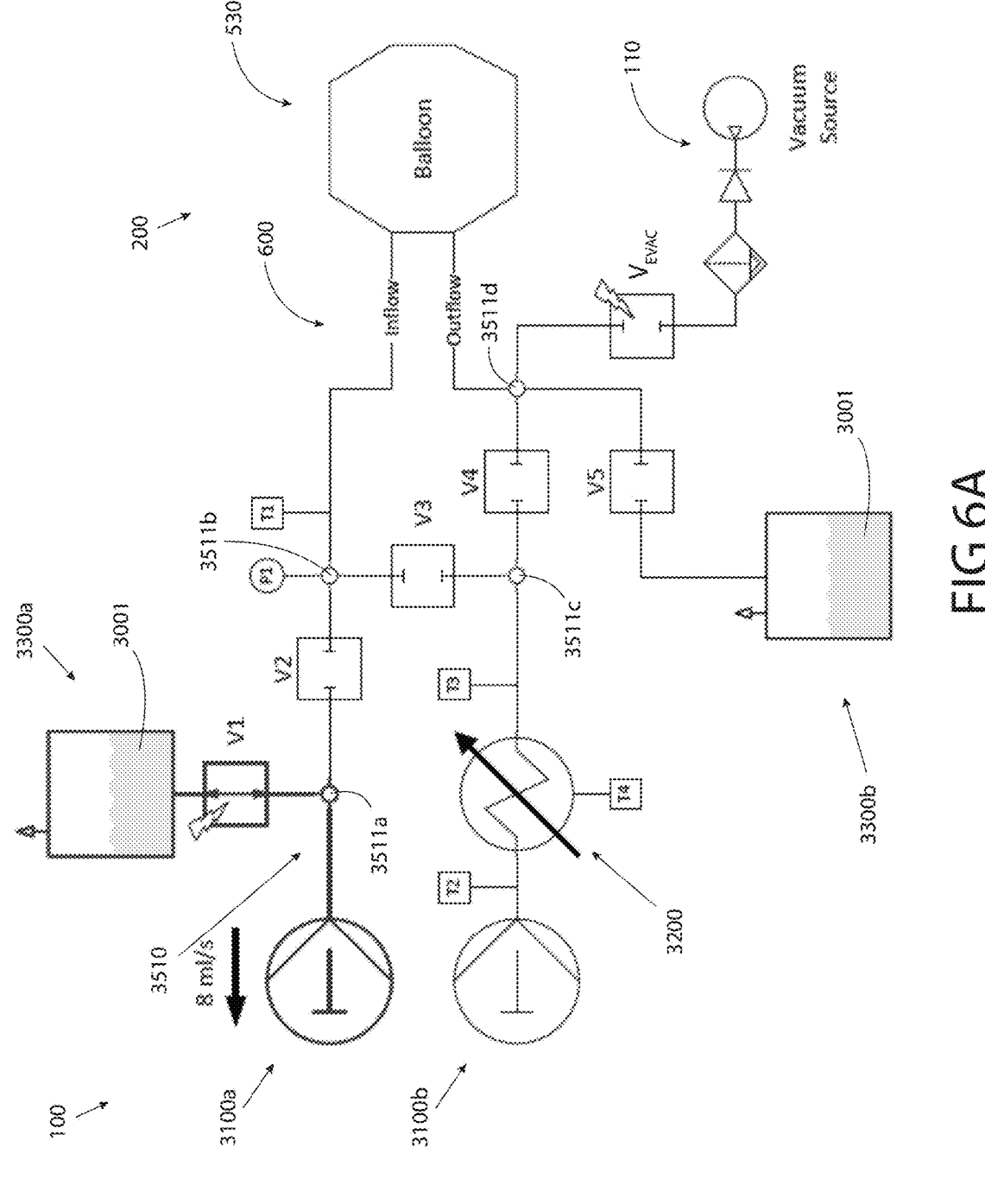
FIGS. 6A-6F illustrate schematic views of various operational states of system 10, consistent with the present inventive concepts.

Referring specifically to FIG. 6A, an operational state of system 10 associated with a first mode of operation, Mode F1, is illustrated, consistent with the present inventive concepts. In Mode F1, the plunger of syringe pump assembly 3100*a* is retracted, and valve V1 is opened such that fluid from reservoir 3300*a* is drawn into syringe pump assembly 3100*a*. Valve V2 is closed, such that syringe pump assembly 3100*a* is fluidly isolated from junction 3511*b*.

Figure 6B:
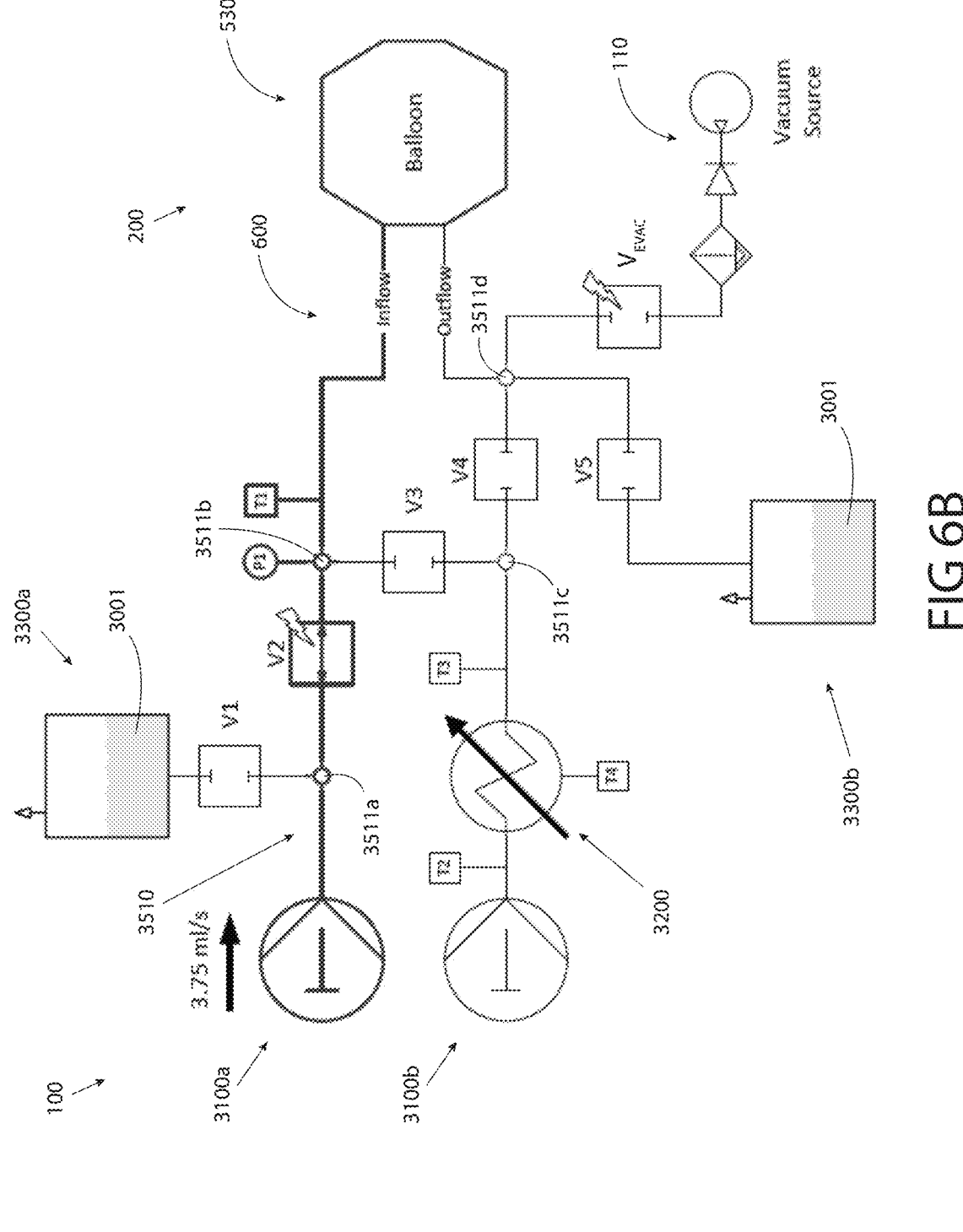

Referring specifically to FIG. 6B, an operational state of system 10 associated with a second mode of operation, Mode P1, is illustrated, consistent with the present inventive concepts. In Mode P1, valve V1 is closed, such that reservoir 3300 is isolated from junction 3511*a*, and valve V2 is opened such that syringe pump assembly 3100*a* is in fluid communication with expandable element 530 (via the inflow lumen of umbilical 600). Additionally, valves V3, V4, V5, and V$_{EVAC}$ are all closed. The plunger of syringe pump assembly 3100*a* is advanced, forcing the fluid 3001 drawn into syringe pump assembly 3100*a* in Mode F1 to flow through the inflow lumen of umbilical 600 to expandable element 530. Expandable element 530 is configured to expand from a first, compacted state, to a second, expanded state, as fluid 3001 fills the expandable element.

Figure 6C:
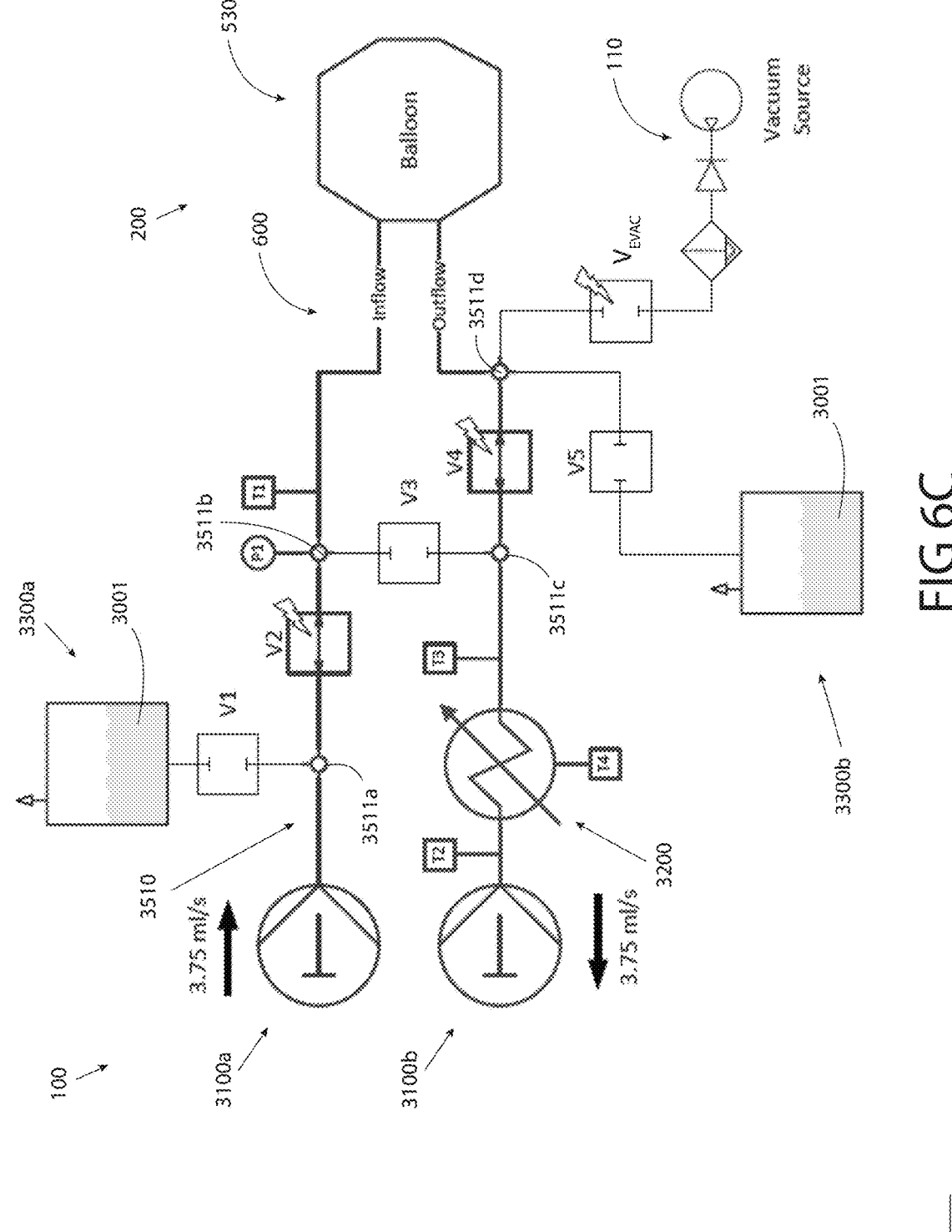

Referring specifically to FIG. 6C, an operational state of system 10 associated with a third mode of operation, Mode P2, is illustrated, consistent with the present inventive concepts. In Mode P2, fluid 3001 continues to flow from syringe pump assembly 3100*a* to expandable element 530. Valve V4 is opened, such that syringe pump assembly 3100*b* is in fluid communication with expandable element 530 via heater assembly 3200. As fluid 3001 if delivered to expandable element 530 by syringe pump assembly 3100*a*, the plunger of syringe pump assembly 3100*b* is retracted, drawing fluid 3001 from expandable element 530. As fluid 3001 passes through heater assembly 3200 and into syringe pump assembly 3100*b*, heater assembly 3200 is active, heating fluid 3001 to a first temperature, such that syringe pump assembly 3100*b* fills with warmed fluid 3001W. As fluid 3001 is circulated through expandable element 530, fluid 3001 can provide a cooling effect to the tissue proximate expandable element 530. As described herein, the cooling effect of circulating fluid 3001 can pre-treat the tissue prior to a thermal ablative step, providing a benefit to the outcome of the ablative procedure.

In alternate embodiments, with expandable element 530 filled with a bolus of fluid 3001 (e.g. filled to a set pressure and/or a set volume), additional fluid 3001 is drawn from syringe pump assembly 3100*a*, through heater assembly 3200, and into syringe pump assembly 3100*b* (as described hereabove), without passing through expandable element 530. In this embodiment, the bolus of fluid 3001 within expandable element 530 provides a cooling effect to tissue prior to a thermal ablation described herein.

Figure 6D:
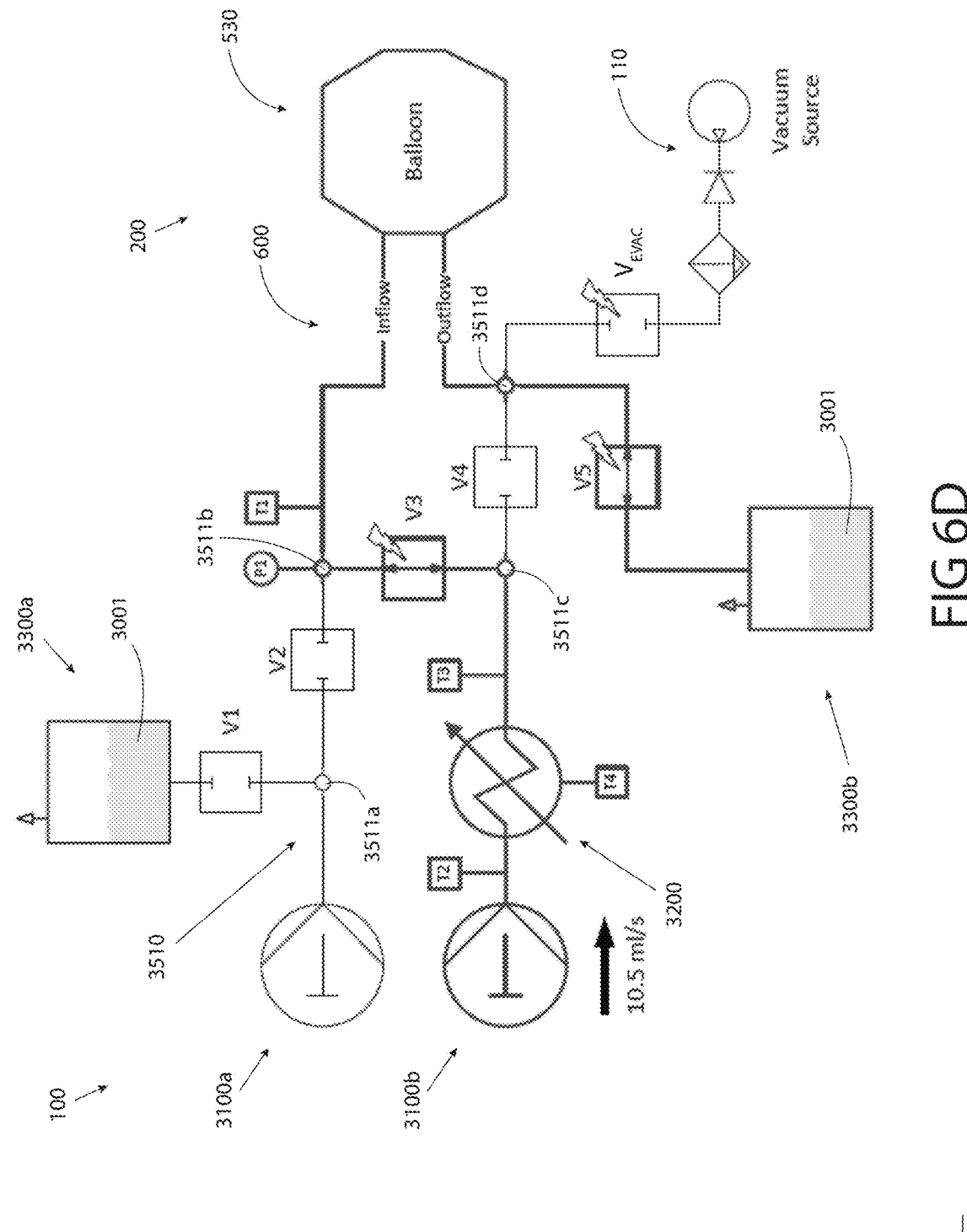

Referring specifically to FIG. 6D, an operational state of system 10 associated with a fourth mode of operation, Mode T1, is illustrated, consistent with the present inventive concepts. In Mode T1, valves V3 and V5 are opened, such that syringe pump assembly 3100*b* is fluidly connected to reservoir 3300*b* via heater assembly 3200 and expandable element 530. Valve V2 is closed such that junction 3511*b* is isolated from junction 3511*a*, and valve V4 is closed such that junction 3511*c* is only in fluid communication with junction 3511*d* via expandable element 530. The plunger of syringe pump assembly 3100*b* is advanced, forcing fluid 3001W to flow through heater assembly 3200. Heater assembly 3200 is active, such that warm fluid 3001W is heated to an ablative temperature (e.g. an elevated ablative temperature, such as a temperature of at least 37° C., such as at least 78° C., such as approximately 98° C., such as at least 100° C., such as at least 120° C.). The ablative fluid, hot fluid 3001H, leaving heater assembly 3200 flows through the inflow lumen of umbilical 600, expandable element 530, and the outflow lumen of umbilical 600, and into reservoir 3300*b*.

In alternate embodiments, syringe pump assembly 3100*b* can comprise a heating element configured to heat the fluid within syringe pump assembly 3100*b*. Fluid 3001 can be drawn into syringe pump assembly 3100*b*, heated to an ablative temperature, and subsequently forced through expandable element 530, with or without passing first through a heater assembly (e.g. heater assembly 3200).

As described herein, valve V$_{EVAC}$ can be configured to open automatically if system 10 enters an alert state, such that vacuum source 110 is fluidly attached to expandable element 530. In this state, vacuum source 110 extracts fluid 3001H from expandable element 530, such as to protect the patient from unintended burns caused by fluid 3001H remaining within expandable element 530 (e.g. during a power failure). Alternatively or additionally, in some embodiments, reservoir 3300b is positioned below (e.g. closer to the ground) expandable element 530, such that in an alert state (e.g. a power loss), gravity can syphon fluid 3001H from expandable element 530. In these embodiments, valve V5 can comprise a normally open valve such that in the event of a power failure, the fluid path between expandable element 530 and reservoir 3300b is maintained. In some embodiments, one or more valves between reservoir 3300a, expandable element 530, and reservoir 3300b are normally open (e.g. valves V1, V2, and V5), and other system valves (e.g. valves V3, V4, and V$_{EVAC}$) are normally closed, such that the syphon pulls fluid 3001 from reservoir 3300a and through expandable element 530, displacing fluid 3001H. In some embodiments, one or more valves between reservoir 3300a, expandable element 530, and vacuum assembly 110 are normally open (e.g. valves V1, V2, and V$_{EVAC}$), such that in the event of a power failure, vacuum assembly 110 pulls fluid 3001 from reservoir 3300a and through expandable element 530, displacing fluid 3001H.

Figure 6E:
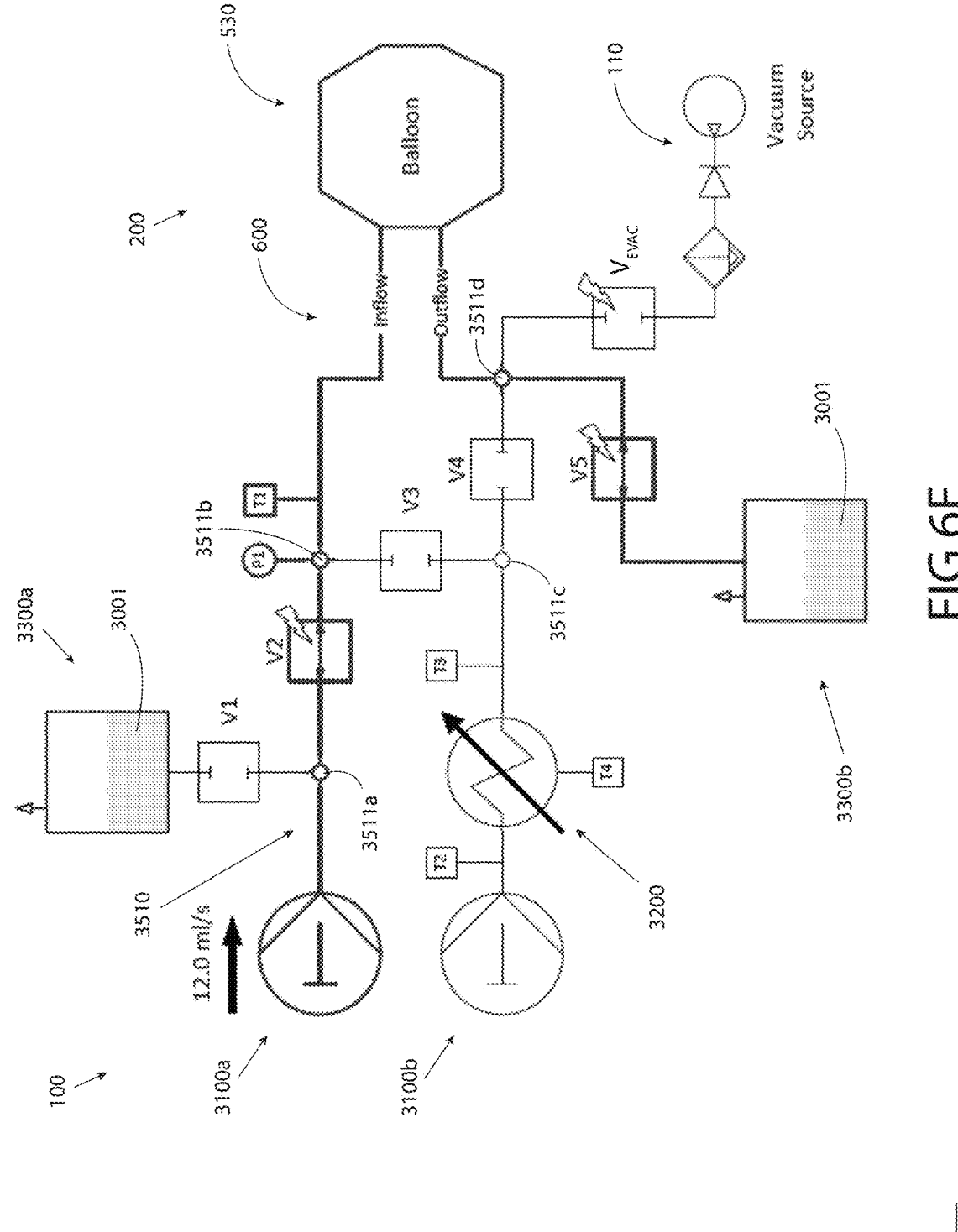

Referring specifically to FIG. 6E, an operational state of system 10 associated with a fifth mode of operation, Mode C1, is illustrated, consistent with the present inventive concepts. In Mode C1, valves V1, V3, V4 and V$_{EVAC}$ are closed. Valves V2 and V5 are opened, such that syringe pump assembly 3100a is fluidly connected to reservoir 3300b via expandable element 530. The plunger of syringe pump assembly 3100a is advanced, forcing fluid 3001 to flow through expandable element 530 to reservoir 3300b.

Figure 6F:
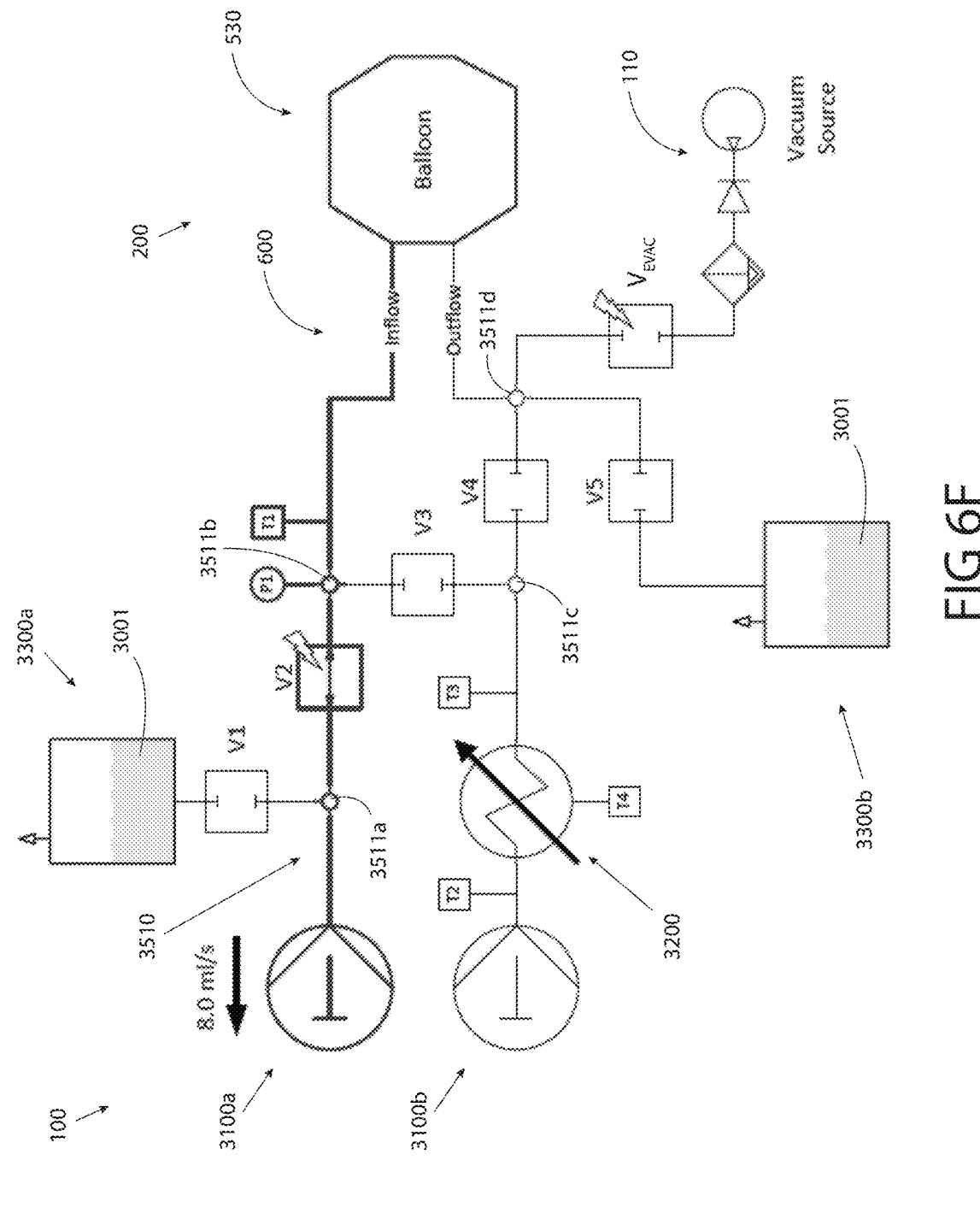

Referring specifically to FIG. 6F, an operational state of system 10 associated with a sixth mode of operation, Mode D1, is illustrated, consistent with the present inventive concepts. In mode D1, valves V1, V3, V4, V5, and V$_{EVAC}$ are closed. Valve V2 is opened, such that syringe pump assembly 3100a is in fluid communication with expandable element 530. The plunger of syringe pump assembly 3100a is retracted, such that fluid 3001 remaining in expandable element 530 is drawn into syringe pump assembly 3100a. Junction 3511d is isolated other than from syringe pump assembly 3100a (via expandable element 530), such that syringe pump assembly 3100a can draw a negative pressure against expandable element 530, causing expandable element 530 to transition to its compacted state.

Referring now to FIG. 6G, a flow chart of a method of treating tissue, Method 2300, is illustrated, consistent with the present inventive concepts. Method 2300 is described using components of system 10, as described herein. In Step 2310, preparation for an ablative treatment is performed. In some embodiments, steps similar to Steps 2210 to 2230 of Method 2200 are performed, as described in reference to FIG. 1B herein. In some embodiments, catheter 200 is introduced into the small intestine of the patient such that expandable element 530 is proximate a location to be thermally ablated, and at least one submucosal expansion procedure is performed. In some embodiments, Method 2300 does not continue beyond Step 2310 prior to receiving a positive operator confirmation (e.g. via operator input to system 10), such as in the event that expandable element 530 is in the proper position relative to target tissue to be treated.

In Step 2320, console 100 is configured as illustrated in FIG. 6A, described herein. In Step 2320, valve V1 is opened and the plunger of syringe pump assembly 3100a is retracted to draw a first volume of fluid 3001, volume VOL1, from reservoir assembly 3300a and into syringe pump assembly 3100a. In some embodiments, fluid 3001 is drawn into syringe pump assembly 3100a at a rate of at least 4 ml/s, such as at least 6 ml/s, such as at least 8 ml/s. In some embodiments, at least 10 ml, such as at least 50 ml, such as at least 70 ml, such as at least 90 ml, such as at least 200 ml of fluid is drawn into syringe pump assembly 3100a. In some embodiments, fluid 3001 comprises room temperature fluid, for example, fluid at a temperature of approximately 20° C. In some embodiments, fluid 3001 comprises a fluid at a temperature below body temperature. In some embodiments, the performance of system 10 is independent of the temperature of fluid 3001. Additionally or alternatively, the temperature of fluid 3001 can be uncontrolled (e.g. uncontrolled by system 10, such as permitted to adopt room temperature fluid), and one or more parameters of a treatment procedure as described herein is determined based on a measured (but uncontrolled) temperature of fluid 3001. In some embodiments, fluid 3001 is chilled by system 10, such as fluid chilled within reservoir assembly 3300a, fluid chilled within syringe pump assembly 3100a, and/or fluid chilled when passing through a chiller assembly not shown, but for example, positioned in line between reservoir assembly 3300a and syringe pump assembly 3100a.

In Step 2330, console 100 is configured as illustrated in FIG. 6B, described herein. After Step 2320, in Step 2330, valve V1 is closed and valve V2 is opened. The plunger of syringe pump assembly 3100a is driven forward, driving a first portion, portion P1, of the first volume VOL1 of fluid 3001 from syringe pump assembly 3100a to expandable element 530. Expandable element 530 radially expands as fluid 3001 is delivered from syringe pump assembly 3100a. In some embodiments, fluid 3001 is driven into expandable element 530 at a rate of at least 2 ml/s, such as at least 3 ml/s, such as 3.75 ml/s.

In Step 2340, console 100 is configured as illustrated in FIG. 6C, described herein. After Step 2330, in Step 2340, valve V4 is opened and the plunger of syringe pump assembly 3100b is retracted to draw a second volume of fluid 3001, volume VOL2, from expandable element 530 into syringe pump assembly 3100b. The second volume VOL2 comprises portion P1 of the first volume VOL1, and at least some of a second portion, portion P2, of the first volume VOL1 which is driven from syringe pump assembly 3100a during Step 2340. This reuse of one or more portions of volume VOL1, and/or other reuse of fluid previously circulated through expandable element 530, results in a reduction in overall fluid 3001 needed to perform the ablation procedure described herein. Fluid 3001 drawn from expandable element 530 into syringe pump assembly 3100b passes through heater assembly 3200. Heater assembly 3200 is set to a first level (e.g. a first level of power), and heats fluid 3001 as it passes therethrough, such that warm fluid 3001W is drawn into syringe pump assembly 3100b (e.g. the second volume VOL2 comprises fluid 3001 which has been warmed to become warm fluid 3001W). In some embodiments, console 100 operates at peak power (e.g. the maximum power console 100 will draw from an electrical source, such as a standard wall electrical outlet) while the first level of power is delivered to heater assembly 3200. By ensuring peak power consumption during Step 2340, it can be presumed that the power consumption of console 100 during subsequent steps of Method 2300 will not cause the tripping of any fuses or other circuit breakers (e.g. circuit breakers of the hospital or other clinical site) that did not trip during Step 2340, thus minimizing the likelihood of tripping the circuit breaker during steps wherein hot fluid is positioned proximate the patient (e.g. in Step 2350 described herein). In some embodiments, warm fluid 3001W is heated to a temperature of at least 40° C., such as at least 50° C., such as at least 75° C., such as at least 100° C. Additionally or alternatively, the warm fluid 3001W is heated to a temperature of at least 10° C., such as at least 50° C., such as at least 90° C. above the temperature of fluid 3001. In some embodiments, the plunger of syringe pump assembly 3100b is retracted at the same speed as the plunger of syringe pump assembly 3100a is advanced (e.g. when syringe pump assembly 3100a and 3100b comprise similar diameters) such that fluid 3001W is drawn into syringe pump assembly 3100b at the same rate that fluid is driven from syringe pump assembly 3100a.

In some embodiments, in Step 2340, console 100 is configured to monitor one or more parameters of system 10 (e.g. the pressure of fluid 3001 as recorded by a pressure sensor of console 100 or cartridge 3500) to determine the mechanical and/or clinical integrity of catheter 200. For example, if the pressure of fluid 3001 is below an expected threshold, console 100 can enter an alert state during which subsequent steps are not performed and indicate to the operator that expandable element 530 may be compromised (e.g. burst). In some embodiments, console 100 is configured to identify leaks and/or flow obstructions based on the monitored parameters. In some embodiments, console 100 continues to monitor these parameters during subsequent steps described herein. In some embodiments, the criteria (e.g. one or more threshold or other limits) for a leak or obstruction detection can be adjusted based on the temperature of the fluid being circulated through catheter 200. For example, a pressure threshold for detecting an obstruction (e.g. threshold above which an obstruction is indicated) can comprise a relatively lower threshold when colder fluid is being circulated, as opposed to a relatively higher threshold when warmer fluid is being circulated. In some embodiments, the criteria is adjusted based on the temperature of fluid 3001 within reservoir 3310a.

In some embodiments, prior to Step 2350, console 100 is configured to ensure that syringe 3110a holds an adequate volume of fluid 3001 to perform Step 2360 (e.g. to cool the ablated tissue). If it is determined that there is not a sufficient volume fluid 3001 within syringe 3110a, console 100 can enter an alert state, and for example, prevent hot fluid 3001H from being delivered to expandable element 530.

In Step 2350, console 100 is configured as illustrated in FIG. 6D, described herein. After Step 2340, in Step 2350, valves V2 and V4 are closed, and valves V3 and V5 are opened. The plunger of syringe pump assembly 3100a is stopped, and the plunger of syringe pump assembly 3100b is driven forward, driving the second volume VOL2 of fluid (e.g. warm fluid 3001W) from syringe pump assembly 3100b, through heater assembly 3200. In some embodiments, all of the second volume VOL2 has been previously circulated through expandable element 530 (e.g. in Steps 2330 and/or 2340). Alternatively, in some embodiments, at least a portion of the second volume VOL2 has been previously circulated through expandable element 530 (e.g. in Step 2330). In some embodiments, fluid 3001W is driven from syringe pump assembly 3100b at a rate of at least 8 ml/s, such as at least 10 ml/s, such as 10.5 ml/s. In some embodiments, fluid 3001W is driven from syringe pump assembly 3100b at a rate that is at least twice as fast as the rate fluid 3001W was drawn into syringe pump assembly 3100b in Step 2340. Heater assembly 3200 is powered to a second level, and heats warm fluid 3001W as it passes therethrough, such that hot fluid 3001H exits heater assembly 3200 and continues to expandable element 530. In some embodiments, the second level is less than the first level of Step 2340 (e.g. heater assembly draws less power when powered to the second level than when powered to the first level). In some embodiments, the second level is at least 25% less than the first level, such as at least 50% less than the first level. Alternatively, the second level can be more than the first level, such as at least 25% more than the first level. From expandable element 530, hot fluid 3001H is free to flow past valve V5 and into reservoir assembly 3300b. In some embodiments, hot fluid 3001H is heated to a temperature of at least 37° C., such as at least 78 C, such as approximately 98° C., such as at least 100° C., such as at least 120° C. Additionally or alternatively, the hot fluid 3001H is heated to a temperature of at least 5° C. above the temperature of warm fluid 3001W, such as at least 15° C., at least 30° C., or at least 80° C. above the temperature of warm fluid 3001W. Hot fluid 3001H can be circulated though expandable element 530 for at least 1 second, such as for at least 5 seconds, such as approximately 10 seconds. In some embodiments, the duration of Step 2350 is based on the temperature of fluid 3001, the temperature of warm fluid 3001W, and/or the temperature of hot fluid 3001H.

In some embodiments, console 100 is configured to monitor one or more parameters of system 10 to detect if any leaks or other issues are present or occur during Step 2350 (or other steps of Method 2300). In some embodiments, if a leak is detected during Step 2350, Method 2300 continues automatically and immediately to Step 2360, during which fluid 3001 (e.g. fluid at room temperature or below) is flushed through expandable element 530. Additionally or alternatively, console 100 can be configured to monitor one or more parameters of system 10 to detect if any occlusions are present and/or occur during Step 2350 (and/or other steps of Method 2300). If an occlusion is detected, system 10 can be configured to enter an alert state, such as an alert state in which console 100 deflates expandable element 530 and/or delivers neutralizing fluid to expandable element 530.

In Step 2360, console 100 is configured as illustrated in FIG. 6E, described herein. After Step 2350, in Step 2360, valve V3 is closed and valve V2 is opened. The plunger of syringe pump assembly 3100b is stopped, and the plunger of syringe pump assembly 3100a is again driven forward, driving a third portion, portion P3, of the first volume VOL1 of fluid 3001 from syringe pump assembly 3100a. The third portion P3 of the first volume VOL1 of fluid 3001 is driven through expandable element 530 and is free to flow past valve V5 and into reservoir assembly 3300b. In some embodiments, fluid 3001 is driven from syringe pump assembly 3100a at a rate of at least 8 ml/s, such as at least 10 ml/s, such as at least 12 ml/s. In some embodiments, fluid 3001 is driven from syringe pump assembly 3100a at a rate at least 1 ml/s faster than the rate fluid 3001H was driven from syringe pump assembly 3100b in Step 2350. Fluid 3001 can be circulated through expandable element 530 for at least 10 seconds, such as for at least 25 seconds, such as at least 60 seconds. In some embodiments, the duration of Step 2360 is based on the temperature of fluid 3001 and/or the temperature of hot fluid 3001H. In some embodiments, fluid 3001 is circulated through expandable element 530 for no more than 15 seconds, such as no more than 25 seconds, such as no more than 60 seconds.

In Step 2370, console 100 is configured as illustrated in FIG. 6F, described herein. After Step 2360, in Step 2370, valve V5 is closed and the plunger of syringe pump assembly 3100a is reversed, drawing fluid 3001 from expandable element 530 back into syringe pump assembly 3100a (e.g. at least some of the third portion P3). In some embodiments, fluid 3001 is drawn from expandable element 530 into syringe pump assembly 3100a at a rate of at least 4 ml/s, such as at least 6 ml/s, such as at least 8 ml/s. In Step 2370, with valves V1, V3, V4, V5, and $V_{EVAC}$ all closed, drawing fluid from expandable element 530 can cause expandable element 530 to radially contract.

In some embodiments, method 2300 can be repeated multiple times in a single procedure, such as to thermally ablate a sufficient amount of mucosal tissue to achieve a desired therapeutic benefit in a patient, such as is described herein. In some embodiments, system 10 is configured to perform all the ablations necessary to achieve the desired therapeutic affect while requiring a target procedural volume of less than 5 L of fluid, such as less than 4 L, 3 L, 2 L, or 1 L of fluid (e.g. reservoir 3310a is filled with less than this fluid volume to start the procedure).

In some embodiments, console 100 is configured to determine appropriate parameters for the actions described in the various steps of Method 2300. For example, console 100 can be configured to determine appropriate flow rates, fluid temperatures, energy levels, pressures, durations, and/ or other system 10 operational parameters for performing Method 2300. In some embodiments, console 100 comprises a predetermined set of operational parameters (e.g. parameters predetermined in a manufacturing process). In some embodiments, a set of operational parameters is determined at a time proximate the time a procedure is performed (e.g. relatively soon before and/or during a procedure). In some embodiments, after the set of these operational parameters is determined, the procedure is performed in an open-loop manner. Alternatively or additionally, console 100 can be configured to monitor one or more conditions of system 10 during the procedure, and adjust one or more operational parameters (e.g. the procedure is performed in a closed-loop manner). In some embodiments, system 10 is configured to adjust two or more operational parameters independently, such as when flow rate and fluid temperature are independently controllable. In some embodiments, one or more operational parameters are controlled to achieve precise depth of ablation of intestinal tissue. In some embodiments, console 100 is configured to determine one or more parameters based on one or more user inputs or operational conditions. For example, console 100 can determine parameters based on information selected from the group consisting of: ambient temperature (e.g. room temperature); the temperature of fluid 3001; the temperature of hot fluid 3001H; elevation above sea level; treatment location; and combinations of these. Additionally or alternatively, console 100 can determine parameters based on one or more user inputs selected from the group consisting of: desired ablative power; desired depth of ablation; duodenal wall thickness; time since previous ablations; desired duration of ablation; desired temperature of ablation; and combinations of these.

In some embodiments, hot fluid 3001H is heated via a two-stage heating cycle (e.g. reducing the need for high electrical power) that avoids the need for a hot reservoir that is maintained at an elevated temperature for a prolonged period of time. Hot fluid 3001H can be driven at a flow rate of at least 5 mL/s, and at a temperature near 100° C. The two-stage heating cycle can comprise two passes through a single heater, such as when the first pass is performed at a slower flow rate than the second pass. In some embodiments, the heater is configured to deliver power up to at least 900 W, such as at least 1000 W, or at least 1100 W. In some embodiments, a first pass through heater 3210 heats hot fluid 3001H to at least 75° C., such as at least 80° C., or at least 85° C. In these embodiments, on a second pass (e.g. through heater 3210), hot fluid 3001H is heated to a desired temperature in a closed loop fashion (e.g. using a temperature sensor). Hot fluid 3001H can be heated to a desired temperature of at least 93° C., such as at least 95° C., or 97° C. Hot fluid 3001H can be heated to the desired temperature in a time period of no more than 2 sec, such as no more than 1.5 sec, or no more than 1 sec. Hot fluid 3001H can be heated to within 0.5° C. of the desired temperature, such as within 0.3° C., such as within 0.1° C. In some embodiments, hot fluid 3001H can be heated in a second pass while flowing at a rate of at least 9 ml/min, such as at least 10 ml/min, or at least 10.5 ml/min.

Figure 7:
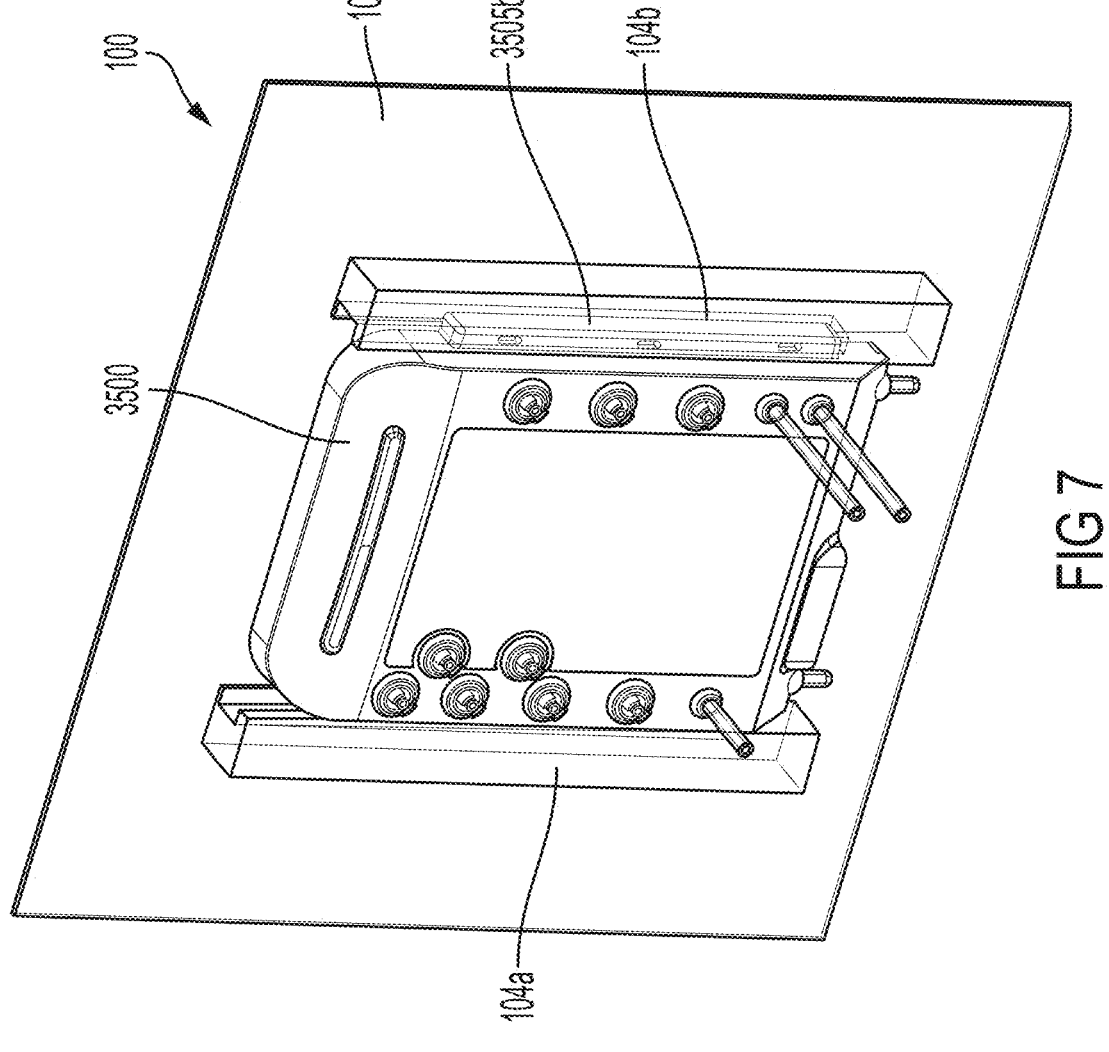
FIG. 7 illustrates a perspective view of a cartridge operably attached to a console, consistent with the present inventive concepts.

Referring now to FIG. 7, a perspective view of a cartridge operably attached to a console is illustrated, consistent with the present inventive concepts. A portion of housing 101 of console 100 is shown. Console 100 can comprise retention mechanisms, such as tracks 104a and 104b shown. Tracks 104a,b can be configured to slidingly receive at least a portion of cartridge 3500. For example, cartridge 3500 can comprise projections 3505a and 3505b (projection 3505a obscured in FIG. 7 by a portion of cartridge housing 3501). Console 100 and cartridge 3500 can be of similar construction and arrangement to the similar components described herein. In some embodiments, cartridge 3500 can be lockably attached to console 100, such as via one or more locking mechanisms described in reference to FIGS. 9A-9D herein. In some embodiments, system 10 is configured to detect when cartridge 3500 has been correctly attached to console 100 (e.g. via one or more sensors). Alternatively or additionally, system 10 can detect if cartridge 3500 has been incorrectly attached to console 100, and system 10 can be configured to enter an alert mode if an incorrect attachment has been detected, such as to alert an operator of the system.

Figure 8B:
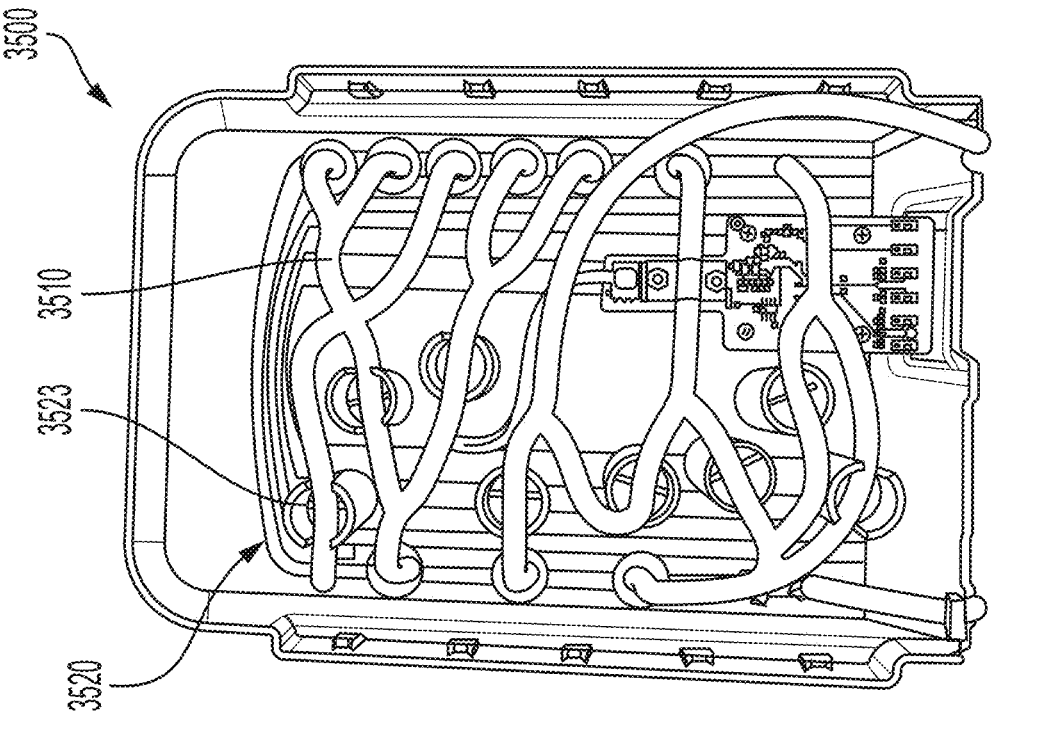
FIGS. 8A and 8B illustrate two perspective views of a cartridge, consistent with the present inventive concepts.
Figure 8A:
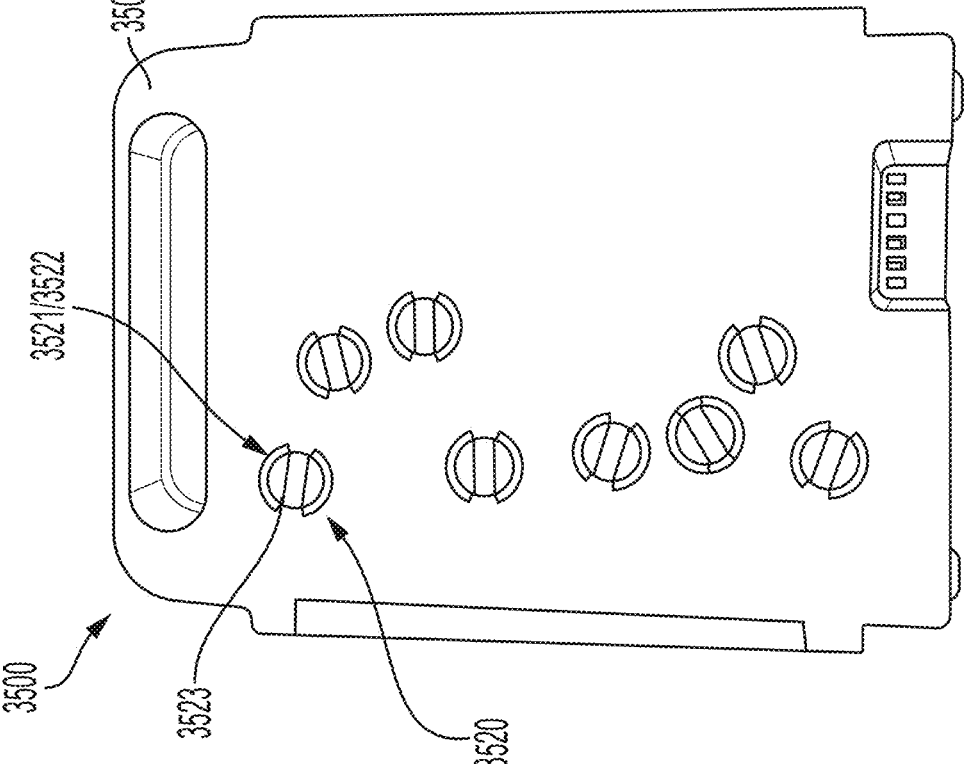

Referring now to FIGS. 8A and 8B, two perspective views of a cartridge are illustrated, consistent with the present inventive concepts. In FIG. 8B, a back-wall portion of housing 3501 of cartridge 3500 has been removed, such that conduits 3510 and other components inside housing 3501 are visible. As shown, cartridge 3500 comprises eight valve assemblies 3520. Each valve assembly 3520 comprises a port 3521 within housing 3501. Each port 3521 comprises an opening 3522 through housing 3501, and walls 3523 surrounding the port. Each valve assembly comprises a portion of a conduit 3510 extending therethrough, as shown in FIG. 8B.

Figure 9A:
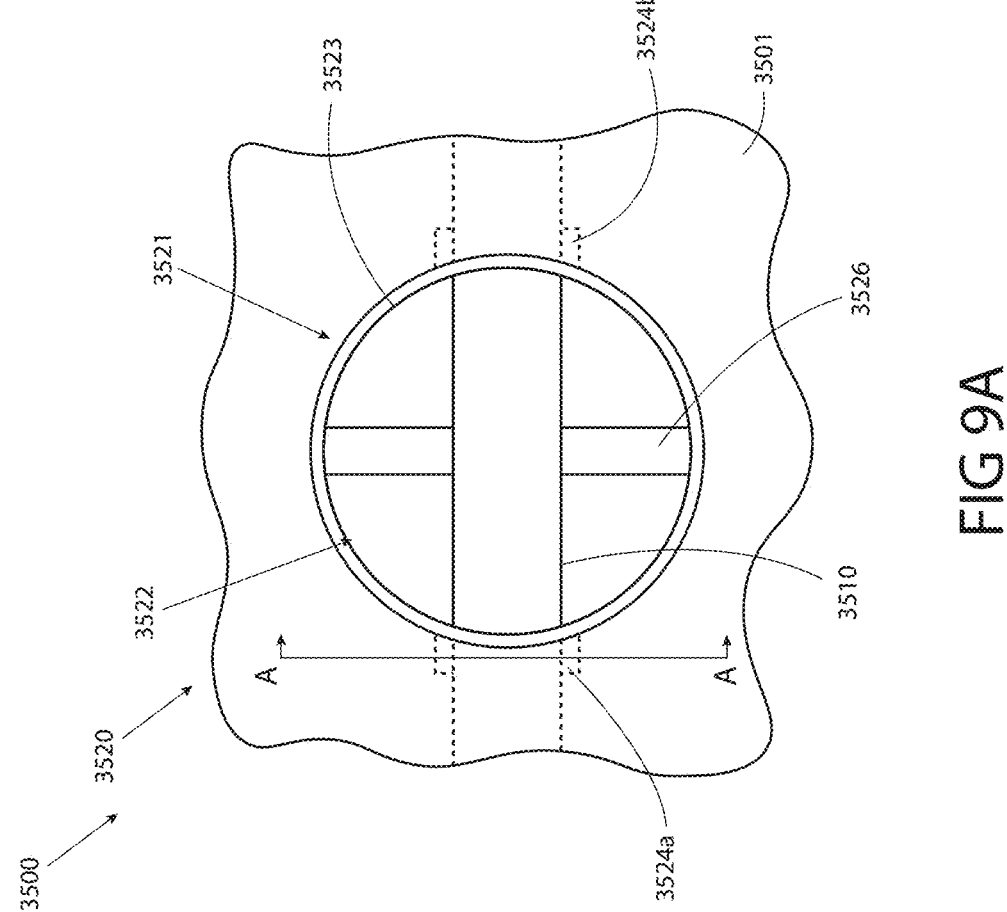
FIGS. 9A-9D illustrate valve assemblies configured to pinch the walls of conduits to control the flow of fluid through a cartridge.
Figures 9B, 9C, 9D:
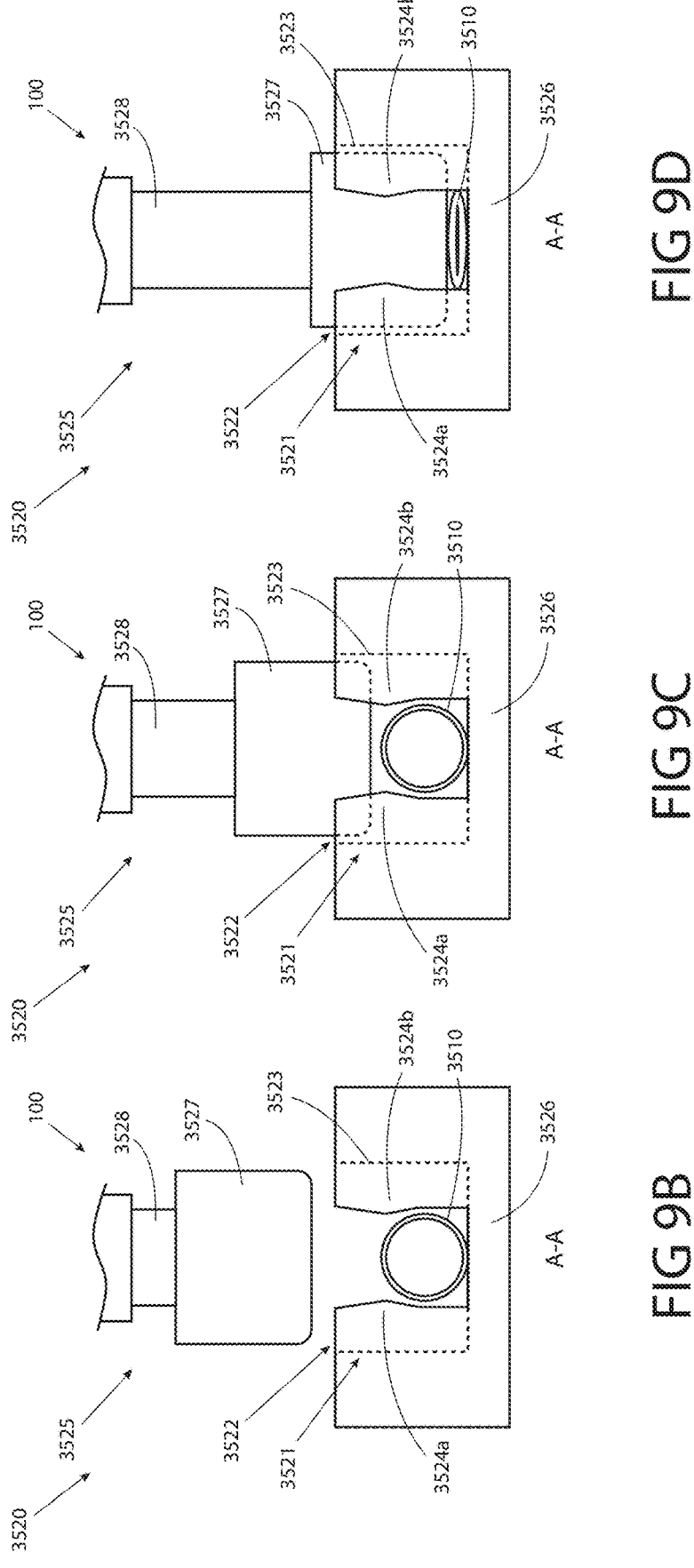

Referring additionally to FIGS. 9A-9D, a portion of a valve assembly 3520 and three sectional views of the valve assembly in various configurations are illustrated, respectively, consistent with the present inventive concepts. In some embodiments, cartridge 3500 is configured to be slidingly inserted into a portion of console 100 (e.g. as described in reference to FIG. 7 herein), and subsequently be lockingly engaged to console 100. In some embodiments, console 100 comprises one or more extendable projections (e.g. a portion of piston assembly 3525 described herebelow) configured to engage with one or more corresponding recesses of cartridge 3500 (e.g. ports 3521 described herebelow). These mating projections and recesses can be constructed and arranged to prevent cartridge 3500 from sliding within the receiving portion of console 100 (e.g. prevent cartridge 3500 from being removed from console 100). In some embodiments, one or more valve assemblies 3520 include the projections that extend from console 100, as well as the recesses positioned within cartridge 3500 (e.g. as described herebelow). FIGS. 9B-9D are sectional views along section A-A of FIG. 9A. FIG. 9A illustrates a portion of cartridge 3500 including a portion of a valve assembly 3520. FIG. 9B illustrates a valve assembly 3520 in an unlocked configuration, such that cartridge 3500 can be attached to and/or removed from console 100 in the unlocked configuration. FIG. 9C illustrates valve assembly 3520 in a locked and open configuration, such that cartridge 3500 is attached to console 100 in a locked state, and valve assembly 3520 is open such that fluid is free to flow through conduit 3510. FIG. 9D illustrates valve assembly 3520 in a locked and closed configuration, such that cartridge 3500 is attached to console 100 in a locked state, and valve assembly 3520 is closed such that fluid is prevented from flowing through conduit 3510.

Each valve assembly 3520 can include a port 3521, surrounding an opening 3522 in housing 3501, where opening 3522 exposes a portion a conduit 3510 extending through port 3521. Port 3521 is surrounded by walls 3523. Valve assembly 3520 can include one or more retention mechanisms, clips 3524a and 3524b shown, which maintain the exposed portion of conduit 3510 within the center of port 3521. Valve assembly 3520 can include a piston assembly 3525, comprising a shaft 3528 extending from a portion of console 100 towards port 3521. Shaft 3528 can comprise piston head 3527 on its distal end. Piston head 3527 can be sized and positioned to be slidingly received within port 3521. As shown in FIG. 9C, in a locked configuration, piston assembly 3525 extends from console 100, such that a portion of piston head 3527 extends into port 3521.

Within each port 3521, and positioned opposite opening 3522, a projection, ridge 3526, extends towards opening 3522. Conduit 3510 can be positioned against ridge 3526 (e.g. held in contact with ridge 3526 by clips 3524). In some embodiments, piston assembly 3525 is configured to extend further into port 3521, such that piston head 3527 compresses conduit 3510 against ridge 3526 (e.g. effectively causing valve assembly 3520 to transition to a closed configuration).

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the inventive concepts, which is defined in the accompanying claims.

What is claimed is:

1. A system for performing a medical procedure in the intestine of a patient, the system comprising:
   a catheter for insertion into the intestine, the catheter comprising:
   a shaft including a distal portion, and
   a functional assembly positioned on the distal portion of the shaft, wherein the functional assembly is configured to receive fluid;
   a console comprising:
   a fluid reservoir configured to store the fluid,
   a first syringe pump assembly comprising a first syringe and a first plunger configured to retract to draw fluid into the first syringe and to advance to deliver fluid from the first syringe to the functional assembly,
   a second syringe pump assembly comprising a second syringe and a second plunger configured to retract to draw fluid into the second syringe and to advance to deliver the fluid from the second syringe to the functional assembly,
   a fluid heater comprising a flow path configured to receive fluid in a first direction and in a second, opposite direction configured to heat the fluid flowing through the flow path, and
   a waste fluid reservoir configured to receive the fluid from the functional assembly; and
   a connector configured to operably attach the catheter to the console;
   wherein the console is operable in a heating-and-delivery arrangement in which (i) retraction of the second plunger draws fluid from the functional assembly through the flow path of the fluid heater in the first direction while the fluid heater heats the fluid to produce warmed fluid within the second syringe, and (ii) thereafter, advancement of the second plunger forces the warmed fluid from the second syringe through the flow path of the fluid heater in the second direction while the fluid heater heats the warmed fluid to produce ablative-temperature fluid delivered to the functional assembly; and
   wherein the system is configured to treat target tissue of the intestine of the patient.

2. The system according to claim 1, wherein the functional assembly comprises a balloon.

3. The system according to claim 1, wherein the system is configured to treat the target tissue by:
   providing a first volume of the fluid at a temperature below body temperature and recirculating the first volume of the fluid within the functional assembly to cool the target tissue and tissue proximate the target tissue; and
   providing a second volume of the fluid at an elevated ablative temperature and recirculating the second volume of the fluid within the functional assembly to ablate the target tissue.

4. The system according to claim 3, wherein the system is configured to deliver the first volume of the fluid prior to the delivery of the second volume of the fluid or after the delivery of the second volume of the fluid.

5. The system according to claim 3, wherein the system is configured to deliver the first volume of the fluid prior to the delivery of the second volume of the fluid, wherein the system is further configured to deliver a third volume of the fluid after the delivery of the second volume of the fluid, and wherein the third volume of the fluid comprises fluid at a temperature below body temperature that during its delivery cools the target tissue and tissue proximate the target tissue.

6. The system according to claim 3, wherein the fluid heater comprises an inline heater, and wherein the console is operable such that the second volume of the fluid is heated by the inline heater via two passes through the inline heater in a first direction during a fill stroke of the second syringe pump assembly and in a second, opposite direction during a dispense stroke of the second syringe pump assembly.

7. The system according to claim 6, wherein during the first pass through the inline heater, the inline heater is configured to be powered to a higher level than during the second pass through the inline heater.

8. The system according to claim 3, wherein the first volume of the fluid comprises fluid at room temperature.

9. The system according to claim 3, wherein the console is operable such that the treatment further comprises delivering a third volume of the fluid to cool the target tissue after the target tissue has been ablated.

10. The system according to claim 9, wherein the console is configured to prevent delivery of the second volume of fluid to the functional assembly unless a volume of at least the third volume of the fluid is present in the first syringe pump assembly prior to the delivery of the second volume of fluid to the functional assembly.

11. The system according to claim 1, wherein the fluid heater comprises an inline heater, and wherein the fluid heater is configured to be pre-heated prior to delivery of heated fluid to the functional assembly.

12. The system according to claim 11, wherein the system is configured to perform multiple treatment steps, and wherein the fluid heater is configured to be pre-heated between each of the multiple treatment steps.

13. The system according to claim 1, further comprising a closed-loop control algorithm configured to control the fluid heater.

14. The system according to claim 1, wherein the console is configured to determine one or more parameters related to the treatment of the target tissue, and wherein the one or more treatment parameters are selected from the group consisting of: a flow rate; a fluid temperature; an energy level; a pressure; a duration; and combinations thereof.

15. The system according to claim 1, wherein the console further comprises a backup power supply, wherein the backup power supply comprises an energy capacity sufficient to allow the system to transition one or more components of the system into a patient-safe mode, and wherein the system is configured to transition from a treatment mode to a patient-safe mode in the event of a power failure during treatment of the target tissue.

16. The system according to claim 1, wherein the console is configured to monitor one or more parameters of the system to assess the mechanical integrity of the catheter, and wherein the system is configured to monitor for leaks while fluid at an ablative temperature is being circulated through the functional assembly and to cause cooling fluid to be delivered to the functional assembly upon detection of a leak.

17. The system according to claim 1, wherein the system does not comprise more than two syringe pump assemblies configured to deliver fluid to the functional assembly, and wherein the first syringe pump assembly comprises a single syringe and the second syringe pump assembly comprises a single syringe.

18. The system according to claim 1, wherein the system is configured to prevent the treatment of target tissue if fluid in the fluid reservoir is not above a minimum volume.

19. The system according to claim 1, wherein the system is configured to prevent the treatment of target tissue if space in the waste reservoir is not above a minimum volume.

20. The system of claim 1, wherein the console comprises a first temperature sensor positioned proximate a first port of the fluid heater and a second temperature sensor positioned proximate a second port of the fluid heater, the first and second temperature sensors being configured to sense temperatures of fluid entering and exiting the fluid heater; and wherein the console controls power to the fluid heater based on the sensed temperatures.

21. The system of claim 1, wherein the fluid heater is operated at a first power level during the retraction of the second plunger and at a second power level during the advancement of the second plunger, the second power level being less than the first power level.

22. A console for performing a medical procedure in the intestine of a patient, the console comprising:
a connector configured to operably attach to a catheter, the catheter being insertable into the intestine and comprising a balloon configured to receive fluid for thermal ablation;
a fluid reservoir interface configured to receive a fluid reservoir containing the fluid;
a first syringe pump assembly comprising a first syringe and a first plunger configured to retract to draw the fluid into the first syringe and to advance to deliver the fluid from the first syringe to the catheter;
a second syringe pump assembly comprising a second syringe and a second plunger configured to retract to draw the fluid into the second syringe and to advance to deliver the fluid from the second syringe to the catheter;
a fluid heater comprising a flow path in fluid communication with the second syringe pump assembly, the flow path being configured to convey fluid in a first direction and in a second, opposite direction, and the fluid heater being configured to heat fluid flowing through the flow path; and
a waste reservoir interface configured to receive a waste fluid reservoir configured to receive the fluid from the catheter;
wherein the console is operable in a heating-and-delivery arrangement in which (i) retraction of the second plunger draws fluid from the catheter through the flow path of the fluid heater in the first direction while the fluid heater heats the fluid to produce warmed fluid within the second syringe, and (ii) thereafter, advancement of the second plunger forces the warmed fluid from the second syringe through the flow path of the fluid heater in the second direction while the fluid heater heats the warmed fluid to produce ablative-temperature fluid delivered to the catheter;
wherein the console is configured to treat target tissue of the intestine of the patient when the catheter is connected to the connector.

23. The console of claim 22, further comprising a first temperature sensor positioned proximate a first port of the fluid heater and a second temperature sensor positioned proximate a second port of the fluid heater, the first and second temperature sensors being configured to sense temperatures of fluid entering and exiting the fluid heater, wherein the console is configured to control power to the fluid heater based on the sensed temperatures.

24. The console of claim 22, wherein the console is operable such that the fluid heater is powered at a first power level while the second plunger retracts to draw fluid through the flow path in the first direction, and is powered at a second power level while the second plunger advances to force fluid through the flow path in the second direction, the second power level being less than the first power level.

* * * * *